United States Patent
Holmquist et al.

(10) Patent No.: US 11,280,799 B2
(45) Date of Patent: Mar. 22, 2022

(54) MASS SPECTROMETRIC DETERMINATION OF NON-DERIVATIZED, NON-METABOLIZED VITAMIN D

(71) Applicant: QUEST DIAGNOSTICS INVESTMENTS INCORPORATED, Wilmington, DE (US)

(72) Inventors: Brett Holmquist, Mission Viejo, CA (US); Nigel Clarke, Vista, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 109 days.

(21) Appl. No.: 17/001,425

(22) Filed: Aug. 24, 2020

(65) Prior Publication Data
US 2021/0041464 A1    Feb. 11, 2021

Related U.S. Application Data

(63) Continuation of application No. 16/051,849, filed on Aug. 1, 2018, now Pat. No. 10,753,950, which is a
(Continued)

(51) Int. Cl.
| | | |
|---|---|---|
| *G01N 33/82* | (2006.01) | |
| *G01N 30/72* | (2006.01) | |
| *H01J 49/00* | (2006.01) | |
| *H01J 49/14* | (2006.01) | |
| *G01N 30/00* | (2006.01) | |

(Continued)

(52) U.S. Cl.
CPC ......... *G01N 33/82* (2013.01); *G01N 30/7233* (2013.01); *H01J 49/004* (2013.01); *H01J 49/145* (2013.01); *G01N 2030/009* (2013.01); *G01N 2030/027* (2013.01); *G01N 2030/8813* (2013.01)

(58) Field of Classification Search
CPC .............. G01N 33/82; G01N 30/7233; G01N 2030/009; G01N 2030/027; G01N 2030/8813; H01J 49/004; H01J 49/145
See application file for complete search history.

(56) References Cited

U.S. PATENT DOCUMENTS

| | | |
|---|---|---|
| 4,332,591 A | 6/1982 | Oi et al. |
| 5,614,408 A | 3/1997 | Stanker et al. |
| | (Continued) | |

FOREIGN PATENT DOCUMENTS

| | | |
|---|---|---|
| CN | 1993134 A | 7/2007 |
| JP | H04505468 A | 9/1992 |
| | (Continued) | |

OTHER PUBLICATIONS

Brunetto M.R., et al., "HPLC Determination of Vitamin D(3) and Its Metabolite in Human Plasma with On-line Sample Cleanup," Talanta, Dec. 2004, vol. 64 (5), pp. 1364-1370.
(Continued)

*Primary Examiner* — Jennifer Wecker
*Assistant Examiner* — Michael Paul Shimek
(74) *Attorney, Agent, or Firm* — Quest Diagnostics, Inc.

(57) ABSTRACT

The invention relates to the detection of non-metabolized vitamin D. In a particular aspect, the invention relates to methods for detecting underivatized non-metabolized vitamin D by mass spectrometry.

14 Claims, 37 Drawing Sheets

Related U.S. Application Data continuation of application No. 12/964,710, filed on Dec. 9, 2010, now abandoned.

(60) Provisional application No. 61/285,938, filed on Dec. 11, 2009, provisional application No. 61/285,943, filed on Dec. 11, 2009.

(51) Int. Cl.
  *G01N 30/88* (2006.01)
  *G01N 30/02* (2006.01)

(56) References Cited

U.S. PATENT DOCUMENTS

| | | | |
|---|---|---|---|
| 5,772,874 A | 6/1998 | Quinn et al. | |
| 5,795,469 A | 8/1998 | Quinn et al. | |
| 5,916,523 A | 6/1999 | Yan et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,228,853 B1 | 5/2001 | Dowle et al. | |
| 6,268,144 B1 | 7/2001 | Koester | |
| 6,787,660 B1 | 9/2004 | Armbruster et al. | |
| 6,977,143 B1 | 12/2005 | Caulfield et al. | |
| 7,019,146 B1 | 3/2006 | Ishigai et al. | |
| 7,087,395 B1 | 8/2006 | Garrity et al. | |
| 7,321,116 B2 | 1/2008 | Picard et al. | |
| 7,348,137 B2 | 3/2008 | Caulfield et al. | |
| 7,473,560 B2 | 1/2009 | Soldin | |
| 7,482,162 B2 | 1/2009 | Laurie et al. | |
| 7,618,827 B2 | 11/2009 | Soldin | |
| 7,700,365 B2 | 4/2010 | Singh et al. | |
| 7,745,226 B2 | 6/2010 | Clarke et al. | |
| 7,972,867 B2 | 7/2011 | Clarke et al. | |
| 7,972,868 B2 | 7/2011 | Holmquist et al. | |
| 7,977,117 B2 | 7/2011 | Holmquist et al. | |
| 8,030,084 B2 | 10/2011 | Zhang et al. | |
| 8,034,627 B2 | 10/2011 | Holmquist et al. | |
| 8,076,157 B2 | 12/2011 | Holmquist et al. | |
| 8,084,269 B2 | 12/2011 | Holmquist et al. | |
| 8,101,427 B2 | 1/2012 | Clarke et al. | |
| 8,173,442 B2 | 5/2012 | Holmquist et al. | |
| 8,431,411 B2 | 4/2013 | Clarke et al. | |
| 8,455,259 B2 | 6/2013 | Zhang et al. | |
| 8,574,915 B2 | 11/2013 | Zhang et al. | |
| 8,936,943 B2 | 1/2015 | Clarke et al. | |
| 9,012,394 B2 | 4/2015 | Zhang et al. | |
| 9,046,531 B2 | 6/2015 | Zhang et al. | |
| 9,140,695 B2 | 9/2015 | Kushnir et al. | |
| 9,244,084 B2 | 1/2016 | Clarke et al. | |
| 9,274,124 B2 | 3/2016 | Anderson | |
| 9,529,004 B2 | 12/2016 | Clarke et al. | |
| 9,535,077 B2 | 1/2017 | Holmquist et al. | |
| 9,580,740 B2 | 2/2017 | Zhang et al. | |
| 9,880,180 B2 * | 1/2018 | Clarke | G01N 30/7233 |
| 9,915,663 B2 | 3/2018 | Zhang et al. | |
| 9,970,943 B2 | 5/2018 | Anderson | |
| 10,191,064 B2 | 1/2019 | Zhang et al. | |
| 10,267,810 B2 | 4/2019 | Clarke et al. | |
| 2002/0042112 A1 | 4/2002 | Koster et al. | |
| 2002/0045606 A1 | 4/2002 | Reddy et al. | |
| 2003/0171605 A1 | 9/2003 | Reddy et al. | |
| 2004/0072251 A1 | 4/2004 | Anderson | |
| 2005/0064422 A1 | 3/2005 | Barnidge et al. | |
| 2006/0223188 A1 | 10/2006 | Soldin | |
| 2006/0236886 A1 | 10/2006 | Leenders et al. | |
| 2006/0263886 A1 | 11/2006 | Peters et al. | |
| 2007/0037286 A1 | 2/2007 | Purkayastha | |
| 2007/0105179 A1 | 5/2007 | Madson | |
| 2007/0139956 A1 | 6/2007 | Sugimoto et al. | |
| 2007/0224628 A1 | 9/2007 | Gordon et al. | |
| 2008/0128606 A1 | 6/2008 | Grant et al. | |
| 2008/0241955 A1 | 10/2008 | Purkayastha et al. | |
| 2008/0287661 A1 | 11/2008 | Jones | |
| 2009/0042213 A1 | 2/2009 | Hoofnagle et al. | |
| 2011/0212534 A1 | 9/2011 | Taylor et al. | |
| 2011/0301063 A1 | 12/2011 | Netzel et al. | |
| 2012/0061562 A1 | 3/2012 | Holmquist et al. | |
| 2014/0127825 A1 | 5/2014 | Dey et al. | |
| 2014/0147878 A1 | 5/2014 | Herman et al. | |
| 2014/0234989 A1 | 8/2014 | Holmquist et al. | |

FOREIGN PATENT DOCUMENTS

| | | |
|---|---|---|
| JP | H06341980 A | 12/1994 |
| JP | H0727763 A | 1/1995 |
| JP | 2002518474 A | 6/2002 |
| JP | 2004515763 A | 5/2004 |
| JP | 2005503534 A | 2/2005 |
| JP | 2007515625 A | 6/2007 |
| JP | 2009115724 A | 5/2009 |
| JP | 2009540275 A | 11/2009 |
| JP | 2009543069 A | 12/2009 |
| JP | 2011505014 A | 2/2011 |
| JP | 6092289 B2 | 3/2017 |
| WO | 9112239 A1 | 8/1991 |
| WO | 9533279 A1 | 12/1995 |
| WO | 9618618 A1 | 6/1996 |
| WO | 9967211 A1 | 12/1999 |
| WO | 0246746 A2 | 6/2002 |
| WO | 02057797 A2 | 7/2002 |
| WO | 2004002996 A1 | 1/2004 |
| WO | 2006034427 A2 | 3/2006 |
| WO | 2006107339 A2 | 10/2006 |
| WO | 2006107814 A2 | 10/2006 |
| WO | 2007039193 A1 | 4/2007 |
| WO | 2007139956 A2 | 12/2007 |
| WO | 2008005846 A2 | 1/2008 |
| WO | 2008027861 A1 | 3/2008 |
| WO | 2008097246 A2 | 8/2008 |
| WO | 2008156139 A1 | 12/2008 |
| WO | 2009070594 A1 | 6/2009 |
| WO | 2011072152 A1 | 6/2011 |
| WO | 2011116028 A1 | 9/2011 |
| WO | 2012111249 A1 | 8/2012 |

OTHER PUBLICATIONS

Extended European Search Report for Application No. EP19182389.7, dated Nov. 23, 2020, 14 pages.

Higashi Tatsuya et al., "Advances in Determination of Vitamin D Related Compounds in Biological Samples Using Liquid Chromatography mass Spectrometry: A Review", Journal of Chromatography B, vol. 878(20), Nov. 18, 2009, pp. 1654-1661.

Non-Final Office Action dated Jan. 27, 2021 for U.S. Appl. No. 15/194,009, filed Jun. 27, 2016.

Rezaee M., et al., "Determination of Organic Compounds in Water Using Dispersive Liquid-Liquid Microextraction," Journal of Chromatography A, May 2006, vol. 1116 (1-2), pp. 1-9.

Non-Final Office Action dated Oct. 4, 2021 for U.S. Appl. No. 16/748,234, filed Jan. 21, 2020.

Aksnes L., "A Simplified High-performance Liquid Chromatographic Method for Determination of Vitamin D3, 25-hydroxyvitamin D2 and 25-Hydroxyvitamin D3 in Human Serum," Scandinavian Journal of Clinical and Laboratory Investigation, 1992, vol. 52, pp. 177-182.

Final Office Action dated Sep. 17, 2021 for U.S. Appl. No. 15/194,009, filed Jun. 27, 2016.

Olkowski A.A., et al., "Rapid HPLC Method for Measurement of Vitamin D3 and 25(OH)D3 in Blood Plasma," International Journal for Vitamin and Nutrition Research, 2003, vol. 73(1), pp. 15-18.

Non-Final Office Action dated Oct. 8, 2008 for U.S. Appl. No. 11/101,166, filed Apr. 6, 2005.

Non-Final Office Action dated Apr. 9, 2013 for U.S. Appl. No. 13/287,012, filed Nov. 1, 2011.

Non-Final Office Action dated Sep. 10, 2014 for U.S. Appl. No. 12/964,710, filed Dec. 9, 2010.

(56) References Cited

OTHER PUBLICATIONS

Non-Final Office Action dated Dec. 11, 2013 for U.S. Appl. No. 14/063,956, filed Oct. 25, 2013.
Non-Final Office Action dated Mar. 11, 2013 for U.S. Appl. No. 13/751,915, filed Jan. 28, 2013.
Non-Final Office Action dated Sep. 11, 2013 for U.S. Appl. No. 13/871,457, filed Apr. 26, 2013.
Non-Final Office Action dated Apr. 12, 2010 for U.S. Appl. No. 11/386,215, filed Mar. 21, 2006.
Non-Final Office Action dated Dec. 12, 2014 for U.S. Appl. No. 14/063,956, filed Oct. 25, 2013.
Non-Final Office Action dated Jan. 12, 2016 for U.S. Appl. No. 14/715,153, filed May 18, 2015.
Non-Final Office Action dated Jan. 12, 2016 for U.S. Appl. No. 14/726,957, filed Jun. 1, 2015.
Non-Final Office Action dated Aug. 13, 2019 for U.S. Appl. No. 16/390,989, filed Apr. 22, 2019.
Non-Final Office Action dated Feb. 13, 2013 for U.S. Appl. No. 12/964,717, filed Dec. 9, 2010.
Non-Final Office Action dated Mar. 13, 2012 for U.S. Appl. No. 13/327,650, filed Dec. 15, 2011.
Non-Final Office Action dated Mar. 13, 2017 for U.S. Appl. No. 14/726,957, filed Jun. 1, 2015.
Non-Final Office Action dated Oct. 15, 2012 for U.S. Appl. No. 12/964,710, filed Dec. 9, 2010.
Non-Final Office Action dated Jun. 16, 2017 for U.S. Appl. No. 15/443,805, filed Feb. 27, 2017.
Non-Final Office Action dated Dec. 18, 2017 for U.S. Appl. No. 14/639,834, filed Mar. 5, 2015.
Non-Final Office Action dated Apr. 19, 2018 for U.S. Appl. No. 15/362,210, filed Nov. 28, 2016.
Non-Final Office Action dated Jun. 19, 2014 for U.S. Appl. No. 14/031,678, filed Sep. 19, 2013.
Non-Final Office Action dated Sep. 19, 2014 for U.S. Appl. No. 14/180,722, filed Feb. 14, 2014.
Non-Final Office Action dated Sep. 19, 2016 for U.S. Appl. No. 14/267,014, filed May 1, 2014.
Non-Final Office Action dated Dec. 20, 2011 for U.S. Appl. No. 13/299,212, filed Nov. 17, 2011.
Non-Final Office Action dated Jun. 20, 2013 for U.S. Appl. No. 13/514,892, filed Jun. 8, 2012.
Non-Final Office Action dated Sep. 20, 2012 for U.S. Appl. No. 13/287,012, filed Nov. 1, 2011.
Non-Final Office Action dated Jul. 21, 2011 for U.S. Appl. No. 13/165,685, filed Jun. 21, 2011.
Non-Final Office Action dated Aug. 22, 2014 for U.S. Appl. No. 13/514,892, filed Jun. 8, 2012.
Non-Final Office Action dated Jan. 22, 2016 for U.S. Appl. No. 14/063,956, filed Oct. 25, 2013.
Non-Final Office Action dated Apr. 23, 2012 for U.S. Appl. No. 13/287,012, filed Nov. 1, 2011.
Non-Final Office Action dated Dec. 23, 2013 for U.S. Appl. No. 14/053,423, filed Oct. 14, 2013.
Non-Final Office Action dated Jun. 24, 2010 for U.S. Appl. No. 11/946,765, filed Nov. 28, 2007.
Non-Final Office Action dated Mar. 24, 2016 for U.S. Appl. No. 15/005,801, filed Jan. 25, 2016.
Non-Final Office Action dated Jun. 25, 2015 for U.S. Appl. No. 14/639,834, filed Mar. 5, 2015.
Non-Final Office Action dated Jun. 26, 2012 for U.S. Appl. No. 13/436,651, filed Mar. 30, 2012.
Non-Final Office Action dated Apr. 27, 2016 for U.S. Appl. No. 14/689,542, filed Apr. 14, 2015.
Non-Final Office Action dated Apr. 28, 2010 for U.S. Appl. No. 12/001,076, filed Dec. 6, 2007.
Non-Final Office Action dated Jun. 28, 2010 for U.S. Appl. No. 12/630,790, filed Dec. 3, 2009.
Non-Final Office Action dated Jul. 29, 2011 for U.S. Appl. No. 13/117,997, filed May 27, 2011.
Non-Final Office Action dated Jun. 29, 2011 for U.S. Appl. No. 13/115,935, filed May 25, 2011.
Non-Final Office Action dated Mar. 29, 2018 for U.S. Appl. No. 15/848,325, filed Dec. 20, 2017.
Non-Final Office Action dated May 29, 2018 for U.S. Appl. No. 15/906,078, filed Feb. 27, 2018.
Non-Final Office Action dated Sep. 29, 2020 for U.S. Appl. No. 16/588,709, filed Sep. 30, 2019.
Non-Final Office Action dated Nov. 30, 2011 for U.S. Appl. No. 13/198,620, filed Aug. 4, 2011.
Non-Final Office Action dated Jan. 31, 2019 for U.S. Appl. No. 15/194,009, filed Jun. 27, 2016.
Odrzywolska M., et al., "Convergent Synthesis, Chiral HPLC, and Vitamin D Receptor Affinity of Analogs of 1,25-Dihydroxycholecalciferol," Chirality, 1999, vol. 11 (3), pp. 249-255.
Olsen J.V., et al., "Trypsin Cleaves Exclusively C-Terminal to Arginine and Lysine Residues," Molecular & Cellular Proteomics, 2004, vol. 3 (6), pp. 608-614.
Ortiz-Boyer F., et al., "Quantitation of Circulating Hydroxyvitamin D3 in Human Plasma by a Continuous Cleanup/concentration Procedure Prior to HPLC-UV Detection," Clinica Chimica Acta, Jun. 1998, vol. 274 (2), pp. 139-149.
Partial European Search Report for Application No. 19182389.7 dated Jul. 3, 2020.
Patent Board Decision—Examiner Affirmed dated Apr. 25, 2016 for U.S. Appl. No. 12/964,717, filed Dec. 9, 2010.
Patent Board Decision dated Jun. 1, 2018 for U.S. Appl. No. 12/964,710, filed Dec. 9, 2010.
Persoon A.C., et al., "Clinical Utility of an Automated Immunochemiluminometric Thyroglobulin Assay in Differentiated Thyroid Carcinoma," Clinical Chemistry, 2006, vol. 52 (4), pp. 686-691.
Iwata T., et al., "Determination of Vitamin D3 and 25-Hydroxyvitamin D3 in Sera by Column-Switching High Performance Liquid Chromatography with Fluorescence Detection," Analytical Sciences, Jun. 1990, vol. 6, pp. 361-366.
Jemal M., et al., "High-Throughput Quantitative Bioanalysis by LC/MS/MS," Biomedical Chromatography, 2000, vol. 14 (6), pp. 422-429.
Jessome L.L., et al., "Ion Suppression: A Major Concern in Mass Spectrometry," LCGC North Ameerica, May 2006, vol. 24 (5), pp. 498-510.
Jones et al., "Vitamin Ds: Metabolites and Analogs. Chapter 2 in Modern Chromatographic Analysis of Vitamins", 3rd Edition, Leenheer et al., eds., New York: Marcel Dekker, Inc., 2002, 79 pages.
Jones G., "Assay of Vitamins D2 and D3, and 25-Hydroxyvitamins D2 and D3 in Human Plasma by High-Performance Liquid Chromatography," Clinical Chemistry, Feb. 1978, vol. 24(2), pp. 287-298.
Jones G., et al., "Biological Activity of 1,25-Dihydroxyvitamin D2 in the Chick," Biochemistry, 1976, vol. 15 (3), pp. 713-716.
Jones G., et al., "Current Understanding of the Molecular Actions of Vitamin D," Third Edition, 2002, 79 pgs., Physiological Reviews, 1998, vol. 78 (4), pp. 1193-1231.
Jordan P.H., et al., "Determination of 25-Hydroxyvitamin D3 in Human Serum by Fluorescence Labelling and High-Performance Liquid Chromatography," Analyst, Dec. 1991, vol. 116(12), pp. 1347-1351.
Kamao M., et al., "C-3 Epimerization of Vitamin D3 Metabolites and Further Metabolism of C-3 Epimers," The Journal of Biological Chemistry, 2004, vol. 279 (16), pp. 15897-15907.
Kamao, M., et al., "Determination of Fat-Soluble Vitamins in Human Plasma, Breast Milk and Food Samples: Application in Nutrition Survey for Establishment of "Dietary Reference Intakes for Japanese"", Journal of Health Science, Feb. 2007, vol. 53(3), pp. 257-262.
Kamao M., et al., "Quantification of Fat-Soluble Vitamins in Human Breast Milk by Liquid Chromatography-tandem Mass Spectrometry," Journal of Chromatography B, 2007, vol. 859 (2), pp. 192-200.

(56) References Cited

OTHER PUBLICATIONS

Kim P.S., et al., "Folding and Assembly of Newly Synthesized Thyroblobulin Occurs in a Pre-Golgi Compartment," The Journal of Biological Chemistry, 1991, vol. 266 (19), pp. 12412-12418.

Kissmeyer A.M., et al., "Sensitive Analysis of 1 alpha, 25-Dihydroxyvitamin D3 in Biological Fluids by Liquid Chromatography-Tandem Mass Spectrometry," Journal of Chromatography A, 2001, vol. 935 (1-2), pp. 93-103.

Kobayashi N., et al., "Production of a Group-Specific Antibody to 1alpha, 25-Dihydroxyvitamin D and Its Derivatives Having the 1alpha, 3beta-Dihydroxylated A-Ring Structure," Steroids, Jul. 1994, vol. 59 (7), pp. 404-411.

Kobayashi N., et al., "Tandem Immunoaffinity Chromatography for Plasma 1 Alpha, 25-Dihydroxyvitamin D3 Utilizing Two Antibodies Having Different Specificities: A Novel and Powerful Pretreatment Tool for 1 Alpha, 25-Dihydroxyvitamin D3 Radioreceptor Assays," The Journal of Steroid Biochemistry and Molecular Biology, 1995, vol. 54 (5-6), pp. 217-226.

Kohl E.A., et al., "Improved High-Pressure Liquid Chromatographic Assay of Serum 25-Hydroxycholecalciferol and 25-Hydroxyergocalciferol After Reverse-Phase Sep-Pak C18 Cartridge Preparation of Sample," Journal of Liquid Chromatography, 1981, vol. 4(11), pp. 2023-2037.

Kushnir M.M., et al., "High Sensitivity Measurement of Thyroglobulin in Serum in Presence of Anti-Thyroglobulin Autoantibodies," May 15, 2012. Retrieved from the Internet: URL:https://www.aruplab.com/Research&Development/resources/Posters/2012/Kushnir_ASMS_0512.pdf.

Kushnir M.M., et al., "Mass Spectrometry Based Method for Accurate Measurement of Thyroglobulin in the Presence of Anti-Thyroglobulin Autoantibodies," May 15, 2012. Retrieved from the Internet: URL:https://www.aruplab.com/Research&Development/resources/Posters/2013/Kushnir_ENDO_0613.pdf.

Kushnir M.M., et al., "Measurement of Thyroglobulin by Liquid Chromatography-Tandem Mass Spectrometry in Serum and Plasma in the Presence of Anti-thyroglobulin Autoantibodies," Clinical Chemistry, 2013, vol. 59(6), pp. 982-990.

LC-MS: Why use it, and what is it?, Metabolite Services at JIC [online], [retrieved on Sep. 6, 2014]. Retrieved from the Internet:[URL:https://WMN.jic.ac.uk/services/metabolomics/topics/lcms/why.htm].

"Screenshot of Google page", Mar. 10, 2016, XP055257300, Retrieved from the Internet: URL: www.google.com.

Learmonth M., et al., "Protein Identification by In-Gel Digestion and Mass Spectrometric Analysis," in: The Proteomics Protocols Handbook, 2005, Chapter 30, Walker J.M., ed., Humana Press, pp. 311-314.

Letter from Norton V.G., Ph.D. Partner, Duane Morris LLP, Sep. 4, 2008.

Luo J.L., et al., "Diagnostic Value of Combing TG, TGAb and Cervical Ultrasonic Examination in the Recurrence or Metastasis Lesion of Differentiated Thyroid Carcinoma after Treatment," Chinese Journal of Clinicians (Electronic Edition), 2012, vol. 6 (3), pp. 580-583.

Luque De Castro M.D., et al., "Determination of Vitamin D3 Metabolites: State-of-the-Art and Trends," Journal of Pharmaceutical and Biomedical Analysis, 1999, vol. 20 (1-2), pp. 1-17.

Magalhaes, P. J., et al., "Detection and Quantification of Provitamin D2 and Vitamin D2 in Hop (Humulus Lupulus L.) By Liquid Chromatography-Diode Array Detection-Electrospray Ionization Tandem Mass Spectrometry.," Journal of Agricultural and Food Chemistry, 2007, vol. 55 (20), pp. 7995-8002.

Mann M., et al., "Analysis of Proteins and Proteomes by Mass Spectrometry," Annual Review of Biochemistry, 2001, vol. 70, pp. 437-473.

Mann M., "Functional and Quantitative Proteomics Using SILAC," Nature Reviews Molecular Cell Biology, 2006, vol. 7 (12), pp. 952-958.

Masuda S., et al., "A Method for the Simultaneous Determination of Vitamins D2,D3 and Their Metabolites in Plasma and Its Application to Plasma Samples Obtained from Normal Subjects and Patients," Food Chemistry, 1992, vol. 45 (3), pp. 215-225.

Maunsell Z., et al., "Routine Isotope-Dilution Liquid Chromatography-Tandem Mass Spectrometry Assay for Simultaneous Measurement of the 25-Hydroxy Metabolites of Vitamins D2 and D3," Clinical Chemist, 2005, vol. 51 (9), pp. 1683-1690.

Meikla.W., et al., "Diagnosis and Management of Thyroid Nodules and Cancer Focus on Thyroglobulin; Thyroglobulin and Thyroid Cancer: Part 2 of Presentation: Analytical Method and Performance", Nov. 16, 2012. Retrieved from the Internet: URL:http://arup.utah.edu/media/thyroidglobulin/thyroid.cancer.pgr.final.pdf.

Merchant M., et al., "Recent Advancements in Surface-Enhanced Laser Desorption/Ionization-Time of Flight-Mass Spectrometry," Electrophoresis, 2000, vol. 21 (6), pp. 1164-1167.

Miller W.L., et al., "Genetic Causes of Rickets," Current Opinions in Pediatrics, 1999, vol. 11 (4), pp. 333-339.

Mitamura K., et al., "Derivatization in Lc Ms," Yakugaku Zasshi, 1998, vol. 118 (6), pp. 206-215.

Murao N., et al., "Ferrocene-Based Diels-Alder Derivatization for the Determination of 1alpha-Hydroxyvitamin D3 in Rat Plasma by High-Performance Liquid Chromatography-Electrospray Tandem Mass Spectrometry," Analytical Biochemistry, 2005, vol. 346 (1), pp. 158-166.

Non-Final Office Action dated Oct. 5, 2018 for U.S. Appl. No. 15/489,551, filed Apr. 17, 2017.

Non-Final Office Action dated Feb. 6, 2019 for U.S. Appl. No. 15/362,210, filed Nov. 28, 2016.

Non-Final Office Action dated Oct. 15, 2018 for U.S. Appl. No. 14/639,834, filed Mar. 5, 2015.

Non-Final Office Action dated May 19, 2020 for U.S. Appl. No. 15/194,009, filed Jun. 27, 2016.

Non-Final Office Action dated Oct. 21, 2019 for U.S. Appl. No. 16/259,696, filed Jan. 28, 2019.

Non-Final Office Action dated Mar. 30, 2020 for U.S. Appl. No. 16/390,989, filed Apr. 22, 2019.

Non-Final Office Action dated May 2, 2017 for U.S. Appl. No. 15/388,844, filed Dec. 22, 2016.

Non-Final Office Action dated Jul. 3, 2017 for U.S. Appl. No. 15/194,009, filed Jun. 27, 2016.

Non-Final Office Action dated Jun. 3, 2019 for U.S. Appl. No. 14/639,834, filed Mar. 5, 2015.

Non-Final Office Action dated May 3, 2016 for U.S. Appl. No. 14/639,834, filed Mar. 5, 2015.

Non-Final Office Action dated Aug. 4, 2011 for U.S. Appl. No. 13/115,916, filed May 25, 2011.

Non-Final Office Action dated Oct. 5, 2010 for U.S. Appl. No. 11/386,215, filed Mar. 21, 2006.

Non-Final Office Action dated Jul. 7, 2010 for U.S. Appl. No. 12/630,796, filed Dec. 3, 2009.

Non-Final Office Action dated Jul. 8, 2020 for U.S. Appl. No. 16/429,941, filed Jun. 3, 2019.

Non-Final Office Action dated May 8, 2018 for U.S. Appl. No. 15/194,009, filed Jun. 27, 2016.

Persoon A.C., et al., "Thyroblobulin (Tg) Recovery Testing with Quantitative Tg Antibody Measurement for Determining Interference in Serum Tg Assays in Diffferentiated Thyroid Carcinoma," Clinical Chemistry, 2006, vol. 52 (6), pp. 1196-1199.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Robb D.B., et al., "Atmospheric Pressure Photoionization: An Ionization Method for Liquid Chromatography-Mass Spectrometry," Analytical Chemistry, 2000, vol. 72 (15), pp. 3653-3659.

Roussis S.G., et al., "Quantitative Determination of Polar and Ionic Compounds in Petroleum Fractions by Atmospheric Pressure Chemical Ionization and Electrospray Ionization Mass Spectrometry," Rapid Communication in Mass Spectrometry, 2002, vol. 16 (13), pp. 1295-1303.

Salek, "Analysis of Thyroblobulin Iodination by Tandem Mass Spectrometry Using Immonium Ions of Monoiodo- and Diiodo-Tyrosine," Proteomics, 2005, vol. 5 (2), pp. 351-353.

(56) References Cited

OTHER PUBLICATIONS

Salm P., et al., "The Quantification of Sirolimus by High-Performance Liquid Chromatography-Tandem Mass Spectrometry and Microparticle Enzyme Immunoassay in Renal Transplant Recipients," Clinical Therapeutics, 2000, vol. 22 Suppl B, pp. B71-B85.

Shimada K., et al., "Cookson-Type Reagents: Highly Sensitive Derivatization Reagents for Conjugated Dienes in High-Performance Liquid Chromatography," The Analyst, Dec. 1991, vol. 116 (12), pp. 1393-1397.

Shimada K., et al., "Retention Behavior of Vitamin D and Related Compounds During High-Performance Liquid Chromatography," Journal of Liquid Chromatography, 1995, vol. 18 (14), pp. 2885-2893.

Shimizu M., et al., "Determination of 25-Hydroxyvitamin D3 in Human Plasma Using a Non-Radioactive Tetranorvitamin D Analogue as an Internal Standard," Journal of Chromatography B, Oct. 1995, vol. 672 (1), pp. 63-71.

Singh F.J., et al., "C-3 Epimers Can Account for a Significant Proportion of Total Circulating 25-Hydroxyvitamin D in Infants, Complicating Accurate Measurement and Interpretation of Vitamin D Status," The Journal of Clinical Endocrinology & Metabolism, 2006, vol. 91 (8), pp. 3055-3061.

Spencer C.A., et al., "Detection of Residual and Recurrent Differentiated Thyroid Carcinoma by Serum Thyroglobulin Measurement," Thyroid, 1999, vol. 9 (5), pp. 435-441.

Spencer C.A., et al., "Thyroglobulin Measurement Techniques, Clinical Benefits, and Pitfalls," Endocrinology Metabolism Clinics of North America, 1995, vol. 24 (4), pp. 841-863.

Steen H., et al., "The ABC's (and XYZ's) of Peptide Sequencing," Nature Reviews Molecular Cell Biology, 2004, vol. 5 (9), pp. 699-711.

Supplementary European Search Report for Application No. EP06749272, dated Feb. 2, 2009, 7 pages.

Supplementary European Search Report for Application No. EP08860014, dated Jan. 28, 2011, 5 pages.

Supplementary European Search Report for Application No. EP10836711, dated Oct. 28, 2013, 11 pages.

Supplementary European Search Report for Application No. EP11184151, dated Dec. 1, 2011, 7 pages.

Tang X.J., et al., "An Investigation of Fragmentation Mechanisms of Doubly Protonated Tryptic Peptides," Rapid Communications in Mass Spectrometry, 1992, vol. 6 (11), pp. 651-677.

Taylor P.J., et al., "Simultaneous Quantification of Tacrolimus and Sirolimus in Human Blood, by High-Performance Liquid Chromatography-Tandem Mass Spectrometry," Therapeutic Drug Monitoring, 2000, vol. 22 (5), pp. 608-612.

Tsugawa N., et al., "Determination of 25-Hydroxyvitamin D in Human Plasma Using High-Performance Liquid Chromatography-Tandem Mass Spectrometry," Analytical Chemistry, 2005, vol. 77 (9), pp. 3001-3007.

Vieth R., et al., "Age-Related Changes in the 25-Hydroxyvitamin D Versus Parathyroid Hormone Relationship Suggest a Different Reason Why Older Adults Require More Vitamin D," Journal of Clinical Endocrinology and Metabolism, 2003, vol. 88 (1), pp. 185-191.

Vieth R., "Vitamin D Supplementation, 25-Hydroxyvitamin D Concentrations, and Safety," The American Journal of Clinical Nutrition, 1999, vol. 69 (5), pp. 842-856.

Vogeser M., et al., "Candidate Reference Method for the Quantification of Circulating 25-Hydroxyvitamin D3 by Liquid Chromatography-Tandem Mass Spectrometry," Clinical Chemistry, 2004, vol. 50 (8), pp. 1415-1417.

Vreeken R.J., et al., "On-Line Post-Column Diels-Alder Derivatization for the Determination of Vitamin D3 and Its Metabolites by Liquid Chromatography/Thermospray Mass Spectrometry," Biological Mass Spectrometry, 1993, vol. 22 (11), pp. 621-632.

Wang K., et al., "An Electron-Capture Dienophile Derivatization Agent for Increasing Sensitivity: Determination of a Vitamin D Analog (Ro 24-2090) in Plasma Sample with Liquid Chromatography/Mass Spectrometry," Analytical Biochemistry, 1996, vol. 243 (1), pp. 28-40.

Watson D., et al., "Analysis of Vitamin D and Its Metabolites Using Thermospray Liquid Chromatography/Mass Spectrometry," Biomedical Chromatography, 1991, vol. 5 (4), pp. 153-160.

Weiskopf A.S., et al., "Examination of Structurally Selective Derivatization of Vitamin D3 Analogues by Electrospray Mass Spectrometry," Journal of Mass Spectrometry, 2001, vol. 36 (1), pp. 71-78.

Wharton B., et al., "Rickets," The Lancet, 2003, vol. 362 (9393), pp. 1389-1400.

Wikipedia., "Definition Selected Reaction Monitoring vs. Multiple Reaction Monitoring," downoaded on Oct. 4, 2019, 3 pages.

Wilson S.R., et al., "Analysis of Vitamin D and Its Metabolites: Derivatization and Detection by Electrospray Ionization Mass Spectrometry," Journal of the Chemical Society, Chemical Communications, 1993, pp. 664-665.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Written Opinion for Application No. PCT/US2010/056886, dated Jan. 14, 2011.

Written Opinion for Application No. PCT/US06/12539, dated Jan. 4, 2007, 3 Pages.

Written Opinion for Application No. PCT/US08/84709, dated Feb. 24, 2009, 9 Pages.

Written Opinion for Application No. PCT/US08/85435, dated Apr. 22, 2009, 5 Pages.

Written Opinion for Application No. PCT/US10/59771, dated Feb. 11, 2011, 4 Pages.

Yan C., et al., "New Techniques of Tandem Mass Spectrometry and Its Application in the Study of Drug Metabolism," Acta Pharmaceutica Sinica, 2000, vol. 35(1), pp. 73-78.

Yeung B., et al., "Characterization of the Metabolic Pathway of 1,25-Dihydroxy-16-Ene Vitamin D3 in Rat Kidney by On-Line High Performance Liquid Chromatography-Electrospray Tandem Mass Spectrometry," Biochemical Pharmacology, 1995, vol. 49 (8), pp. 1099-1110.

Yeung B., et al., "Characterization of Viatmin D.Sub.3 Metabolites Using Continuous-Flow Fast Atom Bombardment Tandem Mass Spectrometry and High Performance Liquid Chromatography," Chromatographia, 1993, vol. 645 (1), pp. 115-123.

Yeung B., et al., "Derivatization of Vitamin D Metabolites for Analysis by Capillary HPLC-Tandem Mass Spectrometry," American Laboratory, Jul. 1994, vol. 26, pp. 12, 14-16.

Yeung B., et al., "Role of Mass Spectrometry in Vitamin D Research," Mass Spectrometry Reviews, May 1995, vol. 14 (3), pp. 179-194.

Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography A, 1999, vol. 854, pp. 23-35.

Fitzgerald R.L., "Declaration," 2019, pp. 1-51.

Rainbow S., et al., "The Analysis of Vitamin D Analogues by Atmospheric Pressure Ionization Coupled to Triple Quadrupole Mass Spectrometry," Applied Biosystems, pp. 1.

Shimada K., and Higashi T., "High-Performance Liquid Chromatography/Mass Spectrometry of Vitamin D Compounds Employing Derivatization With Cookson-Type Reagents," Bunseki Kagaku, Jan. 2002, vol. 51(7), pp. 487-493.

Vogeser M., "Liquid Chromatography-Tandem Mass Spectrometry—Application in the Clinical Laboratory," Clinical Chemistry and Laboratory Medicine, Feb. 2003, vol. 41(2), pp. 115-252.

Voyksner R.D., "Improvements in LC/Electrospray Ion Trap Mass Spectrometry Performance Using an Off-Axis Nebulizer," Analytical Chemistry, Apr. 1999, vol. 71(7), pp. 1441-1447.

Final Office Action dated Apr. 9, 2015 for U.S. Appl. No. 14/180,722, filed Feb. 14, 2014.

Final Office Action dated Sep. 12, 2012 for U.S. Appl. No. 13/327,650, filed Dec. 15, 2011.

(56) References Cited

OTHER PUBLICATIONS

Final Office Action dated Dec. 13, 2013 for U.S. Appl. No. 13/514,892, filed Jun. 8, 2012.
Final Office Action dated Dec. 17, 2010 for U.S. Appl. No. 11/946,765, filed Nov. 28, 2007.
Final Office Action dated Dec. 17, 2010 for U.S. Appl. No. 12/630,796, filed Dec. 3, 2009.
Final Office Action dated Jan. 25, 2011 for U.S. Appl. No. 12/001,076, filed Dec. 6, 2007.
Final Office Action dated Sep. 25, 2017 for U.S. Appl. No. 14/726,957, filed Jun. 1, 2015.
Final Office Action dated Aug. 27, 2014 for U.S. Appl. No. 14/053,423, filed Oct. 14, 2013.
Final Office Action dated Jun. 27, 2013 for U.S. Appl. No. 12/964,717, filed Dec. 9, 2010.
Final Office Action dated Oct. 27, 2010 for U.S. Appl. No. 12/001,076, filed Dec. 6, 2007.
Final Office Action dated Feb. 28, 2013 for U.S. Appl. No. 12/964,710, filed Dec. 9, 2010.
Final Office Action dated Oct. 29, 2019 for U.S. Appl. No. 15/194,009, filed Jun. 27, 2016.
Gao S., et al., "Sensitivity Enhancement in Liquid Chromatography/Atmospheric Pressure Ionization Mass Spectrometry Using Derivatization and Mobile Phase Additives," Journal of Chromatography B, 2005, vol. 825 (2), pp. 98-110.
Gentile F., et al., "Identification of Hormonogenic Tyrosines in Fragment 1218-1591 of Bovine Thyroglobulin by Mass Spectrometry. Hormonogenic Acceptor Tyr-1291 and Donor Tyr-1375," The Journal of Biological Chemistry, 1997, vol. 272 (1), pp. 639-646.
Grant R.P., et al., "Generic Serial and Parallel On-Line Direct-Injection Using Turbulent Flow Liquid Chromatography/tandem Mass Spectrometry," Rapid Communications in Mass Spectrometry, 2002, vol. 16 (18), pp. 1785-1792.
Guo T., et al., "Steroid Profiles Using Liquid Chromatography-Tandem Mass Spectrometry with Atmospheric Pressure Photoionization Source," Archives of Pathology & Laboratory Medicine, 2004, vol. 128 (4), pp. 469-475.
Guo-Zhong Ji, et al., "Clinical Test Diagnosis and Resolution" Jan. 2011, pp. 335-336.
Hagar A.F., et al., "Reversed-Phase Liquid Chromatographic Determination of Vitamin D in Milk," Journal of AOAC International, 1994, vol. 77 (4), pp. 1047-1051.
Hashizume T., et al., "Identification of Human UDP-Glucuronosyltransferases Catalyzing Hepatic 1a,25-Dihydroxyvitamin D3 Conjugation," Biochemical Pharmacology, 2008, vol. 75 (5), pp. 1240-1250.
Heudi O., et al., "Simultaneous Quantification of Vitamins A, D3 and E in Fortified Infant Formulae by Liquid Chromatography-Mass Spectrometry," Journal of Chromatography, 2004, vol. 1022 (1-2), pp. 115-123.
Higashi T., et al., "Application of 4-(4-Nitrophenyl)-1,2,4-triazoline-3,5-dione to Analysis of 25-Hydroxyvitamin D3 in Human Plasma by Liquid Chromatography/Electron Capture Atmospheric Pressure Chemical Ionization-Mass Spectrometry," Analytical Sciences, 2003, vol. 19 (6), pp. 941-943.
Higashi T., et al., "Characterization of New Conjugated Metabolites in Bile of Rats Administered 24, 25-Dihydroxyvitamin D3 and 25-Hydroxyvitamin D3," Steroids, 2000, vol. 65 (5), pp. 281-294.
Higashi T., et al., "Characterization of Urinary Metabolites of Vitamin D3 in Man under Physiological Conditions Using Liquid Chromatography-Tandem Mass Spectrometry," Journal of Pharmaceutical and Biomedical Analysis, 2002, vol. 29 (5), pp. 947-955.
Higashi T., et al., "Determination of 24, 25-Dihydroxyvitamin D3 in Human Plasma Using Liquid Chromatography-Mass Spectrometry after Derivatization with a Cookson-Type Reagent," Journal of Chromatography, 2001, vol. 15 (2), pp. 133-140.
Higashi T., et al., "Simultaneous Determination of 25-Hydroxyvitamin D2 and 25-Hydroxyvitamin D3 in Human Plasma by Liquid Chromatography-Tandem Mass Spectrometry Employing Derivatization with a Cookson-Type Reagent," Biological & Pharmaceutical Bulletin, Jul. 2001, vol. 24 (7), pp. 738-743. XP001207196.
Higashi T., et al., "Liquid Chromatography-Mass Spectrometric Method Combined With Derivatization for Determination of 1 Alpha-Hydroxyvitamin D (3) In Human Plasma," Journal of Chromatography B, 2002, vol. 772 (2), pp. 229-238.
Higashi T., et al., "Liquid Chromatography-Tandem Mass Spectrometric Method for the Determination of Salivary 25-Hydroxyvitamin D3: A Noninvasive Tool for the Assessment of Vitamin D Status," Analytical and Bioanalytical Chemistry, 2008, vol. 391 (1), pp. 229-238.
Higashi T., et al., "Usefulness of Derivatization in High-Performance Liquid Chromatography/Tandem Mass Spectrometry of Conjugated Vitamin D Metabolites," Analytical Sciences, 1999, vol. 15, pp. 619-623.
Higashi T., "Trace Determination of Steroids Causing Age-Related Diseases Using LC/MS Combined with Detection-Oriented Derivatization," Chemical & Pharmaceutical Bulletin, Nov. 2006, vol. 54 (11), pp. 1479-1485.
Hollis B.W., et al., "Solid Phase Extraction System for Vitamin D and Its Major Metabolites in Human Plasma," Journal of Chromatography, Sep. 1985, vol. 343(1), pp. 43-49.
Hoofnagle A.N., et al., "Quantification of Thyroglobulin, a Low-Abundance Serum Protein, by Immunoaffinity Peptide Enrichment and Tandem Mass Spectrometry," Clinical Chemistry, 2008, vol. 54 (11), pp. 1796-1804.
International Preliminary Report and Written Opinion on Patentability for Application No. PCT/US2010/059746, dated Jun. 12, 2012.
International Preliminary Report and Written Opinion on Patentability for Application No. PCT/US2010/059771, dated Jun. 12, 2012.
International Preliminary Report on Patentability for Application No. PCT/US2006/012539, dated Oct. 9, 2007.
International Preliminary Report on Patentability for Application No. PCT/US2008/084709, dated Jun. 1, 2010.
International Preliminary Report on Patentability for Application No. PCT/US2008/085435, dated Jun. 8, 2010.
International Preliminary Report on Patentability for Application No. PCT/US2010/056886, dated Jun. 5, 2012.
International Preliminary Report on Patentability for Application No. PCT/US2010/057627, dated Jun. 5, 2012.
International Preliminary Report on Patentability for Application No. PCT/US2010/059765, dated Jun. 12, 2012.
International Search Report and Written Opinion for Application No. PCT/US2010/056461, dated Jan. 26, 2011.
International Search Report and Written Opinion for Application No. PCT/US2010/057627, dated Jan. 27, 2011.
International Search Report and Written Opinion for Application No. PCT/US2010/059746, dated Feb. 8, 2011.
International Search Report and Written Opinion for Application No. PCT/US2010/059765, dated Feb. 7, 2011.
International Search Report and Written Opinion for Application No. PCT/US2013/60659, dated Dec. 23, 2013, 10 pages.
International Search Report for Application No. PCT/US08/85435, dated Apr. 22, 2009, 2 Pages.
International Search Report for Application No. PCT/US2006/012539, dated Jan. 4, 2007.
International Search Report for Application No. PCT/US2008/084709, dated Feb. 24, 2009.
International Search Report for Application No. PCT/US2010/056886, dated Jan. 14, 2011.
International Search Report for Application No. PCT/US2010/059771, dated Feb. 11, 2011.
Iwase H., "Determination of Vitamin D-2 in Emulsified Nutritional Supplements by Solid-Phase Extraction and Column-Switching High-Performance Liquid Chromatography with UV Detection," Journal of Chromatography A, Jul. 2000, vol. 881 (1-2), pp. 189-196.
Aberhart D. J., et al., "Studies on the Adduct of 4-Phenyl-1,2,4-Triazoline-3,5-Dione with Vitamin D3," Journal of Organic Chemistry, 1976, vol. 41 (12), pp. 2098-2102.

(56) References Cited

OTHER PUBLICATIONS

Adachi T., et al., "Determination of Vitamin D3 nad D2 in the Multi-Vitamin Tablets by High-Performance Liquid Chromatography/ Atmospheric Pressure Chemical Ionization Mass Spectrometry," Analytical Science, 1994, vol. 10, pp. 457-460.
Aguera A., et al., "One-Year Routine Application of a New Method Based on Liquid Chromatography-Tandem Mass Spectrometry to the Analysis of 16 Multiclass Pesticides in Vegetable Samples," Journal of Chromatography A, Aug. 2004, vol. 1045 (1-2), pp. 125-135.
Armas L.A., et al., "Vitamin D2 is Much Less Effective than Vitamin D3 in Humans," The Journal of Clinical Endocrinology & Metabolism, 2004, vol. 89 (11), pp. 5387-5391.
Aronov P., "Metabolic Profiling of Biologically Active Conjugated Dienes Using Diels-Alder Derivatization and Electrospray Ionization/ Tandem Mass Spectrometry", University of California, Davis, Dissertations, 2008, 122 pages.
Aronov P.A., et al., "Metabolic Profiling of Major Vitamin D Metabolites Using Diels-Alder Derivatization and Ultra-Performance Liquid Chromatography-Tandem Mass Spectrometry," Analytical and Bioanalytical Chemistry, 2008, vol. 391 (5), pp. 1917-1930.
Ascalone V., et al., "Stereospecific Determination of Amisulpride, a New Benzamide Derivative, In Human Plasma and Urine by Automated Solid-Phase Extraction and Liquid Chromatography on a Chiral Column Application to Pharmacokinetics," Journal of Chromatography B, 1996, vol. 676, pp. 95-105.
Asperger A., et al., "Trace Determination of Priority Pesticides in Water by Means of High-Speed On-Line Solid-Phase Extraction-Liquid Chromatography-Tandem Mass Spectrometry Using Turbulent-Flow Chromatography Columns for Enrichment and a Short Monolithic Column for Fast Liquid Chromatographic Separation," Journal of Chromatography A, Jun. 2002, vol. 960 (1-2), pp. 109-119.
Axelson M., "Liquid-Solid Extraction of Vitamin D3 Metabolites From Plasma for Analysis by HPLC, GC/MS and Protein Binding Techniques," Analytical Letters, 1985, vol. 18(B13), pp. 1607-1622.
Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.
Biemann K., "Mass Spectrometry of Peptides and Proteins," Annual Review of Biochemistry, 1992, vol. 61, pp. 977-1010.
Bourrel F., et al., "Immunoradiometric Assay of Thyroglobulin in Patients with Differentiated Thyroid Carcinomas: Need for Thyroglobulin Recovery Tests," Clinical Chemistry and Laboratory Medicine, 1998, vol. 36 (8), pp. 725-730.
Boyer F.O., et al., "Determination of Vitamins D2, D3, K1 and K3 and Some Hydroxy Metabolites of Vitamin D3 in Plasma Using a Continuous Clean-Up-Preconcentration Procedure Coupled On-Line with Liquid Chromatography-UV Detection," Analyst, 1999, vol. 124 (3), pp. 401-406.
Bunch D.R., et al., "Development and Validation of a Liquid Chromatography-Tandem Mass Spectrometry Assay for Serum 25-Hydroxy vitamin D2/D3 Using a Turbulent Flow Online Extraction Technology," Clinical Chemistry and Laboratory Medicine , 2009, vol. 47 (12), pp. 1565-1572.
Busch K.L., et al., "A Glossary for Mass Spectrometry," Mass Spectrometry, 2002, vol. 17 (65), pp. 526-534.
Capote P.F., et al., "Identification and Determination of Fat-Soluble Vitamins and Metabolites in Human Serum by Liquid Chromatography/ Triple Quadrupole Mass Spectrometry with Multiple Reaction Monitoring," Rapid Communications in Mass Spectrometry, 2007, vol. 21 (11), pp. 1745-1754.
Casetta B., et al., "Development of a Method for the Quantification of 1alpha,25(OH)2-Vitamin D3 in Serum by Liquid Chromatography Tandem Mass Spectrometry Without Derivatization," European Journal of Mass Spectrometry, 2010, vol. 16 (1), pp. 81-89.
Chen W.J., et al., "Induction of Apoptosis by Vitamin D2, Ergocalciferol, via Reactive Oxygen Generation, Glutathione Depletion, and Caspase Activation in Human Leukemia Cells," Journal of Food and Chemistry, 2008, vol. 56 (9), pp. 2996-3005.
Chen Y., et al., "Organic Mass Spectrometry Principles and Applications," Science Press, 2001, 6 pages.
Coldwell R.D., et al., "Mass Fragmentographic Assay for 25-Hydroxyvitamin D in Plasma Without Derivatization: Enhanced Sensitivity for Metabolites of Vitamins D2 and D3 After Pre-column Dehydration," Journal of Mass Spectrometry, 1995, vol. 30 (2), pp. 348-356.
Coldwell R.D., et al., "Measurement of Vitamins D2 and D3 and Seven Major Metabolites in a Single Sample of Human Plasma Using Gas Chromatography/Mass Spectrometry," Biomedical and Environmental Mass Spectrometry, 1988, vol. 16 (1-12), pp. 81-85.
Coldwell R.D., et al., "Stable Isotope-Labeled Vitamin D, Metabolites and Chemical Analogs: Synthesis and Use in Mass Spectrometric Studies," Steroids, 1990, vol. 55 (10), pp. 418-432.
Dabek J.T., et al., "Assay for Plasma 25-Hydroxyvitamin D2 and 25-Hydroxyvitamin D3 by "High-Performance" Liquid Chromatography," Clinical Chemistry, Aug. 1981, vol. 27(8), pp. 1346-1351.
Danaceau J.P., et al., "Quantitative Confirmation of Testosterone and Epitestosterone in Human Urine by LC/Q-ToF Mass Spectrometry for Doping Control," Journal of Mass Spectrometry, Jul. 2008, vol. 43 (7), pp. 993-1000.
Di Jeso B., et al., "Mixed-Disulfide Folding Intermediates between Thyroglobulin and Endoplasmic Reticulum Resident Oxidoreductases ERp57 and protein Disulfide Isomerase," Molecular and Cellular Biology, 2005, vol. 25 (22), pp. 9793-9805.
Doctoral Dissertation from the Central South University, "Study on Use of API-MS Ionization Law and LC-MS in Drug and Endogenous Substance Metabolism," Jun. 2006, 133 pages.
Dunn A.D., et al., "Tyrosine 130 is an Important Outer Ring Donor for Thyroxine Formation in Thyroglobulin," The Journal of Biological Chemistry, 1998, vol. 273 (39), pp. 25223-25229.
Dunn J.T., et al., "The Sites of Thyroid Hormone Formation in Rabbit Thyroglobulin," The Journal of Biological Chemistry, 1987, vol. 262 (35), pp. 16948-16952.
European Search Report for Application No. EP13185360, dated Jan. 22, 2014, 7 pages.
Examiner's Answer to Appeal Brief dated Sep. 17, 2018 for U.S. Appl. No. 14/267,014, filed May 1, 2014.
Examiner's Answer to Appeal Brief dated Jan. 9, 2014 for U.S. Appl. No. 12/964,717, filed Dec. 9, 2010.
Examiner's Answer to Appeal Brief dated Sep. 20, 2016 for U.S. Appl. No. 12/964,710, filed Dec. 9, 2010.
Extended European Search Report for Application No. 06749272.8, dated Feb. 2, 2009.
Extended European Search Report for Application No. 08853843.4, dated Dec. 22, 2010.
Extended European Search Report for Application No. 10836702.0, dated Oct. 2, 2013.
Extended European Search Report for Application No. 10836711.1, dated Nov. 14, 2013.
Extended European Search Report for Application No. 11184151.6, dated Dec. 1, 2011.
Extended European Search Report for Application No. 16154623.9, dated Apr. 12, 2016.
Extended European Search Report for Application No. EP17200516.7, dated Jan. 30, 2018, 8 pages.
Extended European Search Report for Application No. EP18194579.1, dated Dec. 5, 2018, 11 pages.
Extended European Search Report for Application No. EP18211011.4, dated Jun. 13, 2019, 8 pages.
Extended European Search Report for Application No. PCT/US2013/060659, dated Mar. 21, 2016, 11 pages.
Fiehn O., et al., "Mass Spectrometry: Quantitation" In: D Ganten and K Ruckpaul (Editors): "Encyclopedic Reference of Genomics and Proteomics in Molecular Medicine", Springer, 2006, pp. 1030-1034.
Final Office Action dated Aug. 1, 2016 for U.S. Appl. No. 14/726,957, filed Jun. 1, 2015.
Final Office Action dated Oct. 2, 2013 for U.S. Appl. No. 13/751,915, filed Jan. 28, 2013.

(56) References Cited

OTHER PUBLICATIONS

Final Office Action dated May 4, 2015 for U.S. Appl. No. 12/964,710, filed Dec. 9, 2010.
Final Office Action dated Nov. 4, 2019 for U.S. Appl. No. 14/639,834, filed Mar. 5, 2015.
Final Office Action dated Jan. 6, 2011 for U.S. Appl. No. 12/630,790, filed Dec. 3, 2009.
Final Office Action dated Sep. 6, 2012 for U.S. Appl. No. 13/198,620, filed Aug. 4, 2011.
Final Office Action dated Jun. 8, 2017 for U.S. Appl. No. 14/267,014, filed May 1, 2014.

* cited by examiner

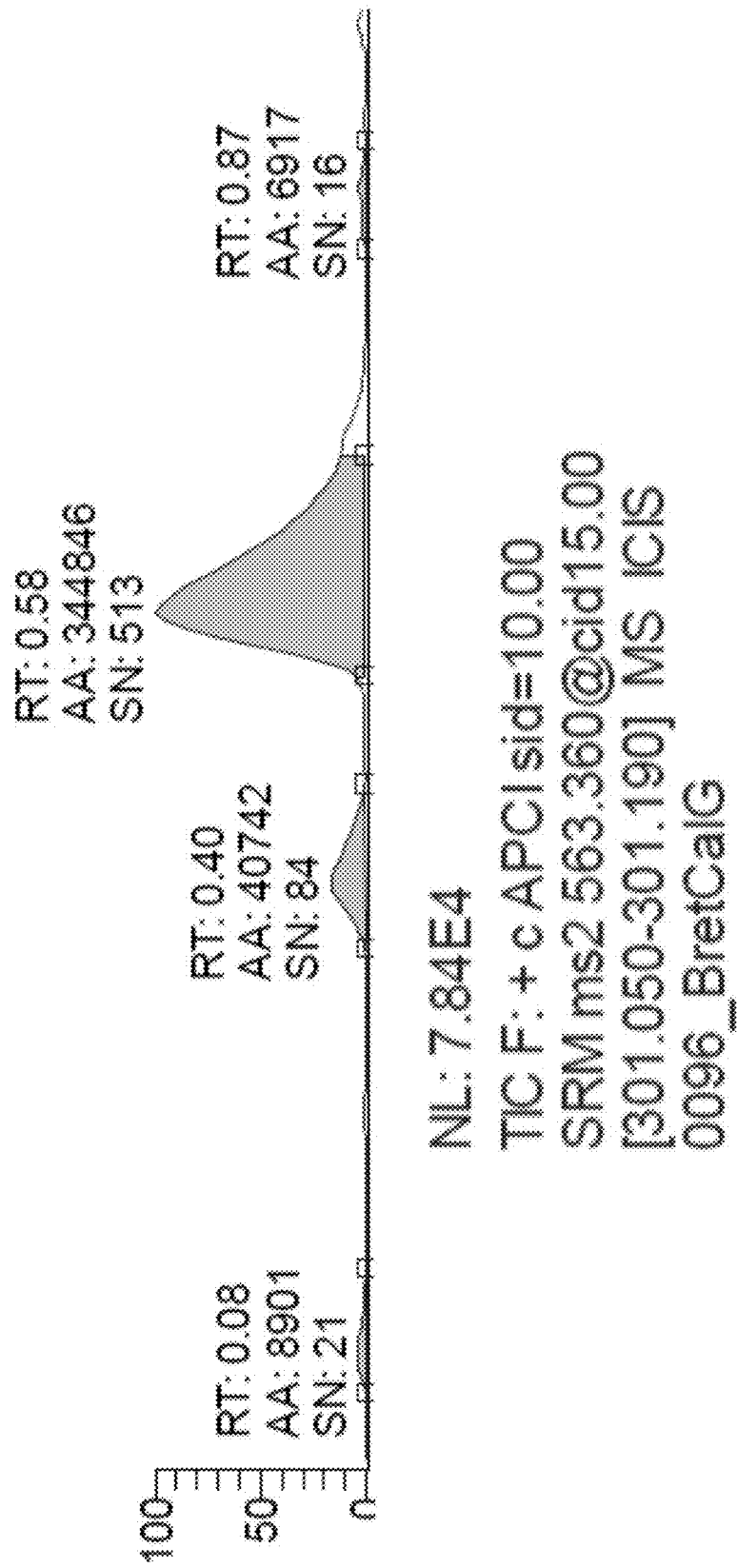

MASS SPECTROMETRIC DETERMINATION OF NON-DERIVATIZED, NON-METABOLIZED VITAMIN D

CROSS-REFERENCE TO RELATED PATENT APPLICATIONS

This application is a continuation of U.S. application Ser. No. 16/051,849, filed Aug. 1, 2018, now issued as U.S. Pat. No. 10,753,950, which is a continuation of U.S. application Ser. No. 12/964,710, filed Dec. 9, 2010, which claims priority to U.S. Provisional Application Ser. No. 61/285,938 (filed Dec. 11, 2009) and 61/285,943 (filed Dec. 11, 2009), both of which are incorporated herein by reference in their entirety including all figures and tables.

FIELD OF THE INVENTION

The invention relates to the quantitative measurement of non-metabolized vitamin D. In a particular aspect, the invention relates to methods for quantitative measurement of non-metabolized vitamin D by tandem mass spectrometry.

BACKGROUND OF THE INVENTION

Vitamin D is an essential nutrient with important physiological roles in the positive regulation of calcium ($Ca^{2+}$) homeostasis. Vitamin D can be made de novo in the skin by exposure to sunlight or it can be absorbed from the diet. There are two forms of vitamin D; vitamin $D_2$ (ergocalciferol) and vitamin $D_3$ (cholecalciferol). Vitamin $D_3$ is the form synthesized de novo by animals. It is also a common supplement added to milk products and certain food products produced in the United States. Both dietary and intrinsically synthesized vitamin $D_3$ must undergo metabolic activation to generate the bioactive metabolites. In humans, the initial step of vitamin $D_3$ activation occurs primarily in the liver and involves hydroxylation to form the intermediate metabolite 25-hydroxycholecalciferol (calcifediol; $25OHD_3$). Calcifediol is the major form of Vitamin $D_3$ in circulation. Circulating $25OHD_3$ is then converted by the kidney to form 1,25-dihydroxyvitamin $D_3$ (calcitriol; 1,25 $(OH)_2D_3$), which is generally believed to be the metabolite of Vitamin $D_3$ with the highest biological activity.

Vitamin $D_2$ is derived from fungal and plant sources. Many over-the-counter dietary supplements contain ergocalciferol (vitamin $D_2$) rather than cholecalciferol (vitamin $D_3$). Drisdol, the only high-potency prescription form of vitamin D available in the United States, is formulated with ergocalciferol. Vitamin $D_2$ undergoes a similar pathway of metabolic activation in humans as Vitamin $D_3$, forming the metabolites $25OHD_2$ and $1,25(OH)_2D_2$. Vitamin $D_2$ and vitamin $D_3$ have long been assumed to be biologically equivalent in humans, however recent reports suggest that there may be differences in the bioactivity and bioavailability of these two forms of vitamin D (Armas et. al., (2004) J. Clin. Endocrinol. Metab. 89:5387-5391).

Measurement of vitamin D, the inactive vitamin D precursor, is rare in clinical settings. Rather, serum levels of 25-hydroxyvitamin $D_3$, 25-hydroxyvitamin $D_2$, and total 25-hydroxyvitamin D ("25OHD") are useful indices of vitamin D nutritional status and the efficacy of certain vitamin D analogs. The measurement of 25OHD is commonly used in the diagnosis and management of disorders of calcium metabolism. In this respect, low levels of 25OHD are indicative of vitamin D deficiency associated with diseases such as hypocalcemia, hypophosphatemia, secondary hyperparathyroidism, elevated alkaline phosphatase, osteomalacia in adults and rickets in children. In patients suspected of vitamin D intoxication, elevated levels of 25OHD distinguishes this disorder from other disorders that cause hypercalcemia.

Measurement of $1,25(OH)_2D$ is also used in clinical settings. Certain disease states can be reflected by circulating levels of $1,25(OH)_2D$, for example kidney disease and kidney failure often result in low levels of $1,25(OH)_2D$. Elevated levels of $1,25(OH)_2D$ may be indicative of excess parathyroid hormone or can be indicative of certain diseases such as sarcoidosis or certain types of lymphomas.

Detection of vitamin D metabolites has been accomplished by radioimmunoassay with antibodies co-specific for $25OHD_2$ and $25OHD_3$. Because the current immunologically-based assays do not separately resolve $25OHD_2$ and $25OHD_3$, the source of any nutritional deficiency of vitamin D cannot be determined without resorting to other tests. Reports have been published that disclose methods for detecting specific vitamin D metabolites using mass spectrometry. In some of the reports, the vitamin D metabolites are derivatized prior to mass spectrometry, but in others, they are not. For example Holmquist, et al., U.S. patent application Ser. No. 11/946,765, filed Dec. 28, 2007; Yeung B, et al., J Chromatogr. 1993, 645(1):115-23; Higashi T, et al., Steroids. 2000, 65(5):281-94; Higashi T, et al., Biol Pharm Bull. 2001, 24(7):738-43; Higashi T, et al., J Pharm Biomed Anal. 2002, 29(5):947-55; Higashi T, et al., Anal. Biochanal Chem, 2008, 391:229-38; and Aronov, et al., Anal Bioanal Chem, 2008, 391:1917-30 disclose methods for detecting various vitamin D metabolites by derivatizing the metabolites prior to mass spectrometry. Methods to detect underivatized vitamin D metabolites are reported in Clarke, et al., in U.S. patent application Ser. No. 11/101,166, filed Apr. 6, 2005, and Ser. No. 11/386,215, filed Mar. 21, 2006, and Singh, et al., in U.S. patent application Ser. No. 10/977,121, filed Oct. 24, 2004. Reports have also been published that disclose derivatization of vitamin $D_3$ with Cookson-type reagents, specifically 4-phenyl-1,2,4-triazoline-3,5-dione (PTAD) and 4-[2-(6,7-dimethoxy-4-methyl-3-oxo-3,4-dihydroquinoxalyl)ethyl]-1,2,4-triazoline-3,5-dione (DMEQ-TAD). See Aberhart, J, et al., J. Org. Chem. 1976, 41(12): 2098-2102, and Kamao, M, et al., J Chromatogr. B 2007, 859:192-200.

SUMMARY OF THE INVENTION

The present invention provides methods for detecting the amount of one or more (non-metabolized) forms of vitamin D in a sample by mass spectrometry, including tandem mass spectrometry. In one aspect, vitamin D from the sample is derivatized prior to analysis by mass spectrometry. In a second aspect, vitamin D from the sample is not derivatized prior to analysis by mass spectrometry.

In some embodiments of the first aspect, the methods include the steps of: (i) subjecting Cookson-type-derivatized vitamin D in the sample to an ionization source under conditions suitable to generate one or more precursor ions detectable by mass spectrometry; (ii) fragmenting at least one of said precursor ions to generate one or more fragment ions detectable by mass spectrometry; (iii) determining the amount of one or more of the precursor and fragment ions by mass spectrometry; and (iv) relating the amount of ions determined in step (iii) to the amount of a vitamin D in the sample. In these methods, the sample is subjected to a Cookson-type derivatization reagent under conditions sufficient to generate Cookson-type-derivatized vitamin D prior to step (i). In some embodiments, the Cookson-type-derivatized-vitamin D is subjected to an extraction column and an analytical column prior to ionization. In related embodiments, the analytical column may be a high performance liquid chromatography (HPLC) column.

In some embodiments of the first aspect, the methods include the steps of: (i) subjecting the sample to turbulent flow liquid chromatography (TFLC); (ii) subjecting Cookson-type-derivatized vitamin D from the sample an ionization source under conditions suitable to generate one or more ions detectable by mass spectrometry; (iii) determining the amount of one or more of the Cookson-type-derivatized vitamin D ions by mass spectrometry; and (iv) relating the amount of Cookson-type-derivatized vitamin D ions determined in step (iii) to the amount of a vitamin D in the sample. In these embodiments, the sample is subjected to a Cookson-type derivatizing reagent under conditions sufficient to generate Cookson-type-derivatized vitamin D in the sample prior to step (i). In some embodiments, the sample is subjected to high performance liquid chromatography (HPLC) after step (i) but prior to step (ii).

In some embodiments, the Cookson-type derivatizing reagent is 4-phenyl-1,2,4-triazoline-3,5-dione (PTAD). In some of these embodiments, the one or more precursor ions comprise one or more ions selected from the group consisting of ions with a mass/charge ratio (m/z) of 572.4±0.5 and 560.4±0.5. In some of these embodiments, one or more fragment ions comprise an ion with a mass/charge ratio (m/z) of 298.1±0.5.

In embodiments where vitamin D comprises vitamin $D_2$, one or more Cookson-type-derivatized vitamin D ions may comprise a precursor ion with a mass/charge ratio (m/z) of 572.3±0.5 and a fragment ion with a mass/charge ratio (m/z) of 298.1±0.5. In embodiments where vitamin D comprises vitamin $D_3$, one or more Cookson-type-derivatized vitamin D ions may comprise a precursor ion with a mass/charge ratio (m/z) of 560.3±0.5 and a fragment ion with a mass/charge ratio (m/z) of 298.1±0.5. In embodiments where vitamin D comprises vitamin $D_2$ and vitamin $D_3$, one or more precursor ions may comprise a vitamin $D_2$ precursor ion with a mass/charge ratio (m/z) of 572.4±0.5 and a vitamin $D_3$ precursor ion with a m/z of 560.4±0.5; and one or more fragment ions may comprise a vitamin $D_2$ fragment ion with a m/z of 298.1±0.5 and a vitamin $D_3$ fragment ion with a m/z of 298.1±0.5.

In some embodiments of the second aspect, the invention provides methods for determining the amount of vitamin D in a sample by tandem mass spectrometry without ionization and detection of derivatized vitamin D. In some embodiments, the vitamin D comprises vitamin $D_2$; these methods include the steps of: subjecting vitamin $D_2$ from a sample to an ionization source under conditions suitable to generate one or more precursor ions detectable by mass spectrometry selected from the group consisting of ions with a mass to charge ratio (m/z) of 397.2±0.5 or 379.2±0.5; fragmenting at least one of said precursor ions to generate one or more fragment ions detectable by mass spectrometry; (iii) determining the amount of one or more of the ions generated in steps (i) and (ii) by mass spectrometry; and (iv) relating the presence of vitamin $D_2$ ions determined in step (iii) to the presence of vitamin $D_2$ in the sample. In these methods, if the fragmented precursor ions comprise an ion with m/z of 397.2±0.5, the fragment ions comprise one or more ions selected from the group consisting of ions with m/z of 159.0±0.5, 146.9±0.5, 133.1±0.5, and 121.0±0.5. In these methods, if the fragmented precursor ions comprise an ion with m/z of 379.2±0.5, the fragment ions comprise one or more ions selected from the group consisting of ions with m/z of 283.2±0.5, 187.3±0.5, 175.2±0.5, and 159.0±0.5. In some embodiments, vitamin $D_2$ from the sample may be subjected to an extraction column, such as a solid phase extraction (SPE) column or a turbulent flow liquid chromatography (THLC) column, prior to ionization. In some embodiments, vitamin $D_2$ from the sample is further subjected to an analytical column, such as a high performance liquid chromatography (HPLC) column, prior to ionization.

In other embodiments of the second aspect, vitamin D comprises vitamin $D_3$; these methods include the steps of: (i) subjecting vitamin $D_3$ from a sample to an ionization source under conditions suitable to generate one or more precursor ions detectable by mass spectrometry selected from the group consisting of ions with a mass to charge ratio (m/z) of 385.2±0.5 or 367.2±0.5; (ii) fragmenting at least one of the precursor ions to generate one or more fragment ions detectable by mass spectrometry; (iii) determining the amount of one or more of the ions generated in steps (i) and (ii) by mass spectrometry; and (iv) relating the presence of vitamin $D_3$ ions determined in step (iii) to the presence of vitamin $D_3$ in the sample. In these methods, if the fragmented precursor ions comprise an ion with m/z of 385.2±0.5, the fragment ions comprise one or more ions selected from the group consisting of ions with m/z of 159.0±0.5, 147.0±0.5, 133.1±0.5, and 107.1±0.5. If the fragmented precursor ions comprise an ion with m/z of 367.2±0.5, the fragment ions comprise one or more ions selected from the group consisting of ions with m/z of 172.2±0.5, 145.0±0.5, and 119.1±0.5. In some embodiments, vitamin $D_3$ from the sample may be subjected to an extraction column, such as a solid phase extraction (SPE) column or a turbulent flow liquid chromatography (THLC) column, prior to ionization. In some embodiments, vitamin $D_3$ from the sample is further subjected to an analytical column, such as a high performance liquid chromatography (HPLC) column, prior to ionization.

In the methods described herein, mass spectrometry may be tandem mass spectrometry. In embodiments utilizing tandem mass spectrometry, tandem mass spectrometry may be conducted by any method known in the art, including for example, multiple reaction monitoring, precursor ion scanning, or product ion scanning.

In embodiments which utilize an extraction column, the extraction column may be a solid phase extraction (SPE) column; such as a turbulent flow liquid chromatography (TFLC) column. In some embodiments, which utilize two or more of an extraction column, an analytical column, and an ionization source, the utilized components may be connected in an on-line fashion to allow for automated sample processing and analysis.

Cookson-type derivatizing reagents useful for certain embodiments may be selected from the group consisting of 4-phenyl-1,2,4-triazoline-3,5-dione (PTAD), 4-methyl-1,2,4-triazoline-3,5-dione (MTAD), 4-[2-(6,7-dimethoxy-4-methyl-3-oxo-3,4-dihydroquinoxalyl)ethyl]-1,2,4-triazoline-3,5-dione (DMEQTAD), 4-(4-nitrophenyl)-1,2,4-triazoline-3,5-dione (NPTAD), and 4-ferrocenylmethyl-1,2,4-triazoline-3,5-dione (FMTAD), and isotopically labeled variants thereof. In preferred embodiments, the Cookson-type derivatizing reagent is 4-phenyl-1,2,4-triazoline-3,5-dione (PTAD) or an isotopically labeled variant thereof. In certain preferred embodiments, the Cookson-type derivatizing reagent is 4-phenyl-1,2,4-triazoline-3,5-dione (PTAD) or an isotopically labeled variant thereof.

As used herein, the term "vitamin D" refers to any one or more naturally occurring or synthetic analog of vitamin D which are non-metabolized. This is in contrast to vitamin D metabolites which are identified by specific chemical modification (e.g., 25-hydroxyvitamin D and 1α,25-dihydroxyvitamin D) which occurs during metabolism. Non-metabolized vitamin D may also be referred to as "nutritional" vitamin D to distinguish from metabolized forms. Reference to vitamin D without specifying a metabolized form is a reference to non-metabolized forms.

As used herein, "derivatizing" means reacting two molecules to form a new molecule. Thus, a derivatizing agent is an agent that may be reacted with another substance to derivatize the substance. For example, 4-phenyl-1,2,4-triazoline-3,5-dione (PTAD) is a derivatizing reagent that may be reacted with vitamin D to form a PTAD-derivatized vitamin D.

As used here, the names of derivatized forms vitamin D include an indication as to the nature of derivatization. For example, the PTAD derivative of vitamin $D_2$ is indicated as PTAD-vitamin $D_2$ (or PTAD-derivatized vitamin $D_2$).

As used herein, a "Cookson-type derivatizing agent" is a 4-substituted 1,2,4-triazoline-3,5-dione compound. Exemplary Cookson-type derivatizing agents include 4-phenyl-1,2,4-triazoline-3,5-dione (PTAD), 4-methyl-1,2,4-triazoline-3,5-dione (MTAD), 4-[2-(6,7-dimethoxy-4-methyl-3-oxo-3,4-dihydroquinoxalyl)ethyl]-1,2,4-triazoline-3,5-dione (DMEQTAD), 4-(4-nitrophenyl)-1,2,4-triazoline-3,5-dione (NPTAD), and 4-ferrocenylmethyl-1,2,4-triazoline-3,5-dione (FMTAD). Additionally, isotopically labeled variants of Cookson-type derivatizing agents may be used in some embodiments. For example, the $^{13}C_6$-PTAD isotopic variant is 6 mass units heavier than normal PTAD and may be used in some embodiments. Derivatization of vitamin D metabolites by Cookson-type reagents can be conducted by any appropriate method. See, e.g., Holmquist, et al., U.S. patent application Ser. No. 11/946,765, filed Dec. 28, 2007; Yeung B, et al., J Chromatogr. 1993, 645(1):115-23; Higashi T, et al., Steroids. 2000, 65(5):281-94; Higashi T, et al., Biol Pharm Bull. 2001, 24(7):738-43; Higashi T, et al., J Pharm Biomed Anal. 2002, 29(5):947-55; Higashi T, et al., Anal. Biochanal Chem, 2008, 391:229-38; and Aronov, et al., Anal Bioanal Chem, 2008, 391:1917-30.

Vitamin D may refer to one or more forms of vitamin D, such as vitamin $D_2$ and/or vitamin $D_3$. In embodiments were a sample comprises a plurality of vitamin D forms, the plurality of vitamin D forms may be ionized simultaneously. For example, in some embodiments, the amounts of vitamin $D_2$ and vitamin $D_3$ are determined in the same sample. In these embodiments, (derivatized or underivatized) vitamin $D_2$ and vitamin $D_3$ may be ionized simultaneously.

The term "simultaneous" as applied to simultaneously detecting the amount of two or more analytes from a sample means acquiring data reflective of the amount of the two or more analytes in the sample from the same sample injection. The data for each analyte may be acquired sequentially or in parallel, depending on the instrumental techniques employed. For example, a single sample containing two analytes may be injected into a HPLC column, which may then elute each analyte one after the other, resulting in introduction of the analytes into a mass spectrometer sequentially. Determining the amount of each of these two analytes is simultaneous for the purposes herein, as both analytes result from the same sample injection into the HPLC.

Vitamin D may be found in the circulation of an animal and/or may be generated by a biological organism, such as an animal. As such, samples may be obtained, for example, from a patient; that is, a living person, male or female, presenting oneself in a clinical setting for diagnosis, prognosis, or treatment of a disease or condition. Preferred samples may be biological samples; particularly biological fluid samples such as serum or plasma. The methods presented herein may be used to determine the amount of vitamin D present in a sample when taken from the human.

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI), laser diode thermal desorption (LDTD), or electrospray ionization (ESI), may be used in embodiments of the present invention. In certain preferred embodiments, vitamin D metabolites are measured using APCI or LDTD in positive ion mode.

In preferred embodiments, one or more separately detectable internal standards are provided in the sample, the amount of which are also determined in the sample. In these embodiments, all or a portion of both the analyte(s) of interest and the internal standard(s) present in the sample are ionized to produce a plurality of ions detectable in a mass spectrometer, and one or more ions produced from each are detected by mass spectrometry. Preferably, the internal standard(s) are one or more of vitamin $D_2$-[6, 19, 19]-$^2H_3$, vitamin $D_2$-[26, 26, 26, 27, 27, 27]-$^2H_6$, vitamin $D_3$-[6, 19, 19]-$^2H_3$, and vitamin $D_3$-[26, 26, 26, 27, 27, 27]-$^2H_6$.

One or more separately detectable internal standards may be provided in the sample prior to treatment with a Cookson-type derivatizing reagent (if applicable), or any purification of the analyte(s) from the sample. In these embodiments, the one or more internal standards may undergo derivatization and/or purification along with the endogenous vitamin D, in which case ions of the derivatized and/or purified internal standards are detected by mass spectrometry. In these embodiments, the presence or amount of ions generated from the analyte of interest may be related to the presence or amount of analyte of interest in the sample. In some embodiments, the internal standards may be isotopically labeled versions of vitamin D, such as vitamin $D_2$-[6, 19, 19]-$^2H_3$, vitamin $D_2$-[26, 26, 26, 27, 27, 27]-$^2H_6$, vitamin $D_3$-[6, 19, 19]-$^2H_3$, and vitamin $D_3$-[26, 26, 26, 27, 27, 27]-$^2H_6$.

Ions detectable in a mass spectrometer may be generated for each of the exemplary internal standards listed above. Exemplary spectra generated for several exemplary internal standards are discussed in Examples 8 and 9, and shown in FIGS. 6-7, 9-10, 12-13, and 15-16.

As used herein, an "isotopic label" produces a mass shift in the labeled molecule relative to the unlabeled molecule when analyzed by mass spectrometric techniques. Examples of suitable labels include deuterium ($^2H$), $^{13}C$, and $^{15}N$. For example, vitamin $D_2$-[6, 19, 19]-$^2H_3$ and vitamin $D_3$-[6, 19, 19]-$^2H_3$ has masses of about 3 mass units higher than vitamin $D_2$ and vitamin $D_3$, respectively. The isotopic label can be incorporated at one or more positions in the molecule and one or more kinds of isotopic labels can be used on the same isotopically labeled molecule.

In other embodiments, the amount of vitamin D ion or ions may be determined by comparison to one or more external reference standards. Exemplary external reference standards include blank plasma or serum spiked with one or more of vitamin $D_2$-[6, 19, 19]-$^2H_3$, vitamin $D_2$-[26, 26, 26, 27, 27, 27]-$^2H_6$, vitamin $D_3$-[6, 19, 19]-$^2H_3$, and vitamin $D_3$-[26, 26, 26, 27, 27, 27]-$^2H_6$. External standards typically will undergo the same treatment and analysis as any other sample to be analyzed, including treatment with one or more Cookson-type reagents prior to mass spectrometry in embodiments wherein derivatized vitamin D is detected.

In certain embodiments, the lower limit of quantitation (LLOQ) of vitamin $D_2$ and vitamin $D_3$ are less than 10 ng/mL; preferably less than 5 ng/mL; preferably less than 2 ng/mL.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest.

Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm.

As used herein, the term "analytical column" refers to a chromatography column having sufficient chromatographic plates to effect a separation of materials in a sample that elute from the column sufficient to allow a determination of the presence or amount of an analyte. In a preferred embodiment the analytical column contains particles of about 5 µm in diameter. Such columns are often distinguished from "extraction columns", which have the general purpose of separating or extracting retained material from non-retained materials in order to obtain a purified sample for further analysis.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to a form of ionization where the mechanism for the ionization of molecule M is photon absorption and electron ejection to form the molecular ion M+. Because the energy of the absorbed photon is typically just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "desorption" refers to the removal of an analyte from a surface and/or the entry of an analyte into a gaseous phase. Laser diode thermal desorption (LDTD) is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample may then be drawn into an ionization source, where the gas phase sample is ionized in preparation for analysis in the mass spectrometer. When using LDTD, ionization of the gas phase sample may be accomplished by any suitable technique known in the art, such as by ionization with a corona discharge (for example by APCI).

As used herein, the term "field desorption" refers to methods in which a non-volatile test sample is placed on an ionization surface, and an intense electric field is used to generate analyte ions.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 80% to 120%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 1C shows an exemplary chromatogram for PTAD-vitamin $D_3$-[6, 19, 19]-$^2H_3$ (internal standard). Details are discussed in Example 3.

DETAILED DESCRIPTION OF THE INVENTION

Figure 1A:
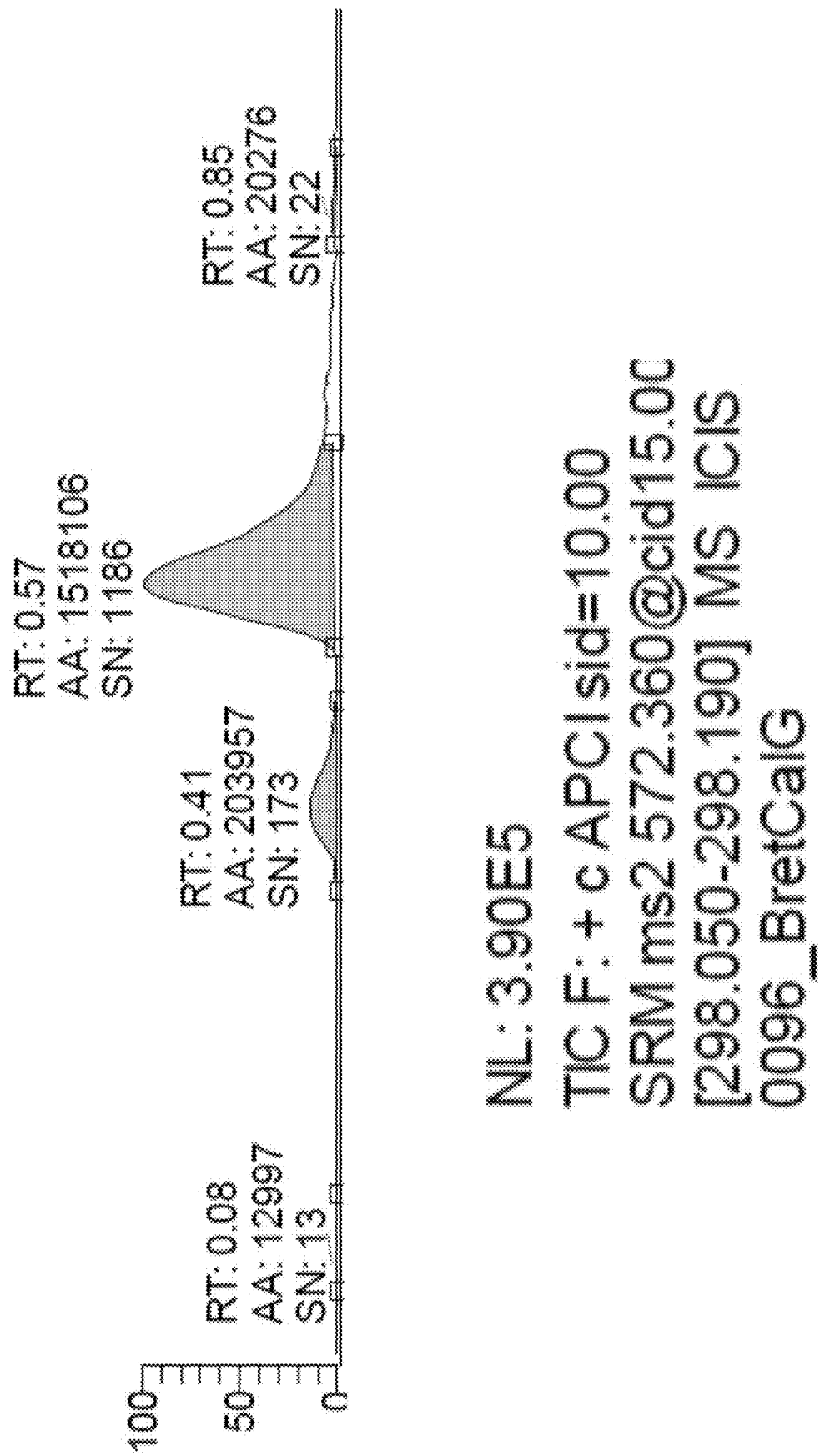
FIG. 1A shows an exemplary chromatogram for PTAD-vitamin $D_2$.

Methods are described for measuring vitamin D in a sample. More specifically, mass spectrometric methods are described for detecting and quantifying vitamin D in a sample. The methods may utilize Cookson-type reagents, such as PTAD, to generate derivatized vitamin D. However, in some methods, no derivatizing agent is used, and underivatized vitamin $D_2$ and/or vitamin $D_3$ are detected by mass spectrometry.

The methods may use an extraction chromatography technique, such as turbulent flow liquid chromatography (TFLC), to perform a purification of underivatized or derivatized vitamin $D_2$ and/or vitamin $D_3$, combined with methods of mass spectrometry (MS), thereby providing a high-throughput assay system for detecting and quantifying vitamin $D_2$ and/or vitamin $D_3$ in a sample. Alternatively, in some methods, no chromatography, including extraction chromatography, is necessary for sample analysis. In these methods, the underivatized or derivatized vitamin $D_2$ and/or vitamin $D_3$ is ionized with LDTD. Preferred embodiments are particularly well suited for application in large clinical laboratories for automated vitamin D quantification.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma (including EDTA and heparin plasma) and serum; most preferably serum. Such samples may be obtained, for example, from a patient; that is, a living person, male or female, presenting oneself in a clinical setting for diagnosis, prognosis, or treatment of a disease or condition.

The present invention also contemplates kits for a vitamin D quantitation assay. A kit for a vitamin D quantitation assay may include a kit comprising the compositions provided herein. For example, a kit may include packaging material and measured amounts of a Cookson-type reagent and an isotopically labeled internal standard, in amounts sufficient for at least one assay. Typically, the kits will also include instructions recorded in a tangible form (e.g., contained on paper or an electronic medium) for using the packaged reagents for use in a vitamin D quantitation assay.

Calibration and QC pools for use in embodiments of the present invention are preferably prepared using a matrix similar to the intended sample matrix.

Sample Preparation for Mass Spectrometric Analysis

In preparation for mass spectrometric analysis, vitamin D may be enriched relative to one or more other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving vitamin D in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, samples, such as plasma or serum, may be purified by a hybrid protein precipitation/ liquid-liquid extraction method. In these embodiments, a sample is mixed with methanol, ethyl acetate, and water, and the resulting mixture is vortexed and centrifuged. The resulting supernatant is removed, dried to completion and reconstituted in acetonitrile. The purified vitamin D may then be derivatized with any Cookson-type reagent, preferably PTAD or an isotopically labeled variant thereof.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with derivatized vitamin D. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded, cyano bonded surface, or highly pure silica surface.

Alkyl bonded surfaces may include C-4, C-8, C-12, or C-18 bonded alkyl groups. In preferred embodiments, the column is a highly pure silica column (such as a Thermo Hypersil Gold Aq column). The chromatographic column includes an inlet port for receiving a sample and an outlet port for discharging an effluent that includes the fractionated sample. The sample may be supplied to the inlet port directly, or from an extraction column, such as an on-line SPE cartridge or a TFLC extraction column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with an alkyl bonded analytical column chromatographic system. In certain preferred embodiments, a highly pure silica column (such as a Thermo Hypersil Gold Aq column) is used. In certain preferred embodiments, HPLC and/or TFLC are performed using HPLC Grade water as mobile phase A and HPLC Grade ethanol as mobile phase B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, an extraction column may be used for purification of vitamin D metabolites prior to mass spectrometry. In such embodiments, samples may be extracted using a extraction column which captures the analyte, then eluted and chromatographed on a second extraction column or on an analytical HPLC column prior to ionization. For example, sample extraction with a TFLC extraction column may be accomplished with a large particle size (50 μm) packed column. Sample eluted off of this column may then be transferred to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, protein precipitation is accomplished with a hybrid protein precipitation/liquid-liquid extraction method which includes methanol protein precipitation and ethyl acetate/water extraction from serum. The resulting vitamin D metabolites may be derivatized prior to being subjected to an extraction column. Preferably, the hybrid protein precipitation/liquid-liquid extraction method and the extraction column are connected in an on-line fashion. In preferred embodiments, the extraction column is a C-8 extraction column, such as a Cohesive Technologies $C_8XL$ online extraction column (50 μm particle size, 0.5×50 mm) or equivalent. The eluent from the extraction column may then be applied to an analytical LC column, such as a HPLC column in an on-line fashion, prior to mass spectrometric analysis. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, derivatized vitamin D may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

Derivatized vitamin D may be ionized in positive or negative mode. In preferred embodiments, derivatized vitamin D is ionized by APCI or LDTD in positive ion mode.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of vitamin D. Methods of generating and using such standard curves are well known in the art and one of ordinary skill is capable of selecting an appropriate internal standard. For example, in preferred embodiments one or more isotopically labeled vitamin D (e.g., vitamin $D_2$-[6, 19, 19]-$^2H_3$ and vitamin $D_3$-[6, 19, 19]-$^2H_3$) may be used as internal standards. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some preferred embodiments, vitamin D in a sample is detected and/or quantified using MS/MS as follows. The samples are first purified by protein precipitation or a hybrid protein precipitation/liquid-liquid extraction. Then, vitamin D in the purified sample is optionally derivatized with a Cookson-type reagent, such as PTAD. The purified samples are then subjected to liquid chromatography, preferably on an extraction column (such as a TFLC column) followed by an analytical column (such as a HPLC column); the flow of liquid solvent from a chromatographic column enters the nebulizer interface of an MS/MS analyzer; and the solvent/analyte mixture is converted to vapor in the heated charged tubing of the interface. The analyte(s) (e.g., derivatized or underivatized vitamin D) contained in the solvent, are ionized by applying a large voltage to the solvent/analyte mixture. As the analytes exit the charged tubing of the interface, the solvent/analyte mixture nebulizes and the solvent evaporates, leaving analyte ions. The analyte ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for ions with the mass to charge ratios of interest. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where derivatized or underivatized vitamin D fragment ions are selected while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of a derivatized vitamin D that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of vitamin D. As described above, the relative abundance of a given ion may be converted into an absolute amount of the original analyte using calibration standard curves based on peaks of one or more ions of an internal molecular standard.

EXAMPLES

Example 1: Hybrid Protein Precipitation/Liquid-Liquid Extraction and Cookson-type Derivatization The following automated hybrid protein precipitation/liquid-liquid extraction technique was conducted on patient serum samples. Gel Barrier Serum (i.e., serum collected in Serum Separator Tubes) as well as EDTA plasma and Heparin Plasma have also been established as acceptable for this assay.

A Perkin-Elmer Janus robot and a TomTec Quadra Tower robot was used to automate the following procedure. For each sample, 50 μL of serum was added to a well of a 96 well plate. Then 25 μL of internal standard cocktail (containing isotopically labeled vitamin $D_3$-[6, 19, 19]-$^2H_3$) was added to each well, and the plate vortexed. Then 75 μL of methanol was added, followed by additional vortexing. 300 μL of ethyl acetate and 75 μL of water was then added, followed by additional vortexing, centrifugation, and transfer of the resulting supernatant to a new 96-well plate.

The transferred liquid in the second 96-well plate was dried to completion under a flowing nitrogen gas manifold. Derivatization was accomplished by adding 100 μL of a 0.1 mg/mL solution of the Cookson-type derivatization agent PTAD in acetonitrile to each well. The derivatization reaction was allowed to proceed for approximately one hour, and was quenched by adding 100 μL of water to the reaction mixture.

Example 2: Extraction of Vitamin D with Liquid Chromatography

Sample injection was performed with a Cohesive Technologies Aria TX-4 TFLC system using Aria OS V 1.5.1 or newer software.

The TFLC system automatically injected an aliquot of the above prepared samples into a Cohesive Technologies C8XL online extraction column (50 μm particle size, 005×50 mm, from Cohesive Technologies, Inc.) packed with large particles. The samples were loaded at a high flow rate to create turbulence inside the extraction column. This turbulence ensured optimized binding of derivatized vitamin D to the large particles in the column and the passage of excess derivatizing reagent and debris to waste.

Following loading, the sample was eluted off to the analytical column, a Thermo Hypersil Gold Aq analytical column (5 μm particle size, 50×2.1 mm), with a water/ethanol elution gradient. The HPLC gradient was applied to the analytical column, to separate vitamin D from other analytes contained in the sample. Mobile phase A was water and mobile phase B was ethanol. The HPLC gradient started with a 35% organic gradient which was ramped to 99% in approximately 65 seconds.

Example 3: Detection and Quantitation of Derivatized Vitamin D by MS/MS

MS/MS was performed on the above generated samples using a Finnigan TSQ Quantum Ultra MS/MS system (Thermo Electron Corporation). The following software programs, all from Thermo Electron, were used in the Examples described herein: Quantum Tune Master V 1.5 or newer, Xcalibur V 2.07 or newer, LCQuan V 2.56 (Thermo Finnigan) or newer, and ARIA OS v1.5.1 (Cohesive Technologies) or newer. Liquid solvent/analyte exiting the analytical column flowed to the nebulizer interface of the MS/MS analyzer. The solvent/analyte mixture was converted to vapor in the tubing of the interface. Analytes in the nebulized solvent were ionized by APCI.

Ions passed to the first quadrupole (Q1), which selected vitamin $D_2$ and vitamin $D_3$ precursor ions with a mass-to-charge ratio of 572.3±0.5 m/z and 560.3±0.5 m/z, respectively. Ions entering quadrupole 2 (Q2) collided with argon gas to generate ion fragments, which were passed to quadrupole 3 (Q3) for further selection. Mass spectrometer settings are shown in Table 1. Simultaneously, the same process using isotope dilution mass spectrometry was carried out with internal standard, vitamin $D_3$-[6, 19, 19]-$^2H_3$. The mass transitions used for detection and quantitation during validation on positive polarity and at the indicated collision energies are shown in Table 2.

TABLE 1

Mass Spectrometer Settings for Detection of PTAD-vitamin $D_2$, PTAD-vitamin $D_3$, and vitamin $D_3$-[6, 19, 19]-$^2H_3$ (internal standard) (Positive Polarity)
Mass Spectrometric Instrument Settings

| | |
|---|---|
| Discharge Current | 4.0 μA |
| Vaporizer Temperature | 300° C. |
| Sheath Gas Pressure | 15 |
| Ion Sweep Gas Pressure | 0.0 |
| Aux Gas Pressure | 5 |
| Capillary Temperature | 300° C. |
| Skimmer Offset | −10 V |
| Collision Pressure | 1.5 mTorr |
| Collision Cell Energy | 15 V |

TABLE 2

Mass Transitions for PTAD derivatized vitamin $D_2$, vitamin $D_3$, and vitamin $D_3$-[6, 19, 19]-$^2H_3$ (internal standard) (Positive Polarity)

| Analyte | Precursor Ion (m/z) | Product Ions (m/z) |
|---|---|---|
| PTAD-vitamin $D_2$ | 572.3 ± 0.5 | 298.1 ± 0.5 |
| PTAD-vitamin $D_3$ | 560.3 ± 0.5 | 298.1 ± 0.5 |
| PTAD-vitamin $D_3$-[6, 19, 19]-$^2H_3$ | 563.3 ± 0.5 | 301.1 ± 0.5 |

Figure 1B:
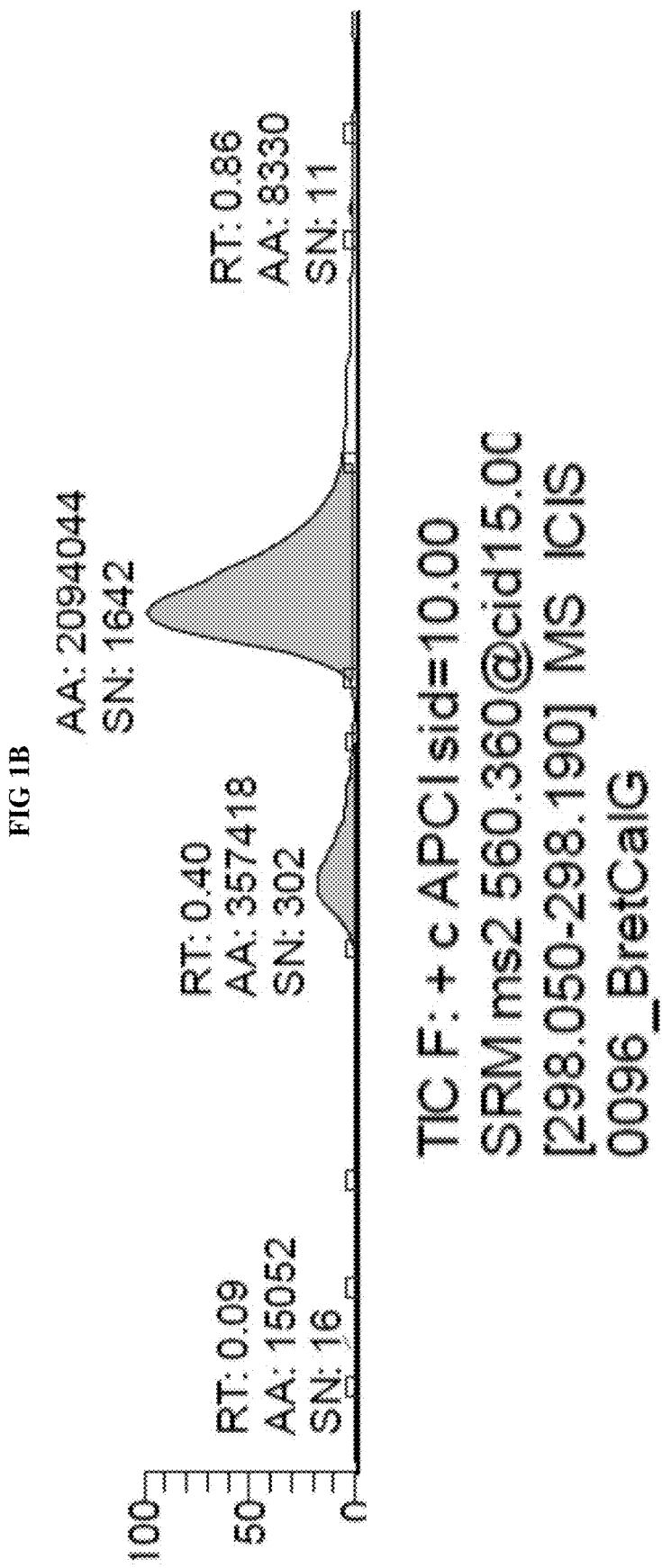
FIG. 1B shows an exemplary chromatogram for PTAD-vitamin $D_3$.

Exemplary chromatograms for PTAD-vitamin $D_2$, PTAD-vitamin $D_3$, PTAD-vitamin $D_3$-[6, 19, 19]-$^2H_3$ (internal standard), are shown in FIGS. 1A, 1B, and 1C, respectively.

Figure 2A:
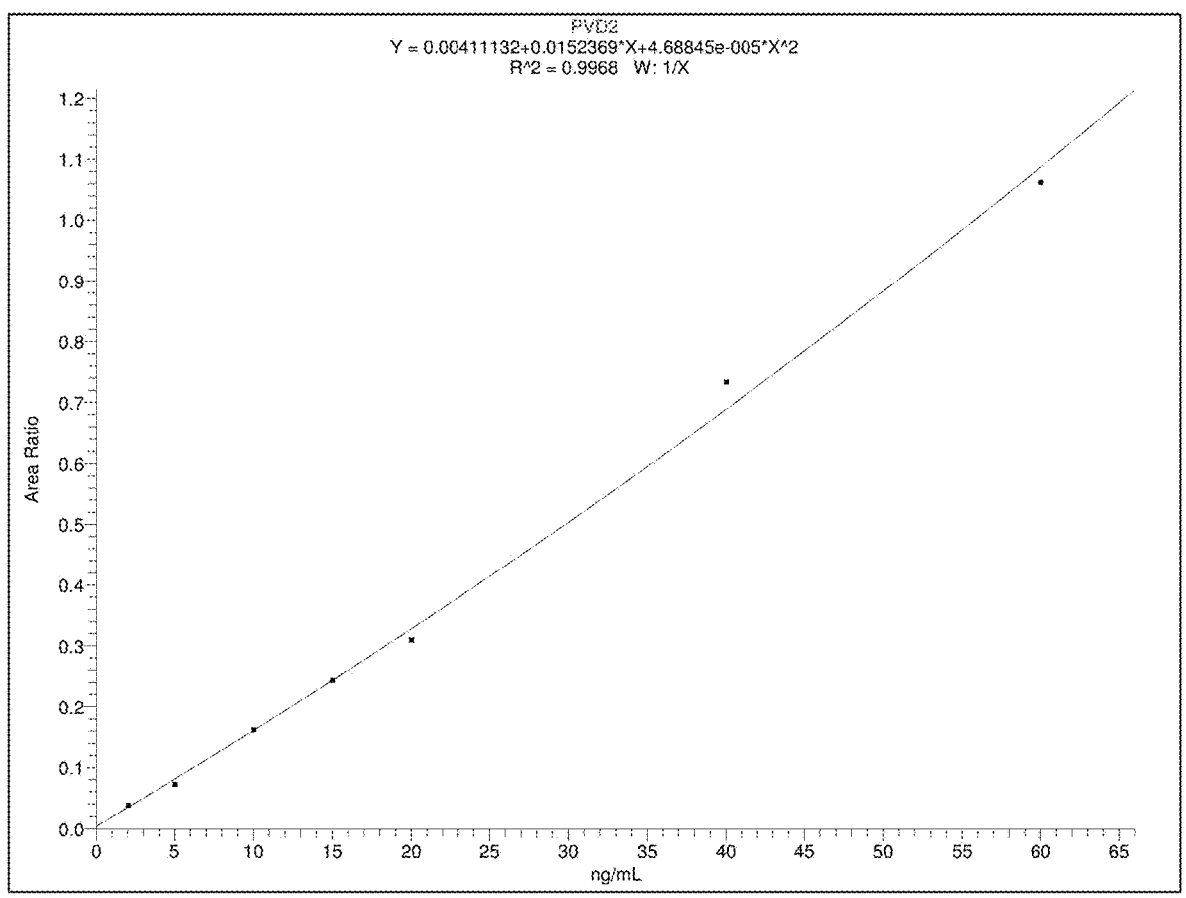
FIGS. 2A and 2B show exemplary calibration curves for vitamin $D_2$ and vitamin $D_3$ in serum samples determined by methods described in Example 3.
Figure 2B:
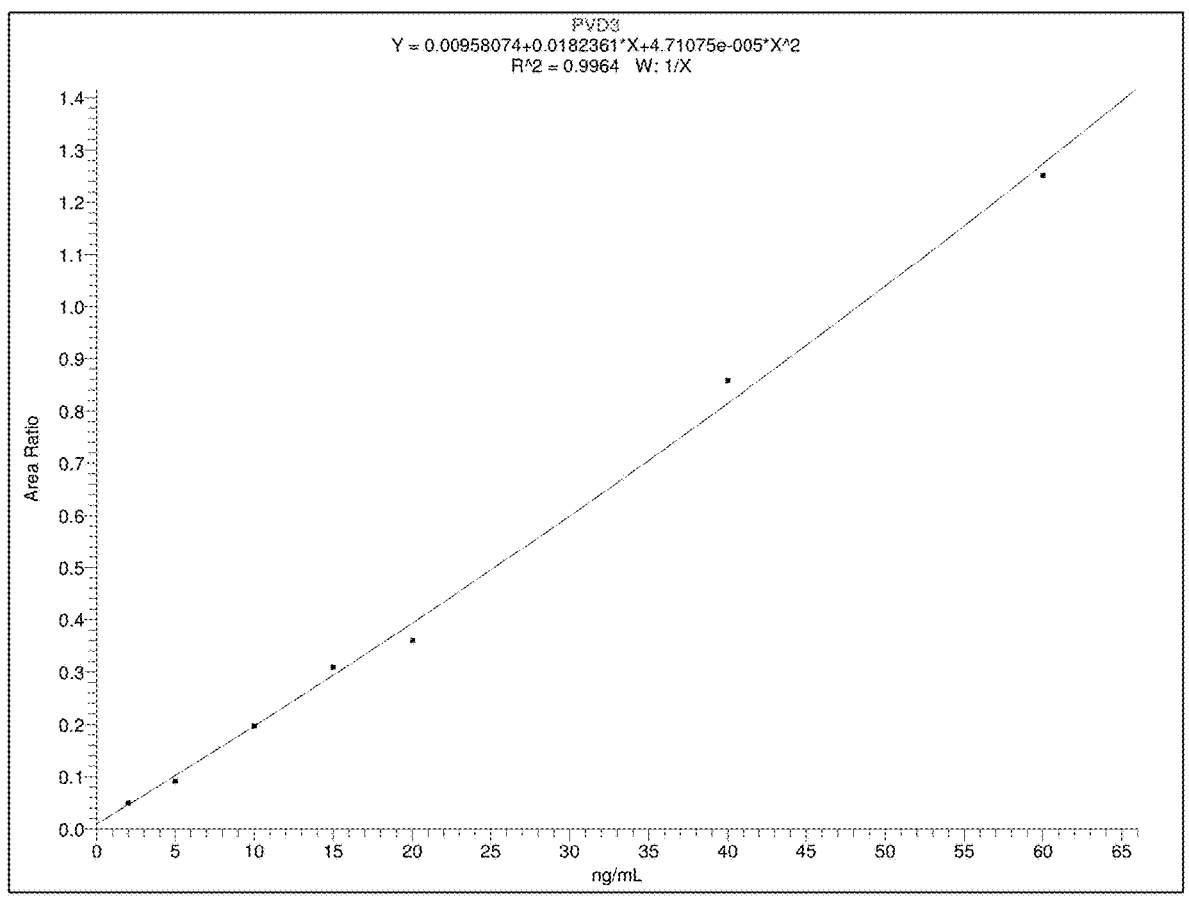

Exemplary calibration curves for the determination of vitamin $D_2$ and vitamin $D_3$ in serum specimens are shown in FIGS. 2A and 2B, respectively.

Example 4: Linearity of Response for Detection of Derivatized Vitamin D MS/MS

Linearity was determined by diluting four pools of serum with high endogenous concentration of either vitamin $D_2$ or vitamin $D_3$ and analyzing dilutions of 75%, 50%, and 25% in duplicate according to the methods of Examples 1-3. Specimens may be diluted 1:4 with average recovery of 102%, permitting a Clinically Reportable Range (CRR) of 2-240 ng/mL within precision limits of 85%-115% CV. Measured values and percent recoveries from these studies are shown in Table 3.

TABLE 3

Data Demonstrating Linearity of Response over Dilution Range

| Nutritional Vitamin $D_2$ (ng/mL (percent recovery %)) | | | | | | |
|---|---|---|---|---|---|---|
| Concentration | Pool 1 | Pool 2 | Pool 3 | Pool 4 | Pool 5 | Pool 6 |
| 100% | 25.0 (100) | 24.5 (100) | 28.1 (100) | 24.4 (100) | 28.1 (100) | 26.7 (100) |
| 75% | 17.8 (95.3) | 17.5 (95.4) | 21.9 (103.7) | 17.3 (94.5) | 21.2 (100.4) | 20.1 (100.5) |

TABLE 3-continued

Data Demonstrating Linearity of Response over Dilution Range

| 50% | 12.8 | 13.0 | 14.0 | 13.8 | 14.8 | 11.8 |
|---|---|---|---|---|---|---|
|  | (102.3) | (106.2) | (99.4) | (112.8) | (105.7) | (88.9) |
| 25% | 6.7 | 6.2 | 7.7 | 6.7 | 7.3 | 7.4 |
|  | (107.9) | (101.4) | (109.6) | (109.6) | (104.1) | (110.7) |

Nutritional Vitamin $D_3$ (ng/mL (percent recovery %))

| Sample concentration | Pool 1 | Pool 2 | Pool 3 | Pool 4 | Pool 5 | Pool 6 |
|---|---|---|---|---|---|---|
| 100% | 31.2 | 33.5 | 33.4 | 29.1 | 29.6 | 30.6 |
|  | (100) | (100) | (100) | (100) | (100) | (100) |
| 75% | 22.1 | 23.6 | 25.8 | 22.0 | 24.8 | 24.1 |
|  | (94.2) | (93.8) | (102.8) | (100.8) | (111.9) | (104.8) |
| 50% | 15.9 | 16.1 | 16.5 | 15.7 | 15.9 | 15.0 |
|  | (101.9) | (96.1) | (98.5) | (107.8) | (107.8) | (98.0) |
| 25% | 7.6 | 7.9 | 8.5 | 7.3 | 8.0 | 8.0 |
|  | (97.6) | (94.3) | (101.8) | (100.4) | (108.4) | (105.0) |

Example 5: Analytical Sensitivity: Lower Limit of Quantitation (LLOQ) and Limit of Detection (LOD)

Figure 3:
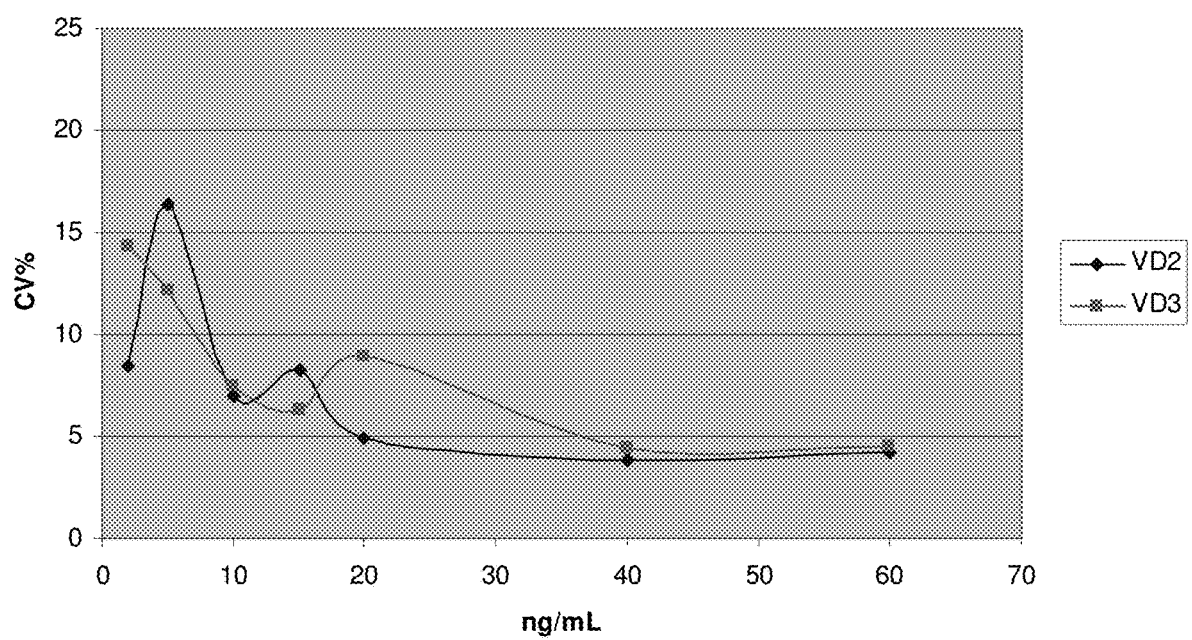
FIG. 3 shows a plots of coefficient of variation versus concentration for vitamin $D_2$ and vitamin $D_3$. Details are described in Example 5.

The lower limit of quantitation (LLOQ) is the point where measurements become quantitatively meaningful. The analyte response at this LLOQ is identifiable, discrete and reproducible with a precision (i.e., coefficient of variation (CV)) of greater than 20% and an accuracy of 80% to 120%. The LLOQ was determined by assaying samples with known analyte concentrations (2 ng/mL, 5 ng/mL, 10 ng/mL, 15 ng/mL, 20 ng/mL, 40 ng/mL, and 60 ng/mL) in quadruplicate five times according to the methods of Examples 1-3, then evaluating the reproducibility. Analysis of the collected data indicates that samples with concentrations of less than 2 ng/mL yielded CVs of less than 20% for both analytes. Thus, the LLOQ of each analyte was determined to be <2 ng/mL. Data generated for the determination of LLOQ of PTAD-vitamin $D_2$ and PTAD-vitamin $D_3$ are shown in Tables 4 and 5, respectively. The graphical representations of CV versus concentration for both analytes are shown in FIG. 3.

TABLE 4

Determination of Lower Limit of Quantitation of Vitamin $D_2$

| Vitamin $D_2$ concentration (ng/mL) | Assay 1 | Assay 2 | Assay 3 | Assay 4 | Assay 5 | | |
|---|---|---|---|---|---|---|---|
| 2 | 2.1 | 1.9 | 2.1 | 1.9 | 2.0 | Average | 2.04 |
|  | 1.7 | 2.0 | 2.1 | 1.9 | 2.0 | Std Dev | 0.2 |
|  | 1.9 | 2.0 | 2.2 | 2.2 | 2.3 | CV (%) | 8.5 |
|  | 1.9 | 1.9 | 2.1 | 2.5 | 2.2 | Accuracy (%) | 101.8 |
| 5 | 4.0 | 6.2 | 4.3 | 4.7 | 4.0 | Average | 4.7 |
|  | NC | 4.6 | 4.6 | 4.6 | 4.6 | Std Dev | 0.6 |
|  | 4.6 | 5.6 | 5.1 | 4.7 | 4.3 | CV (%) | 12.8 |
|  | 5.7 | 4.1 | 4.6 | 4.6 | 5.3 | Accuracy (%) | 94.8 |
| 10 | 9.8 | 11.2 | 10.8 | 11.3 | 10.3 | Average | 10.3 |
|  | 11.3 | 9.6 | 8.6 | 10.0 | 10.9 | Std Dev | 0.7 |
|  | 10.9 | 10.6 | 9.9 | 9.6 | 10.1 | CV (%) | 6.9 |
|  | 10.0 | 9.7 | 9.6 | 10.2 | 10.9 | Accuracy (%) | 102.6 |
| 15 | 13.6 | 14.7 | 15.6 | 15.0 | 14.5 | Average | 14.6 |
|  | 13.0 | 16.2 | 15.6 | 12.7 | 17.4 | Std Dev | 1.2 |
|  | 13.6 | 13.4 | 13.6 | 14.1 | 13.4 | CV (%) | 8.2 |
|  | 14.8 | 14.6 | 16.0 | 14.8 | 14.6 | Accuracy (%) | 97.1 |
| 20 | 19.4 | 19.1 | 20.3 | 19.9 | 19.1 | Average | 20.2 |
|  | 22.0 | 18.6 | 20.7 | 21.6 | 19.4 | Std Dev | 1.0 |
|  | 19.0 | 21.1 | 21.9 | 20.8 | 20.1 | CV (%) | 4.9 |
|  | 20.0 | 19.6 | 19.3 | 20.7 | 20.4 | Accuracy (%) | 100.8 |
| 40 | 42.2 | 41.5 | 39.1 | 42.5 | 41.8 | Average | 40.3 |
|  | 39.2 | 40.6 | 39.8 | 39.0 | 37.8 | Std Dev | 1.6 |
|  | 40.2 | 40.0 | 41.3 | 40.4 | 37.6 | CV (%) | 3.9 |
|  | 41.1 | 39.6 | 38.9 | 39.6 | 43.6 | Accuracy (%) | 100.7 |
| 60 | 64.4 | 57.8 | 59.1 | 59.3 | 57.0 | Average | 59.8 |
|  | 57.4 | 61.4 | 62.3 | 60.8 | 65.2 | Std Dev | 2.5 |
|  | 58.9 | 59.2 | 56.8 | 59.0 | 62.0 | CV (%) | 4.2 |
|  | 58.1 | 61.1 | 61.8 | 59.7 | 55.6 | Accuracy (%) | 99.7 |

TABLE 5

Determination of Lower Limit of Quantitation of Vitamin $D_3$

| Vitamin $D_3$ concentration (ng/mL) | Assay 1 | Assay 2 | Assay 3 | Assay 4 | Assay 5 | | |
|---|---|---|---|---|---|---|---|
| 2 | 2.1 | 1.6 | 2.2 | 2.0 | 1.8 | Average | 2.03 |
|  | 2.1 | 1.8 | 2.2 | 1.8 | 1.8 | Std Dev | 0.3 |
|  | 1.6 | 2.3 | 2.0 | 2.3 | 1.7 | CV (%) | 14.3 |
|  | 2.0 | 2.5 | 2.0 | 2.0 | 2.7 | Accuracy (%) | 101.4 |
| 5 | 4.7 | 5.6 | 4.6 | 5.0 | 4.9 | Average | 5.0 |
|  | 7.1 | 4.9 | 4.7 | 5.3 | 4.4 | Std Dev | 0.6 |
|  | 4.6 | 5.0 | 5.4 | 5.5 | 5.0 | CV (%) | 12.2 |
|  | 4.6 | 4.7 | 4.3 | 4.7 | 5.1 | Accuracy (%) | 99.7 |
| 10 | 9.4 | 10.2 | 10.1 | 9.9 | 11.0 | Average | 10.0 |
|  | 11.6 | 9.6 | 9.3 | 10.3 | 10.0 | Std Dev | 0.7 |
|  | 10.1 | 10.2 | 9.2 | 9.0 | 11.3 | CV (%) | 7.5 |
|  | 9.5 | 8.6 | 10.0 | 9.5 | 10.2 | Accuracy (%) | 99.5 |
| 15 | 14.5 | 14.9 | 14.4 | 15.7 | 15.8 | Average | 15.0 |
|  | 14.2 | 16.6 | 15.7 | 12.8 | 15.5 | Std Dev | 0.9 |
|  | 15.3 | 13.8 | 14.2 | 15.1 | 14.4 | CV (%) | 6.3 |
|  | 15.7 | 15.1 | 16.1 | 16.0 | 14.2 | Accuracy (%) | 100.0 |
| 20 | 19.8 | 18.4 | 18.2 | 22.2 | 17.5 | Average | 19.5 |
|  | 19.0 | 19.1 | 25.0 | 19.9 | 20.9 | Std Dev | 1.7 |
|  | 17.8 | 20.1 | 20.0 | 20.1 | 18.3 | CV (%) | 8.9 |
|  | 17.8 | 19.7 | 19.7 | 18.6 | 18.6 | Accuracy (%) | 97.7 |
| 40 | 44.3 | 41.7 | 40.6 | 39.1 | 42.0 | Average | 41.0 |
|  | 39.3 | 40.3 | 38.5 | 40.2 | 38.6 | Std Dev | 1.8 |
|  | 42.6 | 42.6 | 42.0 | 41.7 | 40.1 | CV (%) | 4.4 |
|  | 42.2 | 42.1 | 37.8 | 40.3 | 44.0 | Accuracy (%) | 102.5 |
| 60 | 65.0 | 57.0 | 60.3 | 60.6 | 55.7 | Average | 59.5 |
|  | 57.6 | 61.5 | 61.1 | 59.3 | 62.6 | Std Dev | 2.7 |
|  | 55.4 | 55.6 | 56.9 | 60.0 | 61.6 | CV (%) | 4.5 |
|  | 58.2 | 62.4 | 61.7 | 59.3 | 58.1 | Accuracy (%) | 99.2 |

The limit of detection (LOD) is the point where a measured value is larger than the uncertainty associated with it and is defined arbitrarily as four standard deviations (SD) from the zero concentration. Selectivity is the ability of an analytical method to differentiate and quantify the analyte in the presence of other components in the sample. A blank was analyzed in 20 replicates according to the methods of Examples 1-3 and the resulting area ratios were statistically analyzed to determine that the LOD for both vitamin $D_2$ and vitamin $D_3$ are 0.4 ng/mL. Data collected to determine LOD for each analyte is shown in Table 6.

TABLE 6

Determination of Limit of Detection of Vitamin $D_2$ and Vitamin $D_3$

| Replicate # | $NVD_2$ (Response Ratio) | $NVD_3$ (Response Ratio) |
|---|---|---|
| 1 | 0.012 | 0.014 |
| 2 | 0.004 | 0.005 |

TABLE 6-continued

Determination of Limit of Detection of Vitamin $D_2$ and Vitamin $D_3$

| Replicate # | NVD$_2$ (Response Ratio) | NVD$_3$ (Response Ratio) |
| --- | --- | --- |
| 3 | 0.008 | 0.011 |
| 4 | 0.005 | 0.004 |
| 5 | 0.018 | 0.03 |
| 6 | 0.004 | 0.001 |
| 7 | 0.007 | 0.006 |
| 8 | 0.006 | 0.002 |
| 9 | 0.014 | 0.006 |
| 10 | 0.015 | 0.006 |
| 11 | 0.003 | 0.008 |
| 12 | 0.005 | 0.004 |
| 13 | 0.009 | 0.002 |
| 14 | 0.017 | 0.016 |
| 15 | 0.007 | 0.005 |
| 16 | 0.006 | 0.012 |
| 17 | 0.003 | 0.001 |
| 18 | 0.002 | 0.001 |
| 19 | 0.011 | 0.001 |
| 20 | 0.023 | 0.009 |
| Mean | 0.009 | 0.007 |
| SD | 0.0058 | 0.0070 |
| CV | 65.1 | 97.0 |
| Mean + 4SD | 0.032 | 0.035 |
| LOD | 0.4 ng/mL | 0.4 ng/mL |

Example 7: Specificity of Detection

Several samples were prepared with vitamin $D_2$, vitamin $D_3$, and spiked amounts of potentially interfering species (including vitamin D metabolites and related compounds) and analyzed according to the methods of Examples 1-3. The compounds tested for potential interference are listed in Table 7. None of the tested compounds demonstrated cross-reactivity with detection of vitamin $D_2$ or vitamin $D_3$ according to the methods of Examples 1-3.

TABLE 7

Compounds Tested for Possible Interference with Detection of Vitamin $D_2$ or Vitamin $D_3$
Compounds Tested 1,25(OH)$_2$D$_3$
1,25(OH)$_2$D$_2$
1,25(OH)$_2$D$_3$-[6,19,19']-$^2$H
1,25(OH)$_2$D$_3$-[26,26,26,27,27,27]-$^2$H
1,25(OH)$_2$D$_2$-[26,26,26,27,27,27]-$^2$H
25OHD$_3$
25OHD$_2$
25OHD$_3$-IS-[6,19,19']-$^2$H
25OHD$_2$-IS-[6,19,19']-$^2$H
25OHD$_3$-IS-[26,26,26,27,27,27]-$^2$H
25OHD$_2$-IS-[26,26,26,27,27,27]-$^2$H
vitamin D$_3$-[6,19,19']-$^2$H
vitamin D$_2$-[6,19,19']-$^2$H
vitamin D$_3$-[26,26,26,27,27,27]-$^2$H
vitamin D$_2$-[26,26,26,27,27,27]-$^2$H
1-OH-D$_3$ (Alfacalcidiol)
1-OH-D$_2$ (Hectoral)
24,25(OH)$_2$D$_3$
25,26(OH)$_2$D$_3$
3-epi-25OHD$_3$
3-epi-1,25(OH)$_2$D$_3$
Dihydrotachysterol
1,25(OH)$_2$D$_3$-26,23-lactone
Paracalcitol (Zemplar)
Calcipotriene (Dovonex)
7-Dehydrocholesterol

Example 8: Reproducibility of Quantitation of Vitamin $D_2$ and Vitamin $D_3$ The intra-assay variation is defined as the reproducibility of a sample within an assay and was determined by assaying 20 replicates of a sample from each of three QC pools according to the methods of Examples 1-3. Data collected from these analyses are shown in Tables 8 and 9 for vitamin $D_2$ and vitamin $D_3$, respectively. The concentrations of the analytes in the QC pools were determined to be 6.6 ng/mL, 20.6 ng/mL, and 52.6 ng/mL for vitamin $D_2$, and 4.9 ng/mL, 20.5 ng/mL, and 48.6 ng/mL for Vitamin $D_3$. Statistics performed on the results yielded reproducibility for the three QC pools at 5.1%, 4.6%, and 3.9% for vitamin $D_2$, and 6.4%, 4.0%, and 4.5% for vitamin $D_3$.

TABLE 8

Intra-Assay Variation Determination for Vitamin $D_2$

| | Low QC Pool (ng/mL) Lot 120709-L | Medium QC Pool (ng/mL) Lot 120709-M | High QC Pool (ng/mL) Lot 120709-H |
| --- | --- | --- | --- |
| 1 | 6.7 | 20.3 | 52.5 |
| 2 | 6.6 | 21.0 | 54.7 |
| 3 | 7.0 | 21.1 | 51.5 |
| 4 | 6.2 | 19.5 | 52.1 |
| 5 | 6.4 | 20.0 | 52.0 |
| 6 | 6.2 | 22.4 | 53.3 |
| 7 | 7.0 | 20.4 | 48.9 |
| 8 | 6.7 | 21.5 | 54.6 |
| 9 | 6.7 | 21.5 | 52.4 |
| 10 | 6.9 | 20.9 | 52.5 |
| 11 | 7.0 | 19.2 | 50.2 |
| 12 | 6.2 | 20.8 | 52.3 |
| 13 | 7.0 | 19.6 | 57.5 |
| 14 | 6.6 | 20.6 | 54.7 |
| 15 | 6.2 | 19.8 | 53.0 |
| 16 | 6.2 | 20.6 | 49.2 |
| 17 | 6.2 | 22.9 | 52.5 |
| 18 | 6.2 | 20.9 | 51.4 |
| 19 | 7.0 | 19.6 | 52.2 |
| 20 | 6.5 | 20.3 | 55.2 |
| Mean | 6.6 | 20.6 | 52.6 |
| SD | 0.3 | 1.0 | 2.0 |
| CV % | 5.1 | 4.6 | 3.9 |

TABLE 9

Intra-Assay Variation Determination for Vitamin $D_3$

| | Low QC Pool (ng/mL) Lot 120709-L | Medium QC Pool (ng/mL) Lot 120709-M | High QC Pool (ng/mL) Lot 120709-H |
| --- | --- | --- | --- |
| 1 | 4.3 | 20.0 | 48.3 |
| 2 | 5.1 | 21.8 | 47.2 |
| 3 | 4.8 | 21.7 | 45.4 |
| 4 | 4.5 | 21.3 | 49.9 |
| 5 | 5.0 | 20.5 | 49.8 |
| 6 | 4.7 | 21.0 | 48.2 |
| 7 | 5.8 | 20.4 | 46.3 |
| 8 | 4.9 | 21.2 | 50.8 |
| 9 | 4.7 | 22.0 | 49.1 |
| 10 | 4.7 | 20.1 | 48.9 |
| 11 | 4.8 | 19.1 | 47.3 |
| 12 | 4.7 | 19.9 | 49.1 |
| 13 | 4.9 | 19.5 | 52.9 |
| 14 | 5.4 | 20.3 | 52.7 |
| 15 | 4.7 | 19.6 | 51.3 |
| 16 | 4.8 | 19.9 | 46.7 |
| 17 | 4.8 | 21.0 | 47.5 |

TABLE 9-continued

Intra-Assay Variation Determination for Vitamin $D_3$

| | Low QC Pool (ng/mL) Lot 120709-L | Medium QC Pool (ng/mL) Lot 120709-M | High QC Pool (ng/mL) Lot 120709-H |
|---|---|---|---|
| 18 | 4.7 | 21.1 | 46.9 |
| 19 | 5.0 | 19.7 | 45.3 |
| 20 | 5.1 | 20.4 | 48.8 |
| Mean | 4.9 | 20.5 | 48.6 |
| SD | 0.3 | 0.8 | 2.2 |
| CV % | 6.4 | 4.0 | 4.5 |

The inter-assay variation is defined as the reproducibility (CV) of a sample between assays. Using the three QC pools covering the reportable range of the assay, evaluated over 5 assays according to the methods of Examples 1-3, the inter-assay variation (CV) for the pools was determined for vitamin $D_2$ and vitamin $D_3$. For Vitamin $D_2$, the CVs were determined to be 6.7%, 5.6%, and 4.0% with mean concentrations of 6.5 ng/mL, 21.1 ng/mL, and 50.5 ng/mL, respectively. For Vitamin $D_3$, the CVs were determined to be 6.5%, 5.9%, and 4.2% with mean concentrations of 4.7 ng/mL, 20.8 ng/mL, and 46.8 ng/mL, respectively. Data collected from these analyses are shown in Tables 10 and 11 for vitamin $D_2$ and vitamin $D_3$, respectively. All pools met with acceptable reproducibility requirements of <15% CV.

TABLE 10

Inter-Assay Variation Determination for Vitamin $D_2$

| Assay | Low QC Pool (ng/mL) Lot 120709-L | Medium QC Pool (ng/mL) Lot 120709-M | High QC Pool (ng/mL) Lot 120709-H |
|---|---|---|---|
| 1 | 6.7 | 20.3 | 52.5 |
| | 6.6 | 21.0 | 54.7 |
| | 7.0 | 21.1 | 51.5 |
| | 6.2 | 19.5 | 52.1 |
| | 6.4 | 20.0 | 52.0 |
| 2 | 7.3 | 23.3 | 49.4 |
| | 6.8 | 22.1 | 51.6 |
| | 6.7 | 20.6 | 48.6 |
| | 6.7 | 20.6 | 47.2 |
| | 7.0 | 21.1 | 50.4 |
| 3 | 6.3 | 22.3 | 49.7 |
| | 6.1 | 23.0 | 52.2 |
| | 6.6 | 24.0 | 49.5 |
| | 5.6 | 22.1 | 49.6 |
| | 6.1 | 19.1 | 51.7 |
| 4 | 6.1 | 20.5 | 47.5 |
| | 7.0 | 21.1 | 50.1 |
| | 6.9 | 22.2 | 50.2 |
| | 7.3 | 22.1 | 48.3 |
| | 6.6 | 20.2 | 46.8 |
| 5 | 5.8 | 21.1 | 52.4 |
| | 6.9 | 19.6 | 49.6 |
| | 6.0 | 20.8 | 49.1 |
| | 6.4 | 20.6 | 56.1 |
| | 6.3 | 20.1 | 50.8 |
| 6 | 6.3 | 21.8 | 50.0 |
| | 7.0 | 22.5 | 49.8 |
| | 6.2 | 21.6 | 51.2 |
| | 5.9 | 20.1 | 50.3 |
| | 6.9 | 20.1 | 50.9 |
| Mean | 6.5 | 21.1 | 50.5 |
| SD | 0.4 | 1.2 | 2.0 |
| CV % | 6.7 | 5.6 | 4.0 |

TABLE 11

Inter-Assay Variation Determination for Vitamin $D_3$

| Assay | Low QC Pool (ng/mL) Lot 120709-L | Medium QC Pool (ng/mL) Lot 120709-M | High QC Pool (ng/mL) Lot 120709-H |
|---|---|---|---|
| 1 | 4.3 | 20.0 | 48.3 |
| | 5.1 | 21.8 | 47.2 |
| | 4.8 | 21.7 | 45.4 |
| | 4.5 | 21.3 | 49.9 |
| | 5.0 | 20.5 | 49.8 |
| 2 | 4.5 | 23.0 | 46.3 |
| | 4.2 | 22.8 | 47.8 |
| | 4.5 | 19.8 | 45.1 |
| | 4.4 | 20.1 | 44.4 |
| | 4.7 | 21.1 | 48.7 |
| 3 | 4.9 | 21.8 | 44.9 |
| | 5.1 | 20.9 | 46.8 |
| | 5.2 | 23.9 | 45.5 |
| | 4.4 | 22.1 | 45.7 |
| | 4.6 | 19.3 | 47.1 |
| 4 | 4.5 | 20.1 | 43.7 |
| | 4.8 | 21.2 | 44.6 |
| | 5.2 | 21.9 | 46.1 |
| | 4.7 | 21.3 | 44.1 |
| | 4.7 | 20.5 | 42.8 |
| 5 | 4.5 | 20.5 | 49.1 |
| | 5.1 | 20.8 | 46.9 |
| | 4.5 | 21.3 | 47.3 |
| | 4.8 | 20.6 | 45.8 |
| | 4.2 | 19.7 | 46.1 |
| 6 | 4.7 | 19.9 | 49.6 |
| | 4.7 | 18.9 | 47.6 |
| | 4.4 | 20.2 | 48.9 |
| | 4.4 | 18.6 | 48.5 |
| | 5.2 | 19.4 | 49.4 |
| Mean | 4.7 | 20.8 | 46.8 |
| SD | 0.3 | 1.2 | 2.0 |
| CV % | 6.5 | 5.9 | 4.2 |

Example 9: Method Correlation Studies for Quantitation of Vitamin $D_2$

A method correlation study was performed for quantitation of vitamin $D_2$ according to the methods of Examples 1-3 by comparing 20 split samples analyzed according to the tandem mass spectrometric methods described herein with extensive off-line extraction followed by HPLC with UV detection. Specimens were analyzed in singles for each method. Data was analyzed by Linear and Deming regressions. Correlation analyses are summarized in Table 12.

TABLE 12

Correlation Analyses for Method Comparison Vitamin $D_2$ (n = 20)

| Linear Regression | y = 1.26x − 0.55 |
| | $R_2$ = 0.96 |
| Deming Regression | y = 1.29x − 1.31 |

Example 10: Interference Studies

Hemolysis Interference: The effects of hemolysis in the assay described in Examples 1-3 were evaluated by spiking hemoglobin into serum pools containing elevated vitamin $D_2$ and vitamin $D_3$. A fresh blood sample was centrifuged to yield packed red blood cells. The cells were reconstituted in deionized water and frozen to achieve cell lysis. This crude hemoglobin solution was then was spiked into the pools to generate lightly (100 mg/dL) and moderately (500 mg/dL)

hemolyzed samples. Specimens were analyzed in duplicate according the method in Examples 1-3 and results were compared to the control pool result and a percent difference was calculated. The data shows that none of the hemoglobin spikes was >15% different than control, for either analyte). Therefore, light to moderate hemolyzed specimens are acceptable. For raw data see Table 13 (% Difference=(Spiked−UnSpiked)/UnSpiked×100%).

TABLE 13

Hemolysis Interference Studies

| | | Vitamin $D_2$ | | Vitamin $D_3$ | |
|---|---|---|---|---|---|
| | | ng/mL | % Diff. | ng/mL | % Diff. |
| Pool 1 | Control | 22.1 | | 31.2 | |
| | Light Hemolysis | 24.3 | 9.7 | 33.8 | 8.5 |
| | Moderate Hemolysis | 23.8 | 7.6 | 34.3 | 10.0 |
| Pool 2 | Control | 22.3 | | 34.8 | |
| | Light Hemolysis | 21.3 | −4.8 | 32.6 | −6.4 |
| | Moderate Hemolysis | 20.7 | −7.2 | 33.3 | −4.5 |
| Pool 3 | Control | 27.3 | | 34.6 | |
| | Light Hemolysis | 26.7 | −2.2 | 34.7 | 0.2 |
| | Moderate Hemolysis | 24.6 | −9.8 | 33.4 | −3.5 |
| Pool 4 | Control | 23.7 | | 30.4 | |
| | Light Hemolysis | 22.8 | −3.8 | 31.5 | 3.6 |
| | Moderate Hemolysis | 21.2 | −10.6 | 29.8 | −2.0 |
| Pool 5 | Control | 27.7 | | 33.9 | |
| | Light Hemolysis | 26.7 | −3.4 | 33.7 | −0.4 |
| | Moderate Hemolysis | 25.6 | −7.5 | 33.2 | −1.9 |
| Pool 6 | Control | 24.2 | | 33.6 | |
| | Light Hemolysis | 24.3 | 0.3 | 33.5 | −0.4 |
| | Moderate Hemolysis | 24.1 | 0.5 | 34.1 | 1.3 |

Icteria Interference: The effects of icteria in the assay described in Examples 1-3 were evaluated by spiking bilirubin into serum pools containing elevated vitamin $D_2$ and vitamin $D_3$. A concentrated solution of bilirubin was spiked into the pools to generate lightly (10 mg/dL) and moderately (50 mg/dL) icteric specimens. Specimens were analyzed in duplicate according to the method in Examples 1-3 and results were compared to the non-icteric pool result and the accuracy was calculated. The data shows that both analytes are unaffected by icteria (all values within acceptable accuracy range of 85-115%). Therefore, icteric specimens are acceptable. For raw data see Table 14 (% Difference=(Spiked−UnSpiked)/UnSpiked×100%).

TABLE 14

Icteria Interference Studies

| | | Vitamin $D_2$ | | Vitamin $D_3$ | |
|---|---|---|---|---|---|
| | | ng/mL | % Diff. | ng/mL | % Diff. |
| Pool 1 | Control | 22.1 | | 31.2 | |
| | Light Icteria | 22.2 | 0.3 | 32.6 | 4.8 |
| | Moderate Icteria | 21.5 | −2.6 | 30.7 | −1.6 |
| Pool 2 | Control | 22.3 | | 34.8 | |
| | Light Icteria | 22.0 | −1.3 | 33.4 | −4.0 |
| | Moderate Icteria | 20.5 | −8.2 | 32.4 | −6.9 |
| Pool 3 | Control | 27.3 | | 34.6 | |
| | Light Icteria | 28.3 | 3.8 | 35.2 | 1.8 |
| | Moderate Icteria | 27.1 | −0.7 | 35.0 | 1.0 |

TABLE 14-continued

Icteria Interference Studies

| | | Vitamin $D_2$ | | Vitamin $D_3$ | |
|---|---|---|---|---|---|
| | | ng/mL | % Diff. | ng/mL | % Diff. |
| Pool 4 | Control | 23.7 | | 30.4 | |
| | Light Icteria | 22.2 | −6.3 | 31.7 | 4.0 |
| | Moderate Icteria | 21.7 | −8.7 | 30.7 | 1.0 |
| Pool 5 | Control | 27.7 | | 33.9 | |
| | Light Icteria | 26.7 | −3.7 | 32.9 | −2.8 |
| | Moderate Icteria | 27.1 | −2.0 | 32.4 | −4.4 |
| Pool 6 | Control | 24.2 | | 33.6 | |
| | Light Icteria | 22.8 | −5.8 | 31.8 | −5.5 |
| | Moderate Icteria | 22.6 | −6.4 | 30.5 | −9.4 |

Lipemia Interference: The effect of lipemia in the assay described in Examples 1-3 was evaluated by spiking porcine brain extract into serum pools containing elevated vitamin $D_2$ and vitamin $D_3$. Powdered lipid sample (Avanti Polar Lipids) was dissolved into each pool to generate lightly (400 mg/dL) and moderately (2000 mg/dL) lipemic specimens. Specimens were analyzed in duplicate according to the method in Examples 1-3 and results were compared to the control pool result and the accuracy was calculated. The data shows that both analytes are unaffected by lipemia (all values within acceptable accuracy range of 85-115%). For raw data see Table 15 ((% Difference=(Spiked−UnSpiked)/UnSpiked×100%).

TABLE 15

Lipemia Interference (Porcine Brain Extract) Studies

| | | Vitamin $D_2$ | | Vitamin $D_3$ | |
|---|---|---|---|---|---|
| | | ng/mL | % Diff. | ng/mL | % Diff. |
| Pool 1 | Control | 22.1 | | 31.2 | |
| | Light Lipemia | 22.0 | −0.6 | 32.7 | 4.8 |
| | Moderate Lipemia | 23.0 | 3.8 | 32.7 | 5.0 |
| Pool 2 | Control | 22.3 | | 34.8 | |
| | Light Lipemia | 23.0 | 3.2 | 35.4 | 1.6 |
| | Moderate Lipemia | 24.2 | 8.3 | 34.7 | −0.2 |
| Pool 3 | Control | 27.3 | | 34.6 | |
| | Light Lipemia | 28.7 | 5.4 | 35.7 | 2.9 |
| | Moderate Lipemia | 28.1 | 3.3 | 36.5 | 5.3 |
| Pool 4 | Control | 23.7 | | 30.4 | |
| | Light Lipemia | 25.5 | 7.4 | 33.2 | 9.0 |
| | Moderate Lipemia | 23.2 | −2.5 | 32.7 | 7.3 |
| Pool 5 | Control | 27.7 | | 33.9 | |
| | Light Lipemia | 27.1 | −2.2 | 34.4 | 1.5 |
| | Moderate Lipemia | 26.7 | −3.4 | 33.9 | 0.1 |
| Pool 6 | Control | 24.2 | | 33.6 | |
| | Light Lipemia | 26.1 | 8.0 | 34.5 | 2.5 |
| | Moderate Lipemia | 24.0 | −0.7 | 33.6 | −0.2 |

The effects of lipemia in the assay described in Examples 1-3 were also evaluated by spiking Intralipid emulsion into serum pools containing elevated vitamin $D_2$ and vitamin $D_3$. To the serum pools, Intralipid (20% emulsion) was added to generate lightly (400 mg/dL) and moderately (2000 mg/dL) lipemic specimens. Specimens were analyzed in duplicate according to the method in Examples 1-3 and results were compared to the control pool result and the accuracy was calculated. The data shows that both analytes are unaffected by lipemia (all values within acceptable accuracy range of 85-115%). For raw data see Table 16.

TABLE 16

Lipemia Interference (Intralipid) Studies

| | | Vitamin D₂ | | Vitamin D₃ | |
|---|---|---|---|---|---|
| | | ng/mL | % Diff. | ng/mL | % Diff. |
| Pool 1 | Control | 22.1 | | 31.2 | |
| | Light Lipemia | 22.5 | 1.6 | 33.3 | 6.8 |
| | Moderate Lipemia | 19.8 | −10.4 | 28.8 | −7.6 |
| Pool 2 | Control | 22.3 | | 34.8 | |
| | Light Lipemia | 22.4 | 0.4 | 33.5 | −3.6 |
| | Moderate Lipemia | 19.2 | −13.8 | 30.5 | −12.3 |
| Pool 3 | Control | 27.3 | | 34.6 | |
| | Light Lipemia | 27.4 | 0.6 | 34.5 | −0.3 |
| | Moderate Lipemia | 24.9 | −8.6 | 32.5 | −6.1 |
| Pool 4 | Control | 23.7 | | 30.4 | |
| | Light Lipemia | 23.6 | −0.6 | 31.3 | 3.0 |
| | Moderate Lipemia | 19.9 | −16.0 | 29.8 | −2.0 |
| Pool 5 | Control | 27.7 | | 33.9 | |
| | Light Lipemia | 27.4 | −1.1 | 32.0 | −5.6 |
| | Moderate Lipemia | 25.8 | −6.9 | 31.9 | −5.9 |
| Pool 6 | Control | 24.2 | | 33.6 | |
| | Light Lipemia | 24.5 | 1.2 | 33.8 | 0.6 |
| | Moderate Lipemia | 22.8 | −5.9 | 30.0 | −10.7 |

Based upon the two lipemia experiments using porcine brain extract and Intralipid, lipemic specimens are acceptable.

Example 11: Specimen Type Studies

Specimens were collected from 10 sources into four different Vacutainer® containers. The Vacutainers used were Red-Top (silicon-coated serum tubes), SST (Serum Separator Tubes, which result in gel-barrier serum), EDTA tubes, and Sodium Heparin tubes.

Figure 4:
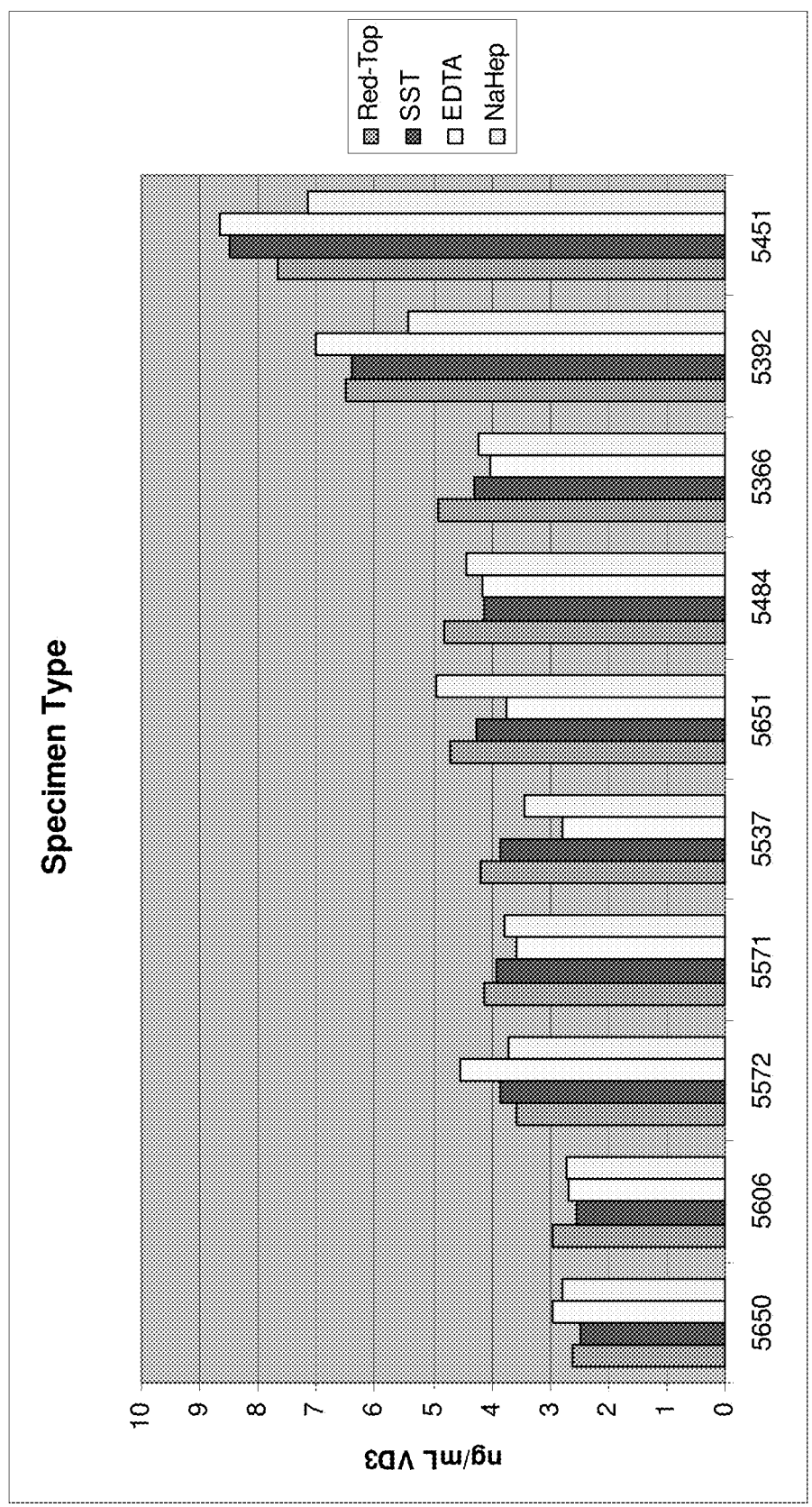
FIG. 4 shows results of comparative studies of analysis of vitamin $D_3$ in different sample matrices. Details are described in Example 11.

These 40 samples were analyzed for nutritional vitamin $D_3$ according to the method in Examples 1-3. Comparative results are presented in FIG. 4. The data demonstrates that all four sample types are suitable for analysis.

Example 12: Demonstration of Routine Range for Vitamin $D_3$

Serum specimens from 140 patients were analyzed according to the method described in Examples 1-3 to quantitate vitamin $D_3$. The results ranged from <2 ng/mL to about 63 ng/mL vitamin $D_3$, with 95% of the results falling within the range of <2 ng/mL to about 20 ng/mL. The results of these analyses are presented in Table 17.

TABLE 17

Routine Range Studies for Vitamin $D_3$ (in descending order)

| Patient | Vit $D_3$ (ng/mL) |
|---|---|
| 1 | 62.8 |
| 2 | 35.8 |
| 3 | 24.3 |
| 4 | 20.2 |
| 5 | 15.6 |
| 6 | 15.6 |
| 7 | 15.5 |
| 8 | 14.6 |
| 9 | 14.3 |
| 10 | 12.7 |
| 11 | 12.7 |
| 12 | 12.5 |
| 13 | 10.5 |
| 14 | 10.3 |
| 15 | 9.8 |
| 16 | 9.6 |
| 17 | 9.6 |
| 18 | 7.9 |
| 19 | 7.4 |
| 20 | 6.6 |
| 21 | 6.5 |
| 22 | 6.4 |
| 23 | 5.9 |
| 24 | 5.8 |
| 25 | 5.5 |
| 26 | 5.4 |
| 27 | 5.3 |
| 28 | 5.1 |
| 29 | 5.1 |
| 30 | 5.0 |
| 31 | 4.9 |
| 32 | 4.8 |
| 33 | 4.6 |
| 34 | 4.6 |
| 35 | 4.4 |
| 36 | 4.3 |
| 37 | 4.2 |
| 38 | 4.2 |
| 39 | 4.0 |
| 40 | 3.9 |
| 41 | 3.9 |
| 42 | 3.9 |
| 43 | 3.7 |
| 44 | 3.6 |
| 45 | 3.4 |
| 46 | 3.3 |
| 47 | 3.2 |
| 48 | 3.2 |
| 49 | 3.2 |
| 50 | 3.2 |
| 51 | 3.2 |
| 52 | 3.1 |
| 53 | 2.8 |
| 54 | 2.8 |
| 55 | 2.7 |
| 56 | 2.6 |
| 57 | 2.6 |
| 58 | 2.5 |
| 59 | 2.3 |
| 60 | 2.2 |
| 61 | 2.2 |
| 62 | 2.2 |
| 63 | 2.2 |
| 64 | 2.1 |
| 65 | 2.0 |
| 66 | 2.0 |
| 67 | 2.0 |
| 68 | 2.0 |
| 69 | <2 |
| 70 | <2 |
| 71 | <2 |
| 72 | <2 |
| 73 | <2 |
| 74 | <2 |
| 75 | <2 |
| 76 | <2 |
| 77 | <2 |
| 78 | <2 |
| 79 | <2 |
| 80 | <2 |
| 81 | <2 |
| 82 | <2 |
| 83 | <2 |
| 84 | <2 |
| 85 | <2 |
| 86 | <2 |
| 87 | <2 |

TABLE 17-continued

Routine Range Studies for Vitamin $D_3$
(in descending order)

| Patient | Vit $D_3$ (ng/mL) |
|---|---|
| 88 | <2 |
| 89 | <2 |
| 90 | <2 |
| 91 | <2 |
| 92 | <2 |
| 93 | <2 |
| 94 | <2 |
| 95 | <2 |
| 96 | <2 |
| 97 | <2 |
| 98 | <2 |
| 99 | <2 |
| 100 | <2 |
| 101 | <2 |
| 102 | <2 |
| 103 | <2 |
| 104 | <2 |
| 105 | <2 |
| 106 | <2 |
| 107 | <2 |
| 108 | <2 |
| 109 | <2 |
| 110 | <2 |
| 111 | <2 |
| 112 | <2 |
| 113 | <2 |
| 114 | <2 |
| 115 | <2 |
| 116 | <2 |
| 117 | <2 |
| 118 | <2 |
| 119 | <2 |
| 120 | <2 |
| 121 | <2 |
| 122 | <2 |
| 123 | <2 |
| 124 | <2 |
| 125 | <2 |
| 126 | <2 |
| 127 | <2 |
| 128 | <2 |
| 129 | <2 |
| 130 | <2 |
| 131 | <2 |
| 132 | <2 |
| 133 | <2 |
| 134 | <2 |
| 135 | <2 |
| 136 | <2 |
| 137 | <2 |
| 138 | <2 |
| 139 | <2 |
| 140 | <2 |

Example 13: Recovery Studies

Mix recovery studies were performed by analysis of specimens with naturally elevated levels of 25-hydroxyvitamin $D_2$ or 25-hydroxyvitamin $D_3$, and therefore also had some endogenous circulating vitamin $D_2$ or vitamin $D_3$. Six pairs of specimens were selected for the studies. From each pair of specimens (generically referred to as specimen A and specimen B), five samples were prepared and analyzed in quadruplicate according to the method in Examples 1-3. The samples corresponded to 100% A, 80% A-20% B, 50% A-50% B, 20% A-80% B, and 100% B. The results of the recovery studies are presented in Tables 18 and 19.

TABLE 18

Mixed Specimen Recovery Studies

| Pool | Spike Level | Vitamin $D_2$ | | | Vitamin $D_3$ | | |
|---|---|---|---|---|---|---|---|
| | | Measured (ng/mL) | Expected (ng/mL) | Recovery (%) | Measured (ng/mL) | Expected (ng/mL) | Recovery (%) |
| 1 | 100% A | 49.0 | | | 2.1 | | |
| | 80/20 A/B | 37.8 | 39.3 | 103.8 | 3.3 | 3.5 | 106.1 |
| | 50/50 A/B | 26.0 | 24.7 | 94.8 | 5.6 | 5.5 | 96.9 |
| | 20/80 A/B | 10.5 | 10.1 | 96.5 | 7.6 | 7.5 | 98.5 |
| | 100% B | 0.4 | | | 8.8 | | |
| 2 | 100% A | 5.0 | | | 2.6 | | |
| | 80/20 A/B | 4.9 | 4.2 | 85.5 | 6.6 | 6.6 | 99.4 |
| | 50/50 A/B | 2.9 | 2.9 | 101.7 | 11.8 | 12.5 | 106.2 |
| | 20/80 A/B | 1.6 | 1.7 | 106.2 | 17.7 | 18.5 | 104.3 |
| | 100% B | 0.9 | | | 22.4 | | |
| 3 | 100% A | 8.8 | | | 3.0 | | |
| | 80/20 A/B | 7.6 | 7.4 | 96.7 | 6.6 | 6.6 | 101.2 |
| | 50/50 A/B | 5.4 | 5.2 | 95.8 | 11.3 | 12.1 | 106.7 |
| | 20/80 A/B | 3.1 | 3.0 | 99.1 | 16.3 | 17.5 | 107.6 |
| | 100% B | 1.6 | | | 21.2 | | |

*Measured values are averages of analysis of four aliquots.

TABLE 19

Summary of Results of Mixed Specimen Recovery Studies

| Pool | Vitamin $D_2$ | Vitamin $D_3$ |
|---|---|---|
| 1 | 103.8% | 106.1% |
|   | 94.8% | 96.9% |
|   | 96.5% | 98.5% |
| 2 | 85.5% | 99.4% |
|   | 101.7% | 106.2% |
|   | 106.2% | 104.3% |
| 3 | 96.7% | 101.2% |
|   | 95.8% | 106.7% |
|   | 99.1% | 107.6% |
| Avg | 97.8% | 103.0% |
| Avg | | 100.4% |

Figure 5A:
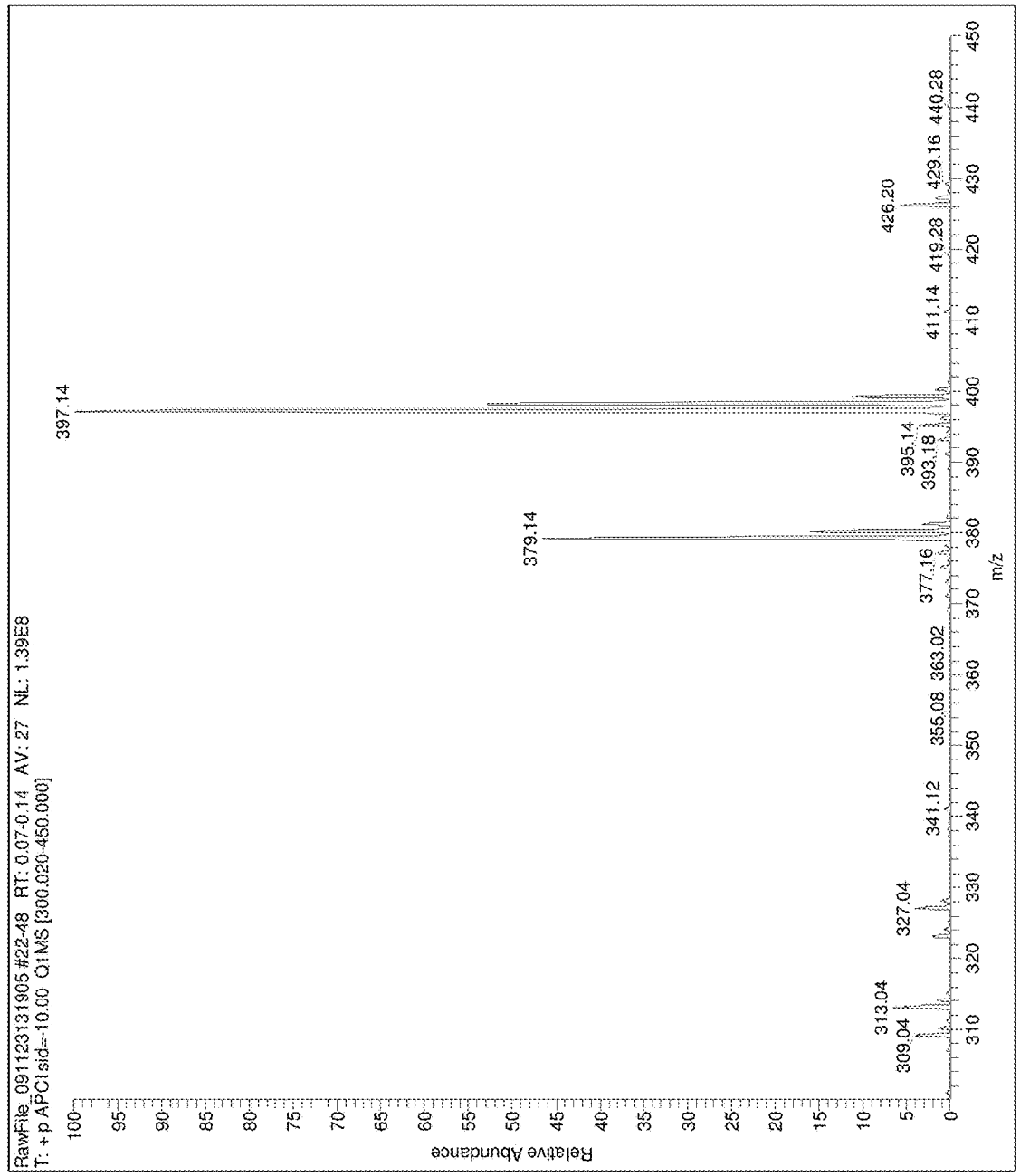
FIG. 5A shows an exemplary Q1 scan spectrum (covering the m/z range of about 300 to 450) for ionization of vitamin $D_2$.
Figure 5B:
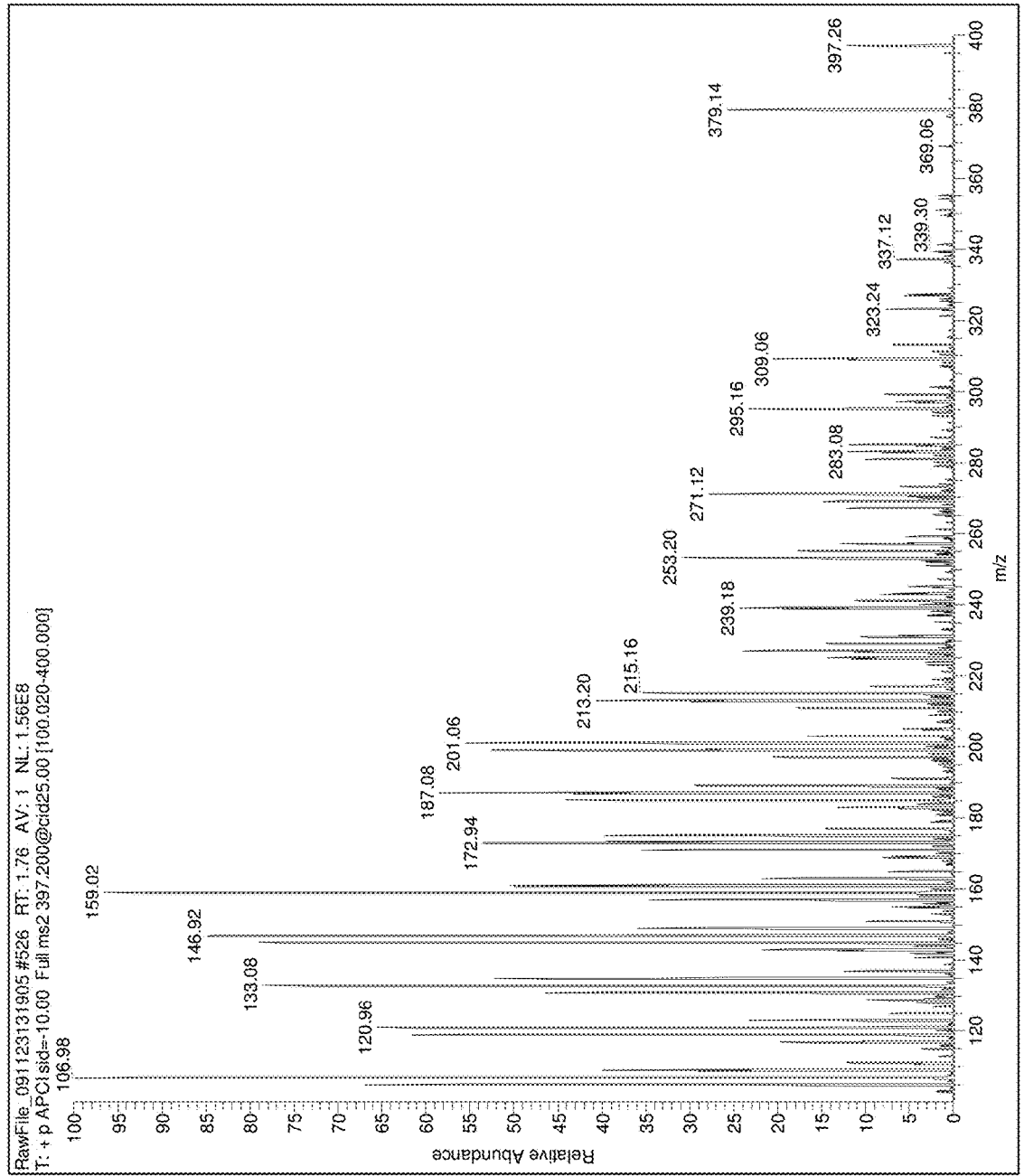
FIG. 5B shows an exemplary product ion spectra (covering the m/z range of about 100 to 400) for fragmentation of the vitamin $D_2$ precursor ion with m/z of about 397.2.
Figure 5C:
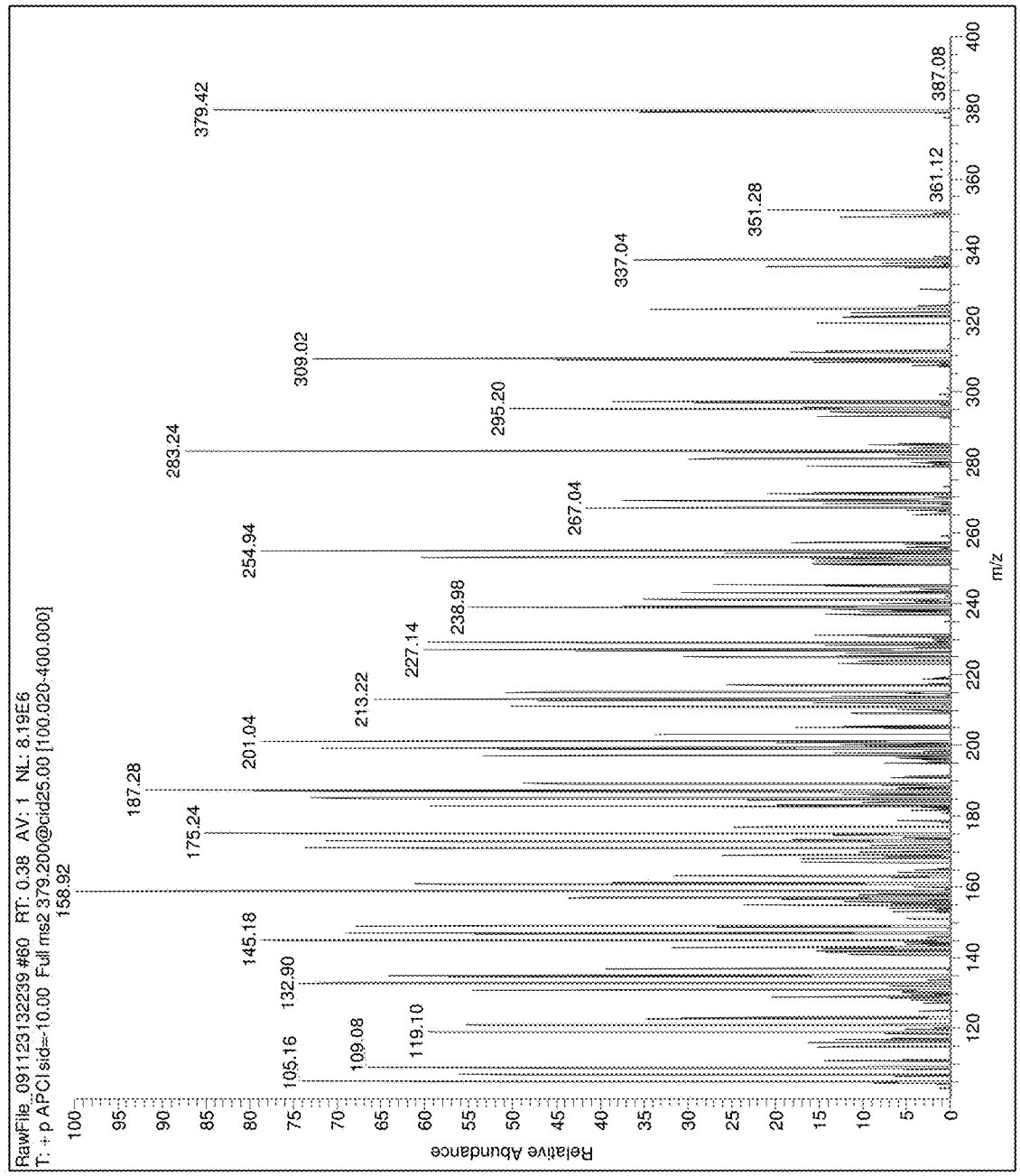
FIG. 5C shows an exemplary product ion spectra (covering the m/z range of about 100 to 400) for fragmentation of the vitamin $D_2$ precursor ion with m/z of about 379.2. Details are described in Example 14.
Figure 6A:
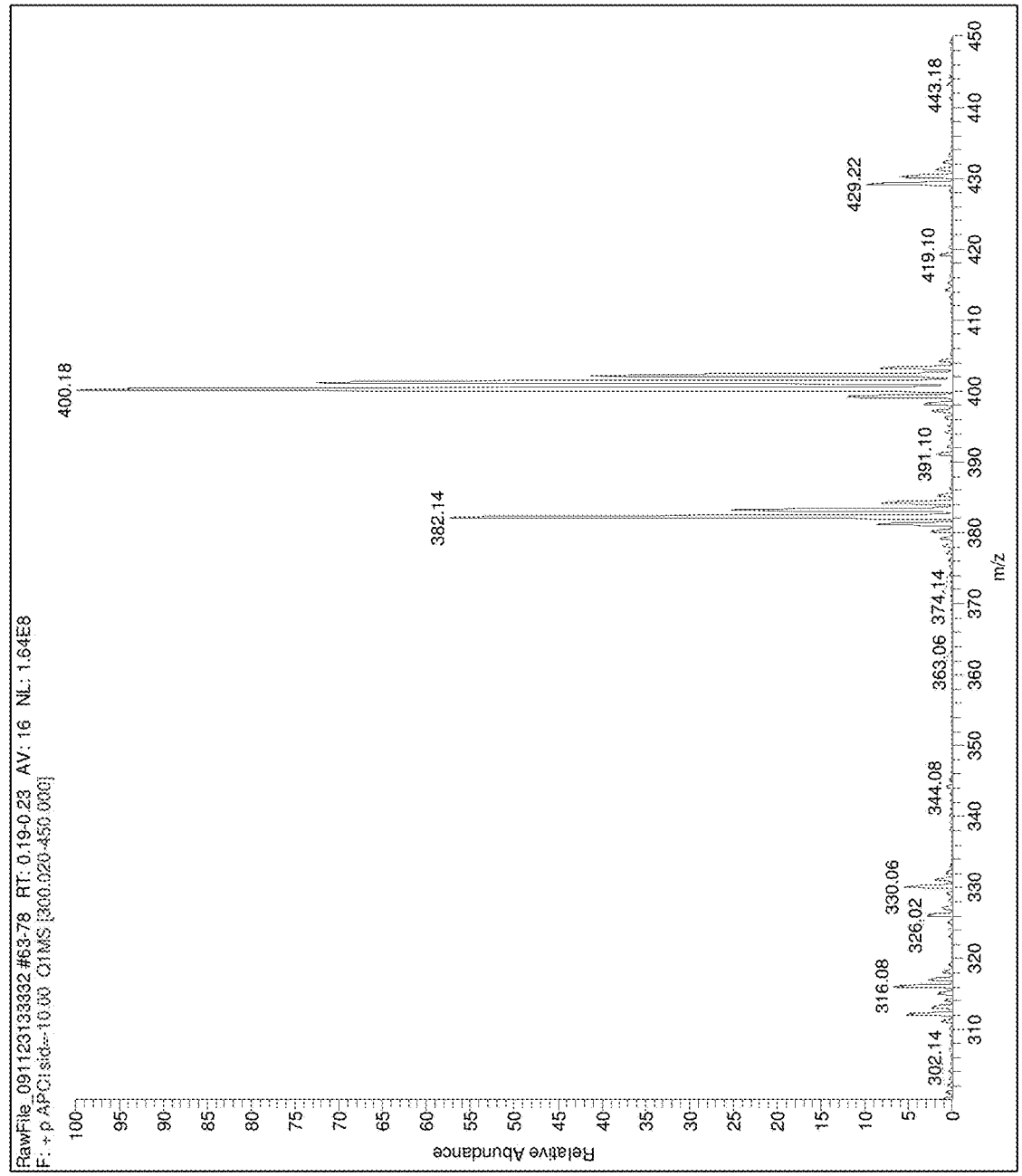
FIG. 6A shows an exemplary Q1 scan spectrum (covering the m/z range of about 300 to 450) for vitamin $D_2$-[6, 19, 19]-$^2H_3$ ions.
Figure 6B:
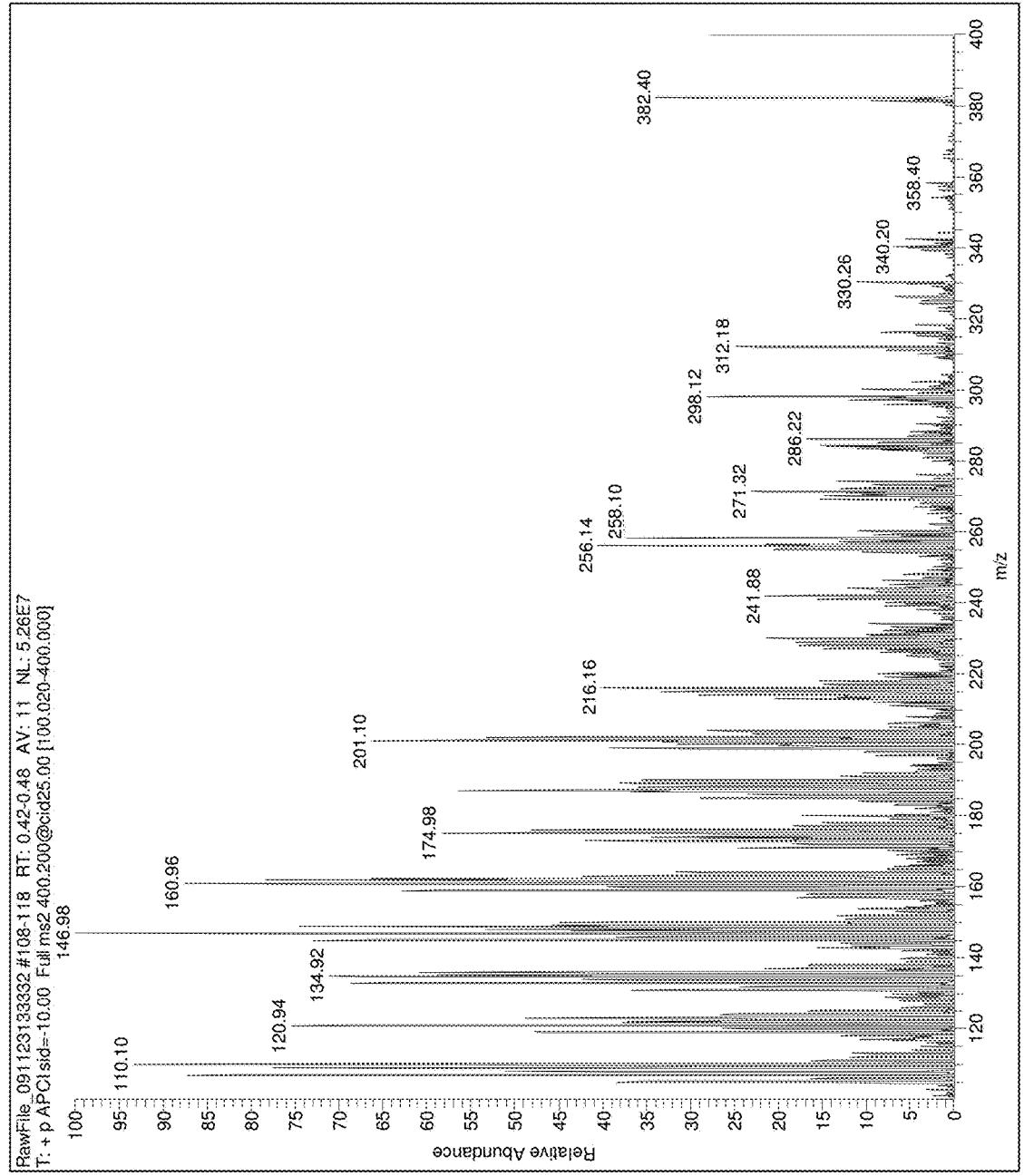
FIG. 6B shows an exemplary product ion spectra (covering the m/z range of about 100 to 400) for fragmentation of the vitamin $D_2$-[6, 19, 19]-$^2H_3$ precursor ion with m/z of about 400.2.
Figure 6C:
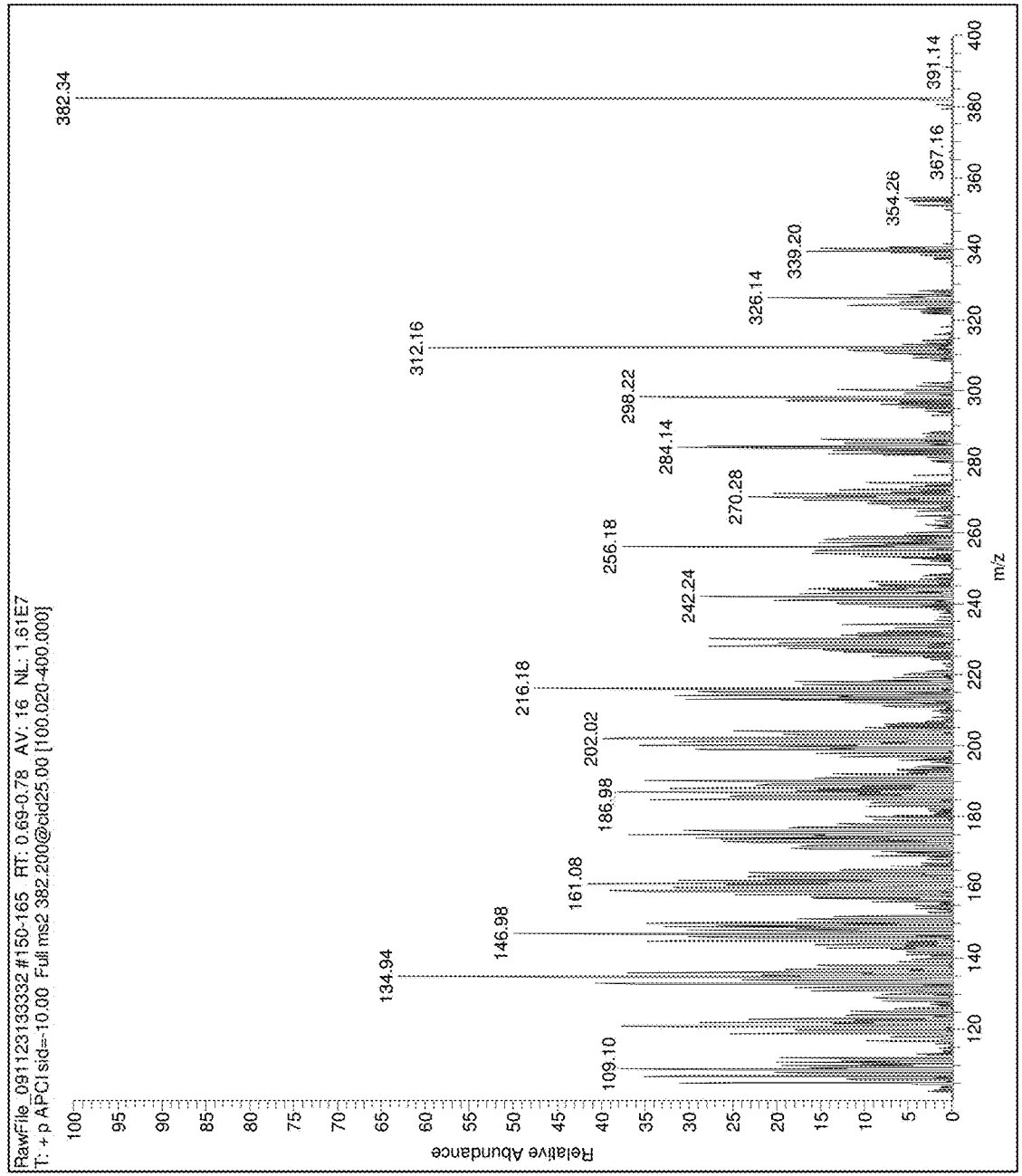
FIG. 6C shows an exemplary product ion spectra (covering the m/z range of about 100 to 400) for fragmentation of the vitamin $D_2$-[6, 19, 19]-$^2H_3$ precursor ion with m/z of about 382.2 Details are described in Example 14.
Figure 7A:
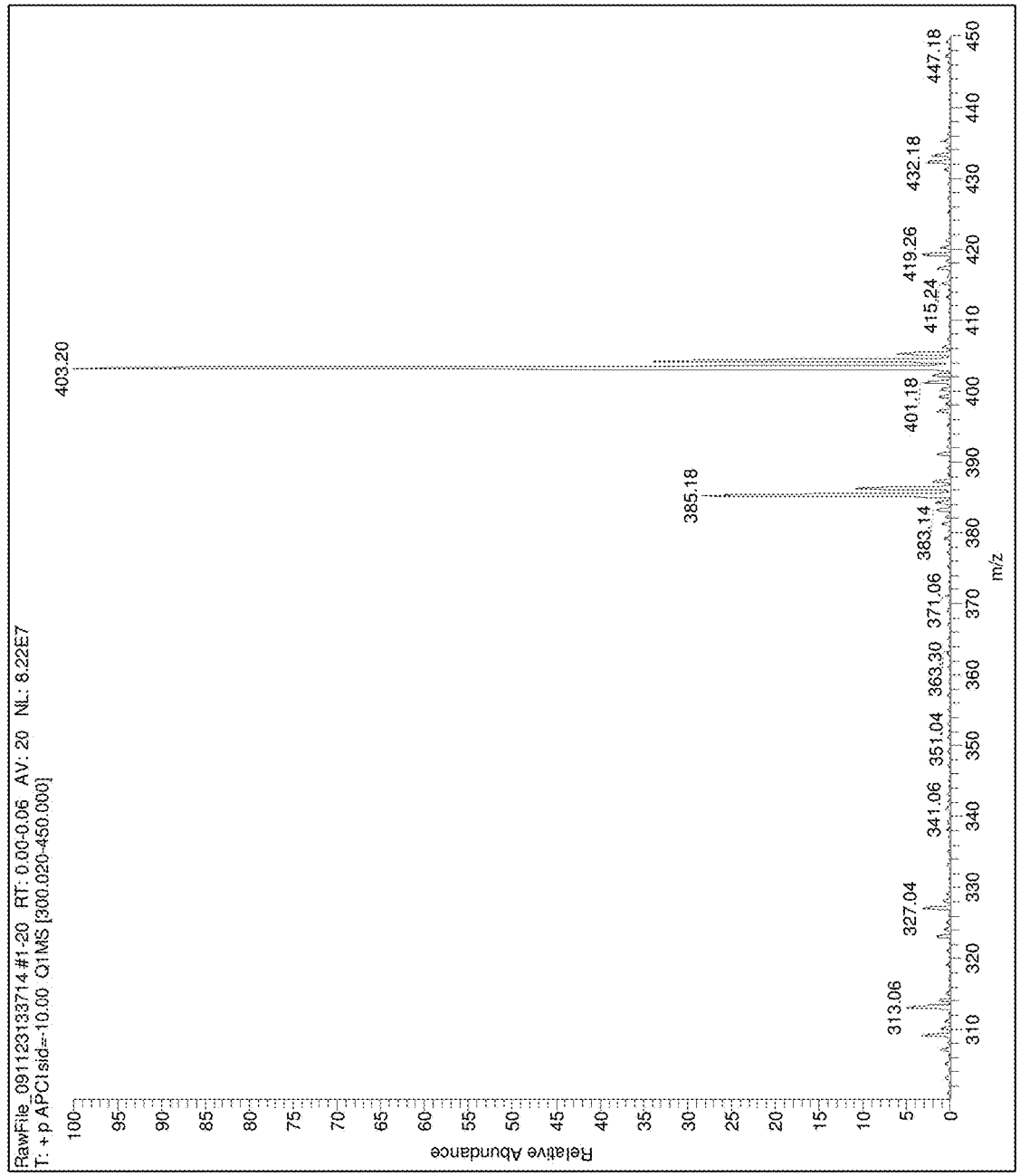
FIG. 7A shows an exemplary Q1 scan spectrum (covering the m/z range of about 300 to 450) for vitamin $D_2$-[26, 26, 26, 27, 27, 27]-$^2H_6$ ions.
Figure 7B:
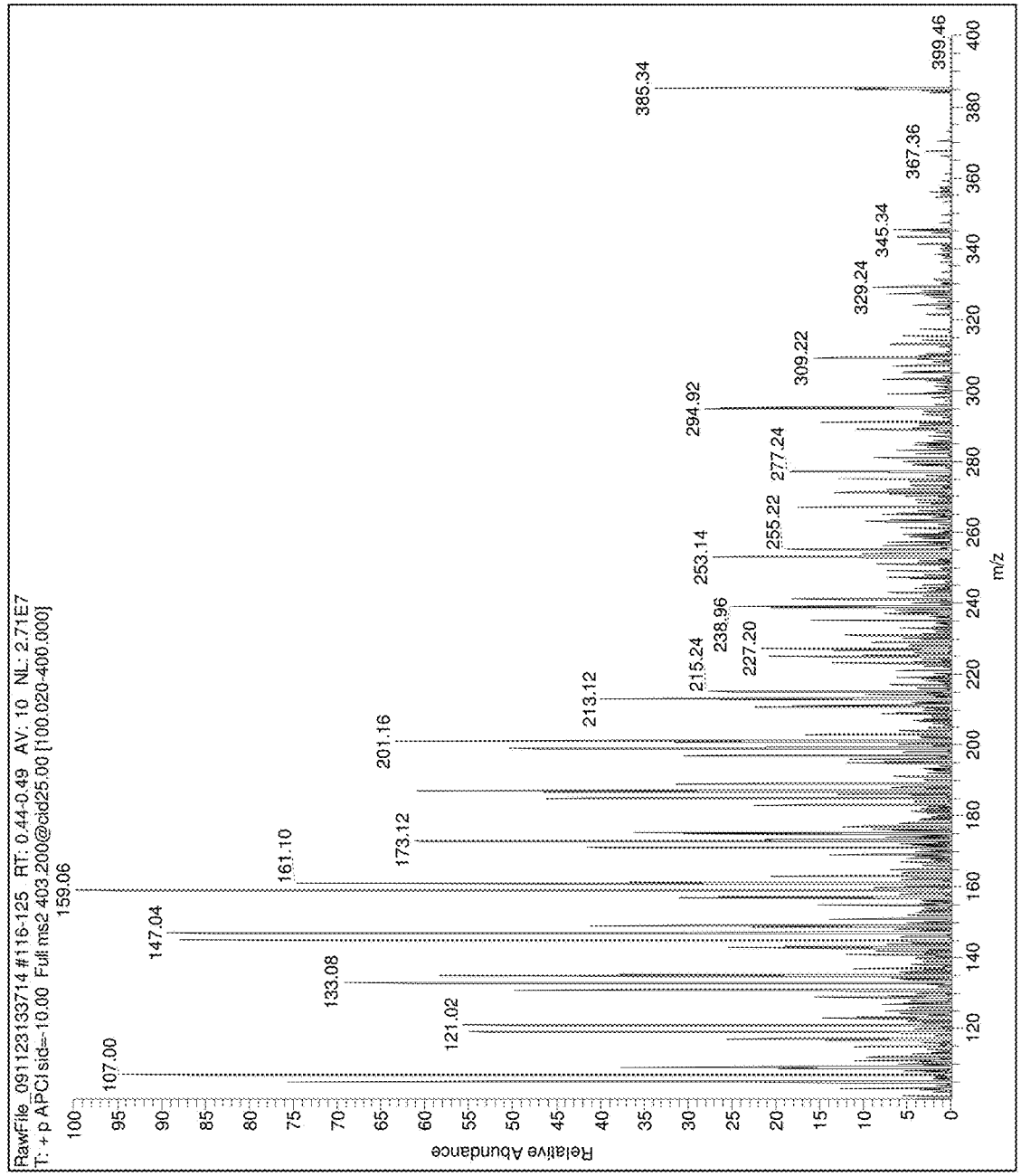
FIG. 7B shows an exemplary product ion spectra (covering the m/z range of about 100 to 400) for fragmentation of the vitamin $D_2$-[26, 26, 26, 27, 27, 27]-$^2H_6$ precursor ion with m/z of about 403.2.
Figure 7C:
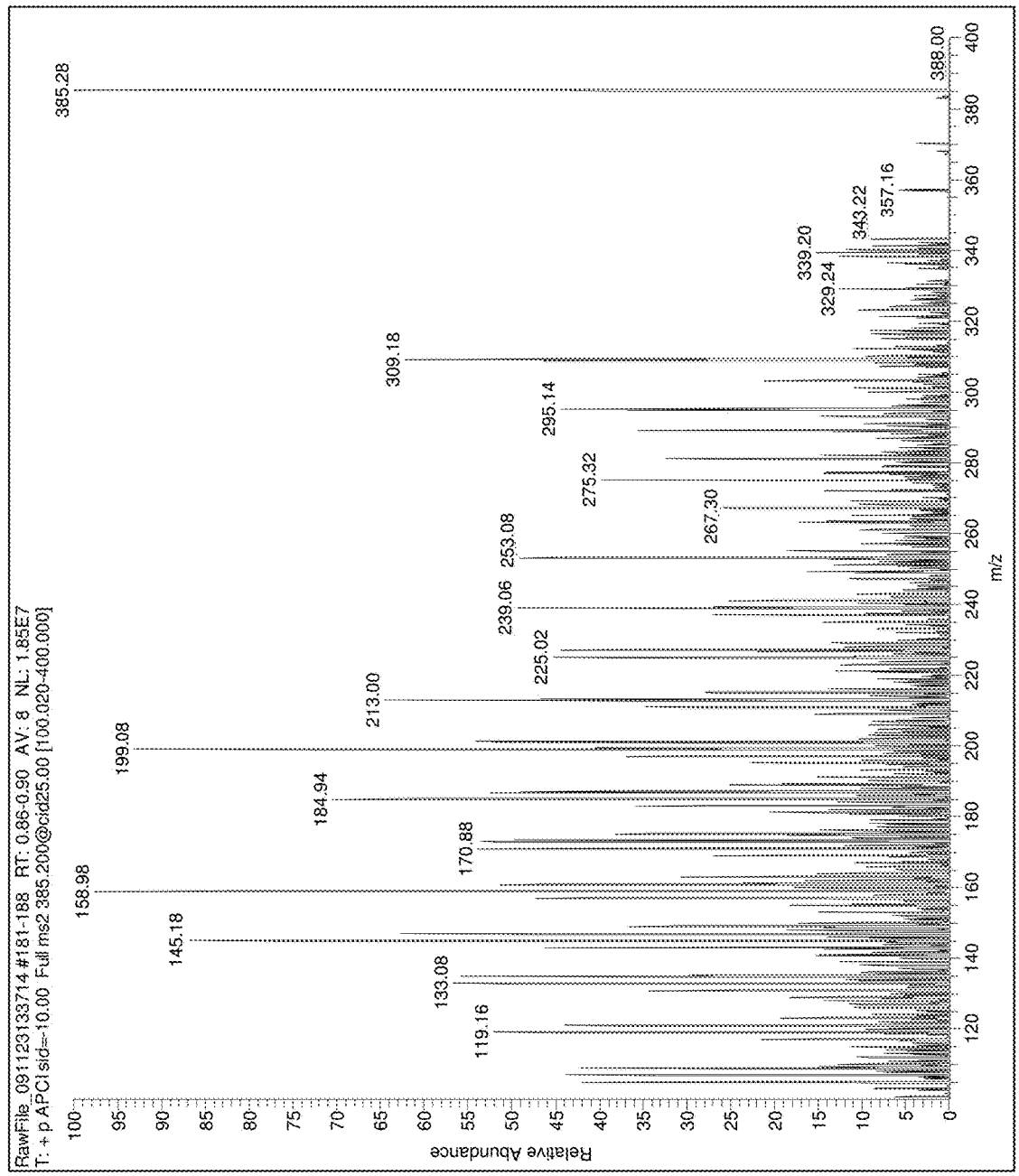
FIG. 7C shows an exemplary product ion spectra (covering the m/z range of about 100 to 400) for fragmentation of the vitamin $D_2$-[26, 26, 26, 27, 27, 27]-$^2H_6$ precursor ion with m/z of about 385.2. Details are described in Example 14.

Example 14: Exemplary Spectra from MS/MS Analysis of Vitamin $D_2$ and Vitamin $D_3$ Exemplary Q1 scan spectra from the tandem mass spectrometric analysis of vitamin $D_2$, vitamin $D_2$-[6, 19, 19]-$^2H_3$, and vitamin $D_2$-[26, 26, 26, 27, 27, 27]-$^2H_6$ are shown in FIGS. 5A, 6A, and 7A, respectively. These analyses were conducted by directly injecting standard solutions containing the analyte of interest into a Finnigan TSQ Quantum Ultra MS/MS system (Thermo Electron Corporation). A liquid chromatography mobile phase was simulated by passing 800 µL/min of 80% acetonitrile, 20% water with 0.1% formic acid through an HPLC column, upstream of introduction of the analyte. The analytes were ionized by APCI as described above. The spectra were collected by scanning Q1 across a m/z range of about 300 to 450.

Exemplary product ion scans generated from two different precursor ions for each of vitamin $D_2$, vitamin $D_2$-[6, 19, 19]-$^2H_3$, and vitamin $D_2$-[26, 26, 26, 27, 27, 27]-$^2H_6$ are presented in FIGS. 5B-C, 6B-C, and 7B-C, respectively. The precursor ions selected in Q1 and the collision energies used to generate these product ion spectra are indicated in Table 20.

Exemplary MRM transitions for the quantitation of vitamin $D_2$ include fragmenting a precursor ion with a m/z of about 397.2 to a product ion with a m/z of about 159.0; and fragmenting a precursor ion with a m/z of about 379.2 to a product ion with a m/z of about 158.9. Exemplary MRM transitions for the quantitation of vitamin $D_2$-[6, 19, 19]-$^2H_3$ include fragmenting a precursor ion with a m/z of about 400.2 to a product ion with a m/z of about 147.0; and fragmenting a precursor ion with a m/z of about 382.2 to a product ion with a m/z of about 312.2. Exemplary MRM transitions for the quantitation of vitamin $D_2$-[26, 26, 26, 27, 27, 27]-$^2H_6$ include fragmenting a precursor ion with a m/z of about 403.2 to a product ion with a m/z of about 159.1; and fragmenting a precursor ion with a m/z of about 385.2 to a product ion with a m/z of about 159.0. However, as can be seen in the product ion scans in FIGS. 5B-C, 6B-C, and 7B-C, several other product ions are generated upon fragmentation of the precursor ions. Additional product ions may be selected from those indicated in FIGS. 5B-C, 6B-C, and 7B-C to replace or augment the exemplary fragment ions. For example, additional product ions generated by fragmentation of the vitamin $D_2$ precursor ion with m/z of about 397.2 include ions with m/z of about 146.9, 133.1, and 121.0. Exemplary additional product ions generated by fragmentation of the vitamin $D_2$ precursor ion with m/z of about 379.2 include ions with m/z of about 283.2, 187.3, and 175.2.

TABLE 20

Precursor Ions and Collision Cell Energies for Fragmentation of vitamin $D_2$, vitamin $D_2$-[6,19,19]-$^2H_3$, and vitamin $D_2$-[26,26,26,27,27,27]-$^2H_6$

| Analyte | Precursor Ion (m/z) | Collision Cell Energy (V) |
|---|---|---|
| vitamin $D_2$ | 397.2, 379.2 | 25 |
| vitamin $D_2$-[6,19,19]-$^2H_3$ | 400.2, 382.2 | 25 |
| vitamin $D_2$-[26,26,26,27,27,27]-$^2H_6$ | 403.2, 385.2 | 25 |

Figure 8A:
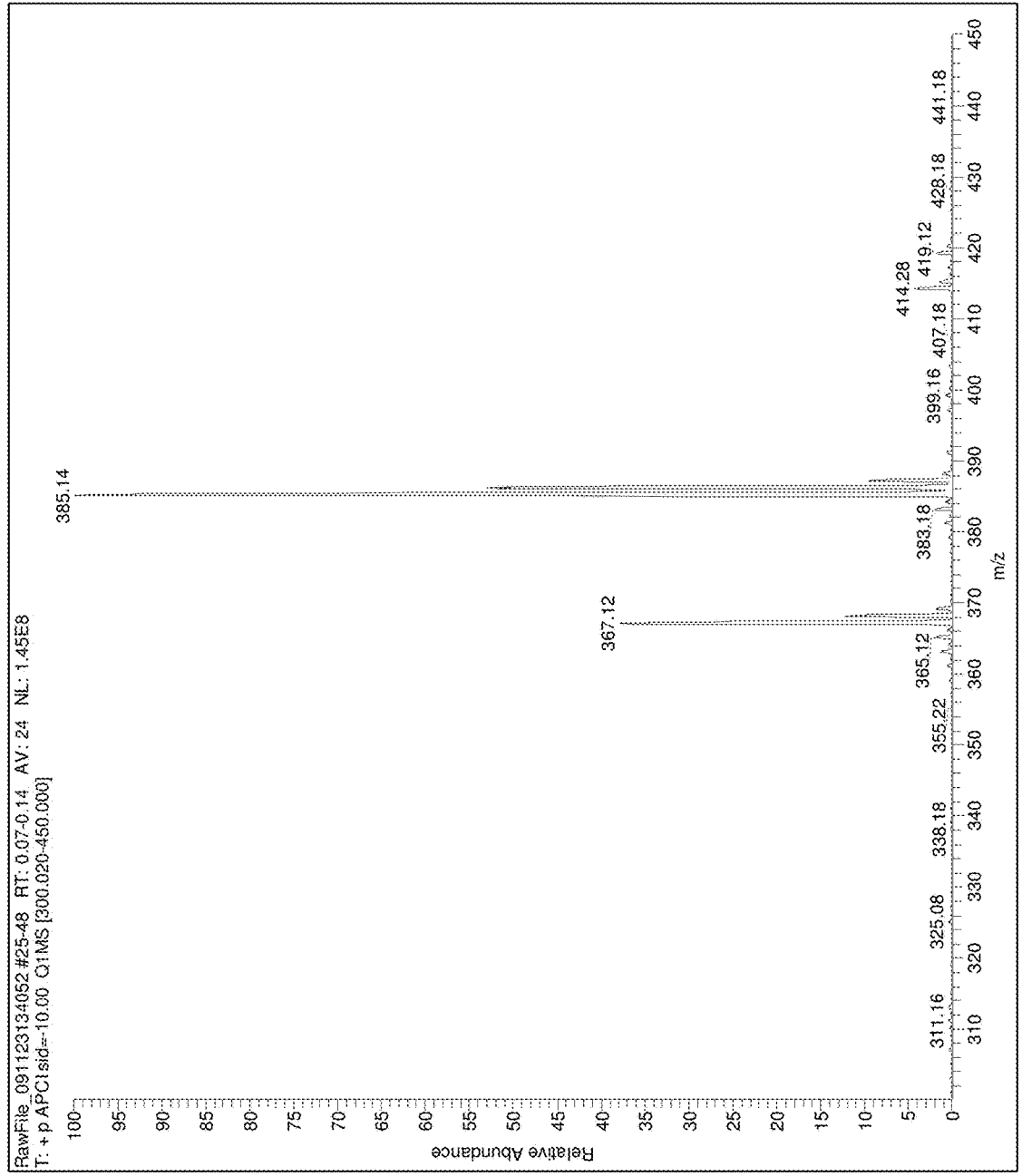
FIG. 8A shows an exemplary Q1 scan spectrum (covering the m/z range of about 300 to 450) for ionization of vitamin $D_3$.
Figure 8B:
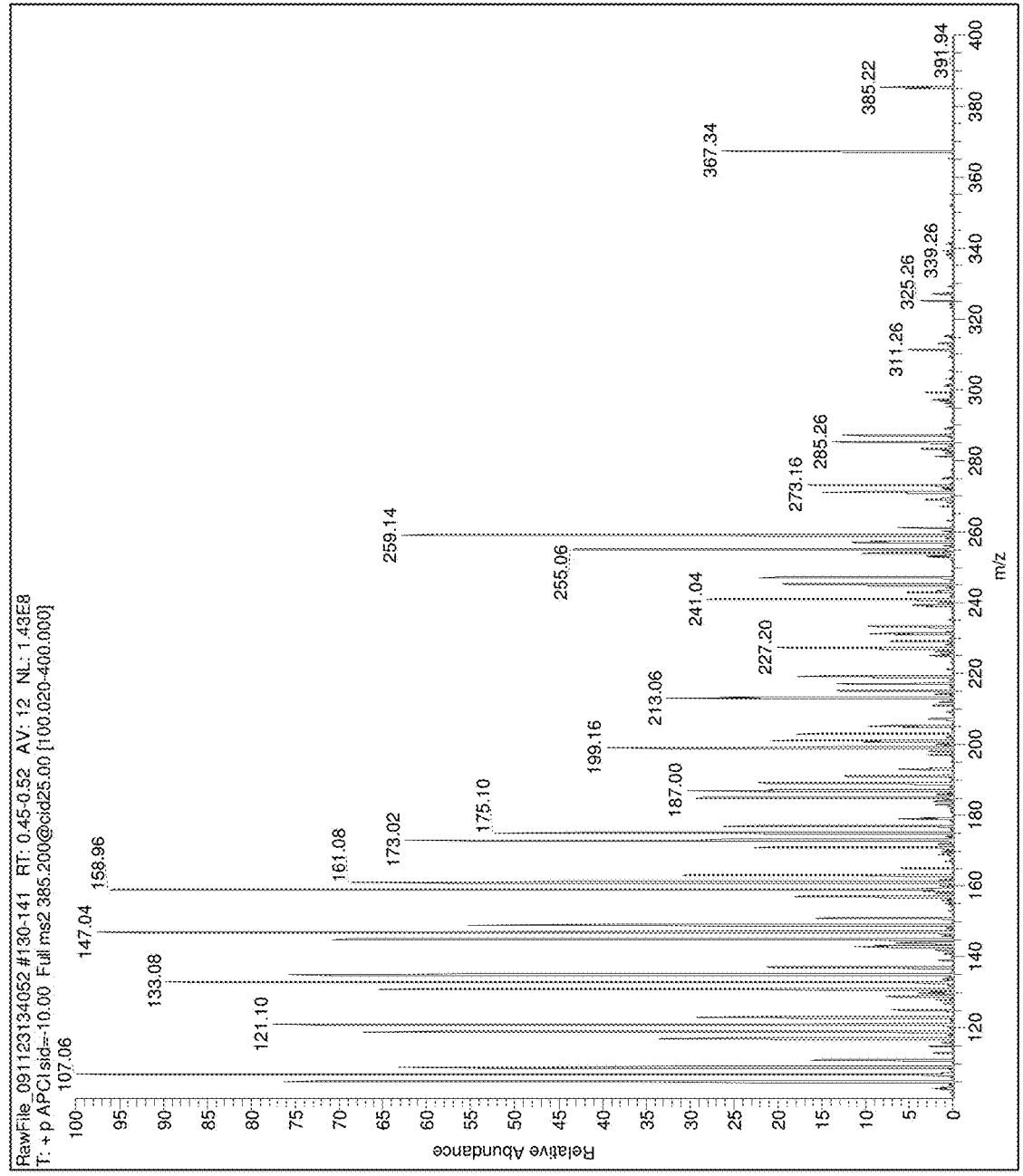
FIG. 8B shows an exemplary product ion spectra (covering the m/z range of about 100 to 400) for fragmentation of the vitamin $D_3$ precursor ion with m/z of about 385.2.
Figure 8C:
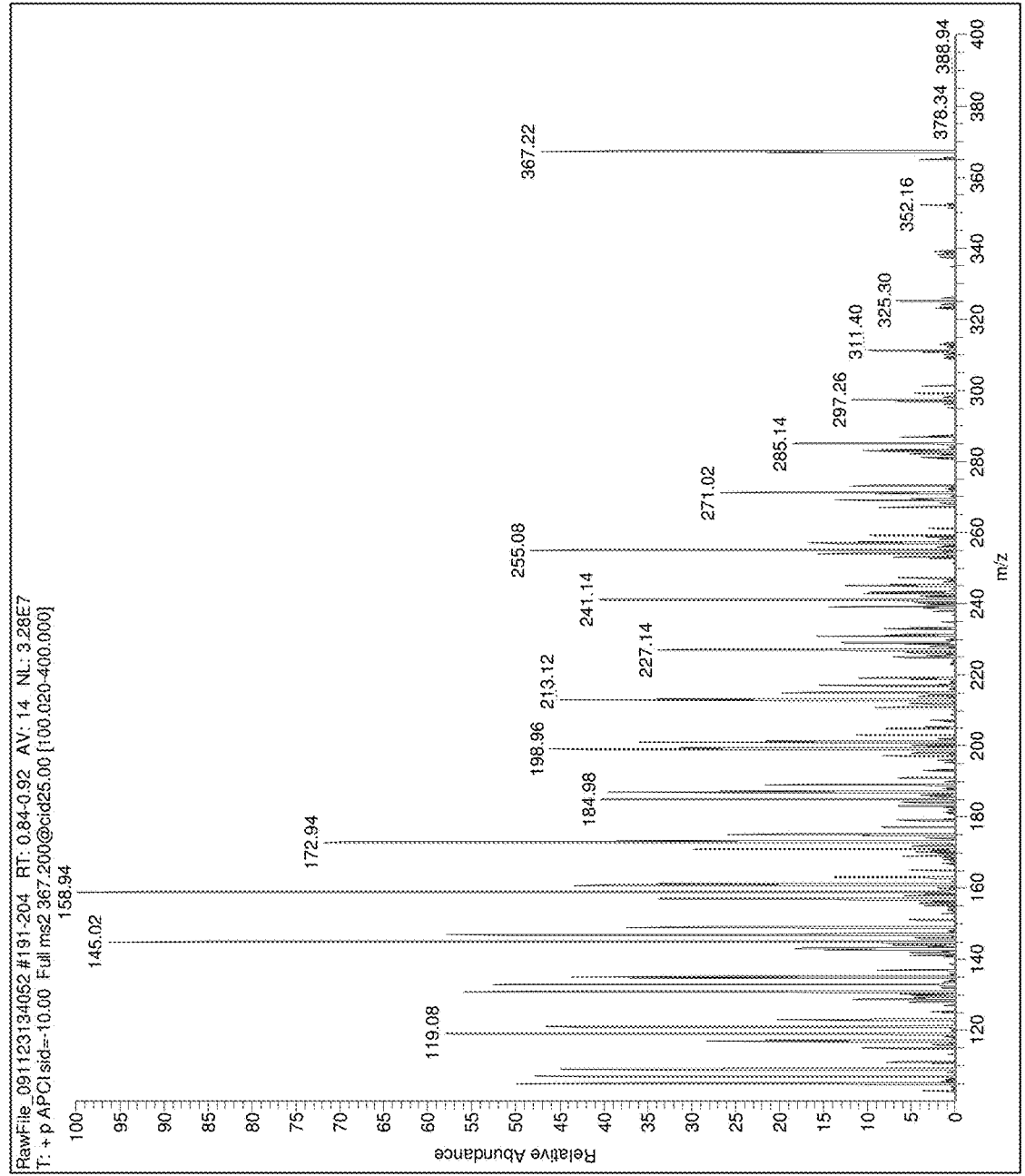
FIG. 8C shows an exemplary product ion spectra (covering the m/z range of about 100 to 400) for fragmentation of the vitamin $D_3$ precursor ion with m/z of about 367.2. Details are described in Example 14.
Figure 9A:
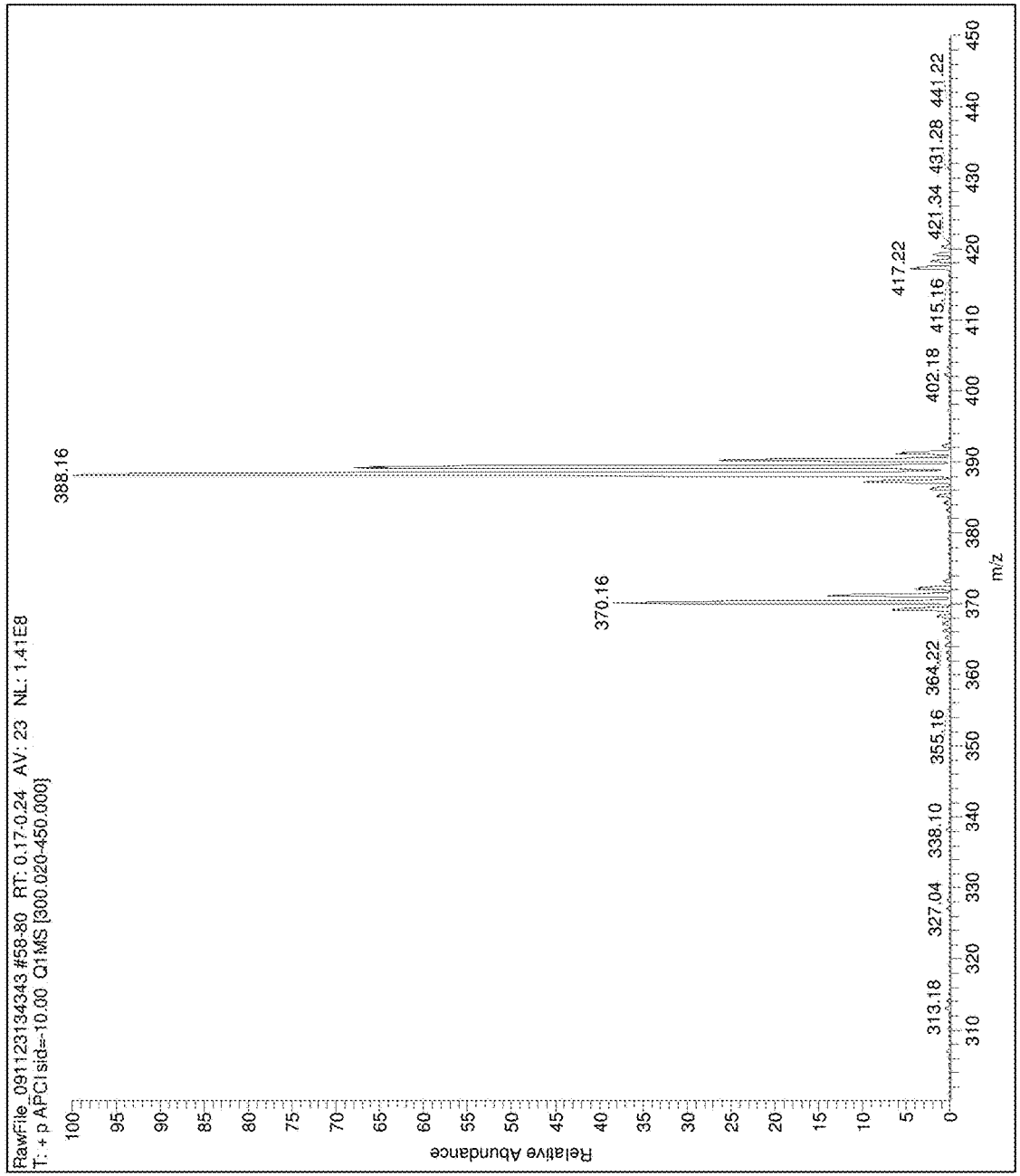
FIG. 9A shows an exemplary Q1 scan spectrum (covering the m/z range of about 300 to 450) for vitamin $D_3$-[6, 19, 19]-$^2H_3$ ions.
Figure 9B:
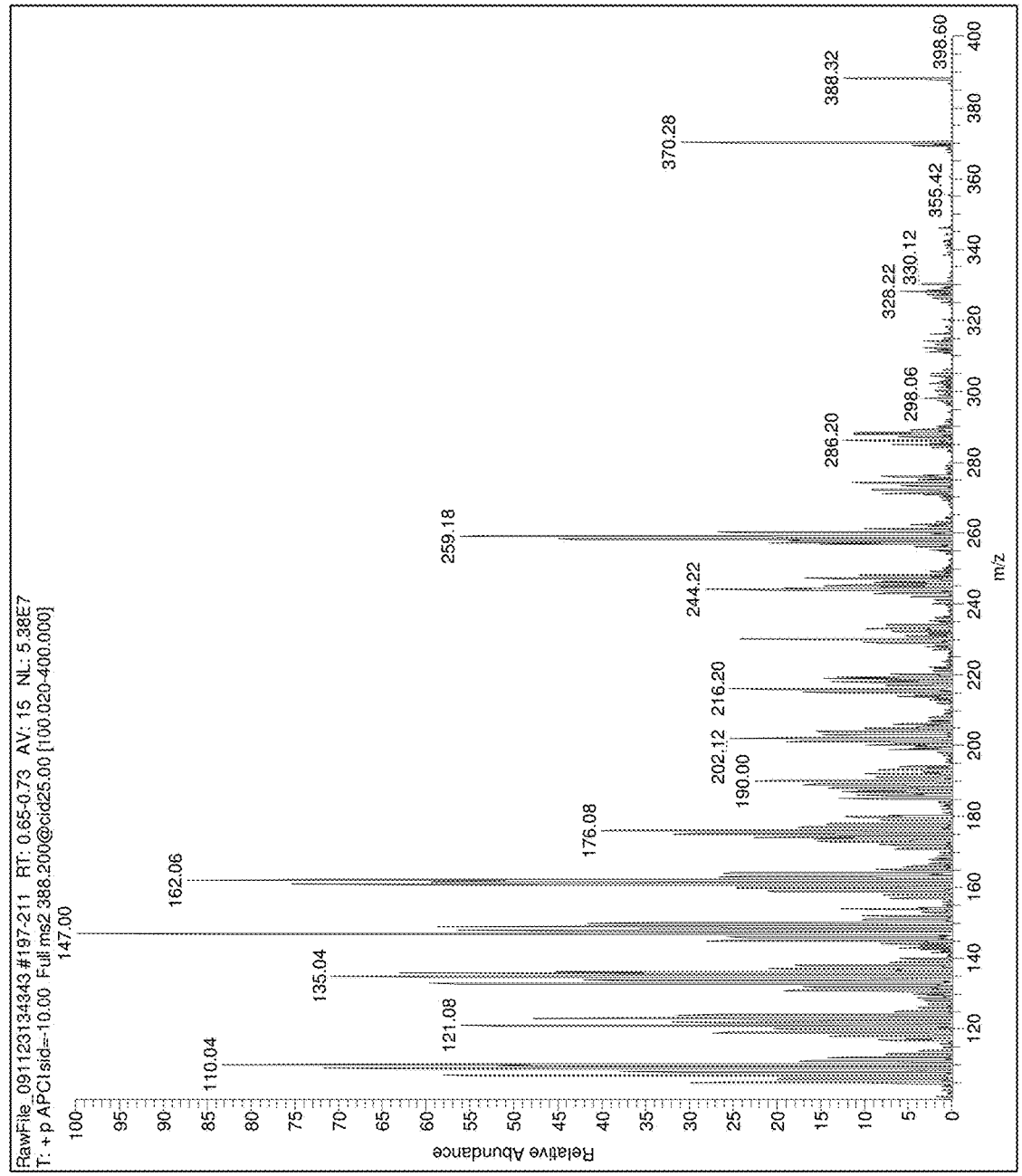
FIG. 9B shows an exemplary product ion spectra (covering the m/z range of about 100 to 400) for fragmentation of the vitamin $D_3$-[6, 19, 19]-$^2H_3$ precursor ion with m/z of about 388.2.
Figure 9C:
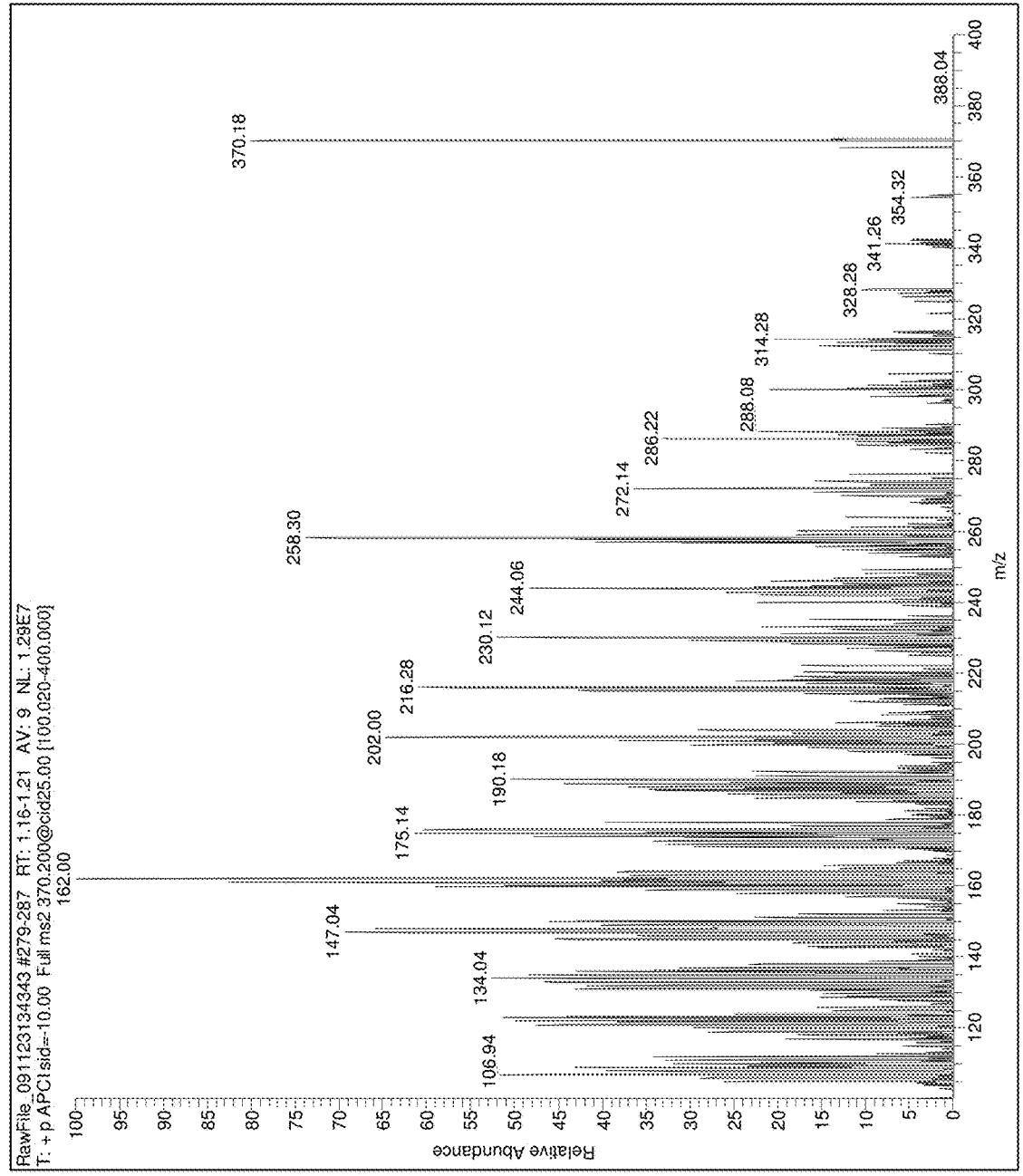
FIG. 9C shows an exemplary product ion spectra (covering the m/z range of about 100 to 400) for fragmentation of the vitamin $D_3$-[6, 19, 19]-$^2H_3$ precursor ion with m/z of about 370.2 Details are described in Example 14.
Figure 10A:
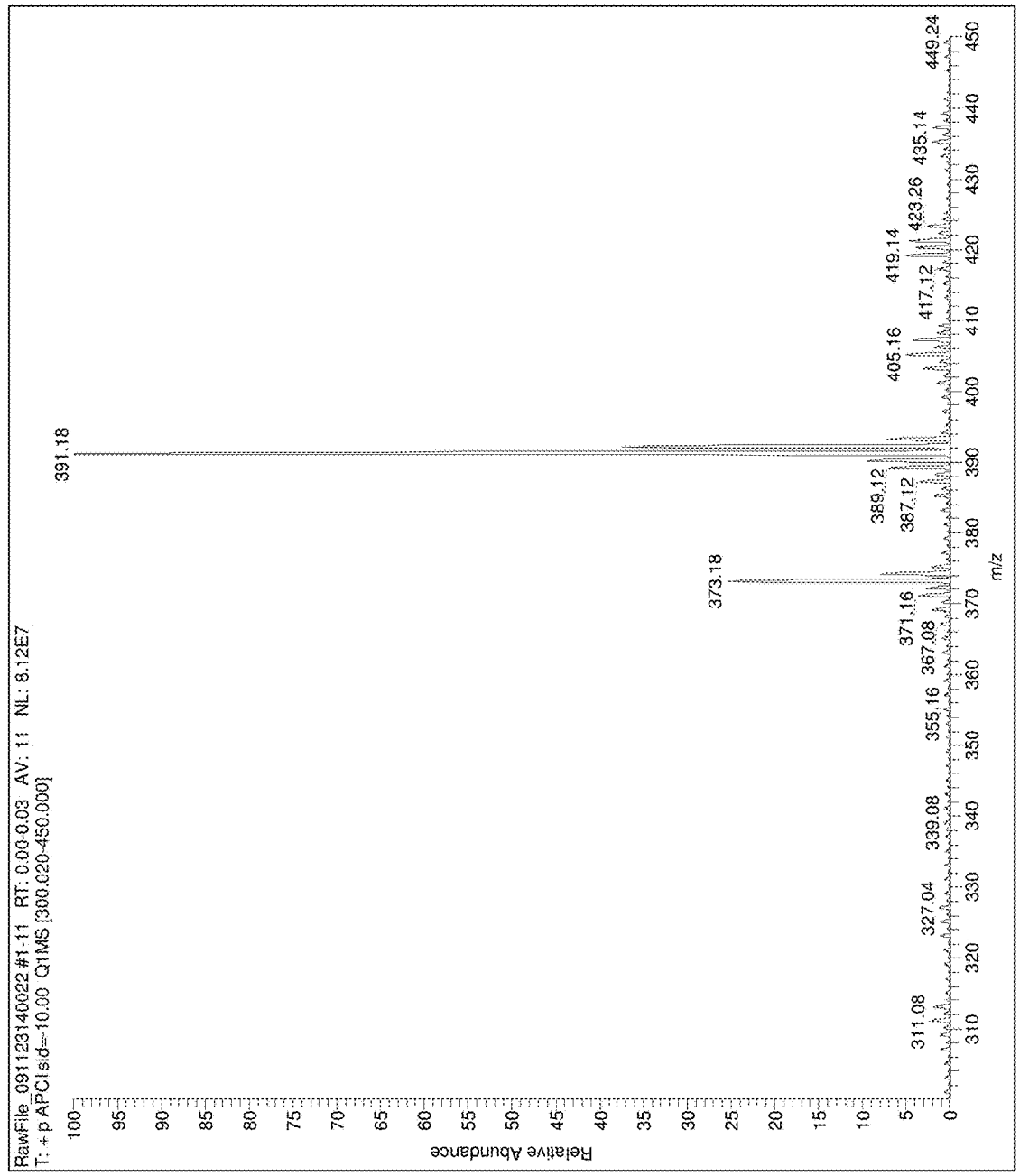
FIG. 10A shows an exemplary Q1 scan spectrum (covering the m/z range of about 300 to 450) for vitamin $D_3$-[26, 26, 26, 27, 27, 27]-$^2H_6$ ions.
Figure 10B:
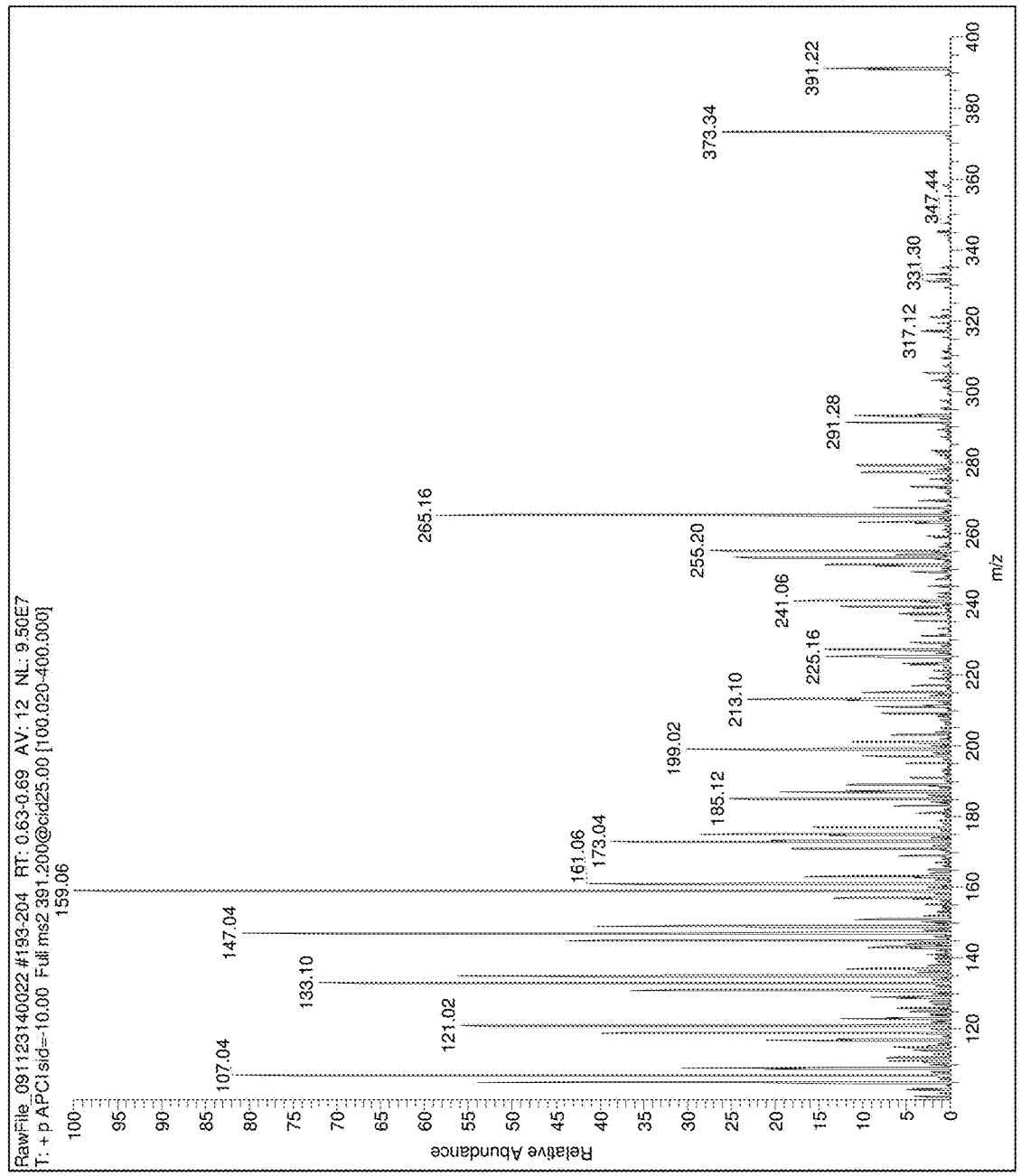
FIG. 10B shows an exemplary product ion spectra (covering the m/z range of about 100 to 400) for fragmentation of the vitamin $D_3$-[26, 26, 26, 27, 27, 27]-$^2H_6$ precursor ion with m/z of about 391.2.
Figure 10C:
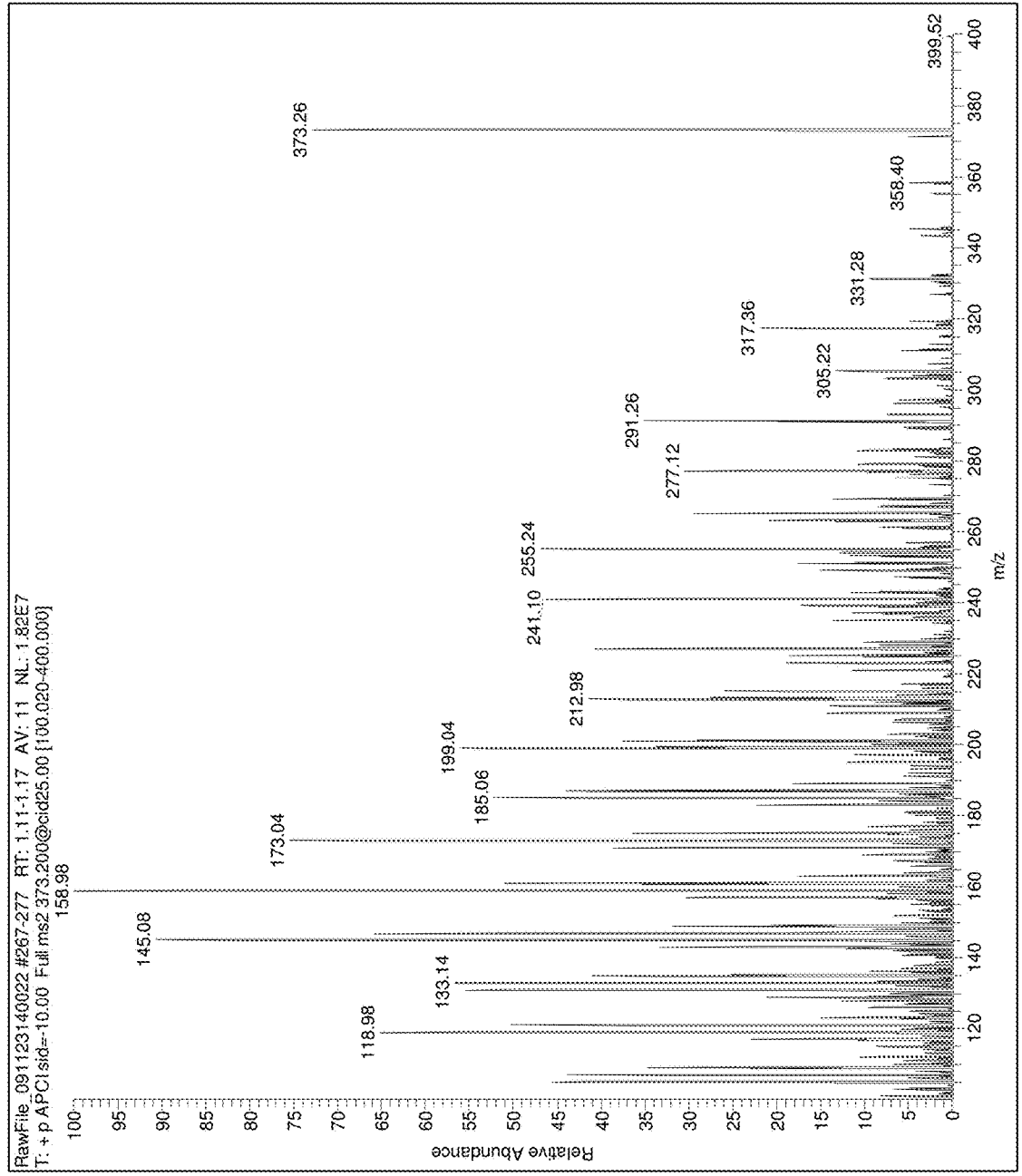
FIG. 10C shows an exemplary product ion spectra (covering the m/z range of about 100 to 400) for fragmentation of the vitamin $D_3$-[26, 26, 26, 27, 27, 27]-$^2H_6$ precursor ion with m/z of about 373.2. Details are described in Example 14.

Exemplary Q1 scan spectra from the tandem mass spectrometric analysis of vitamin $D_3$, vitamin $D_3$-[6, 19, 19]-$^2H_3$, and vitamin $D_3$-[26, 26, 26, 27, 27, 27]-$^2H_6$ are shown in FIGS. 8A, 9A, and 10A, respectively. These analyses were conducted by directly injecting standard solutions containing the analyte of interest into a Finnigan TSQ Quantum Ultra MS/MS system (Thermo Electron Corporation). A liquid chromatography mobile phase was simulated by passing 800 µL/min of 80% acetonitrile, 20% water with 0.1% formic acid through an HPLC column, upstream of introduction of the analyte. The spectra were collected by scanning Q1 across a m/z range of about 300 to 450.

Exemplary product ion scans generated from two different precursor ions for each of vitamin $D_3$, vitamin $D_3$-[6, 19, 19]-$^2H_3$, and vitamin $D_3$-[26, 26, 26, 27, 27, 27]-$^2H_6$ are presented in FIGS. 8B-C, 9B-C, and 10B-C, respectively. The precursor ions selected in Q1 and the collision energies used to generate these product ion spectra are indicated in Table 21.

Exemplary MRM transitions for the quantitation of vitamin $D_3$ include fragmenting a precursor ion with a m/z of about 385.2 to a product ion with a m/z of about 147.0; and fragmenting a precursor ion with a m/z of about 367.2 to a product ion with a m/z of about 159.0. Exemplary MRM transitions for the quantitation of vitamin $D_3$-[6, 19, 19]-$^2H_3$ include fragmenting a precursor ion with a m/z of about 388.2 to a product ion with a m/z of about 147.0; and fragmenting a precursor ion with a m/z of about 370.2 to a product ion with a m/z of about 162.0. Exemplary MRM transitions for the quantitation of vitamin $D_3$-[26, 26, 26, 27, 27, 27]-$^2H_6$ include fragmenting a precursor ion with a m/z of about 391.2 to a product ion with a m/z of about 159.1; and fragmenting a precursor ion with a m/z of about 373.2 to a product ion with a m/z of about 159.0. However, as can be seen in the product ion scans in FIGS. 8B-C, 9B-C, and 10B-C, several other product ions are generated upon fragmentation of the precursor ions. Additional product ions may be selected from those indicated in FIGS. 8B-C, 9B-C, and 10B-C to replace or augment the exemplary fragment ions. For example, additional product ions generated by fragmentation of the vitamin $D_3$ precursor ion with m/z of about 385.2 include ions with m/z of about 159.0, 133.1, and 107.1. Exemplary additional product ions generated by fragmentation of the vitamin $D_3$ precursor ion with m/z of about 367.2 include ions with m/z of about 172.9, 145.0, and 119.1.

TABLE 21

Precursor Ions and Collision Cell Energies
for Fragmentation of vitamin
$D_3$, vitamin $D_3$-[6,19,19]-$^2H_3$,
and vitamin $D_3$-[26,26,26,27,27,27]-$^2H_6$

| Analyte | Precursor Ion (m/z) | Collision Cell Energy (V) |
|---|---|---|
| vitamin $D_3$ | 385.2, 367.2 | 25 |
| vitamin $D_3$-[6,19,19]-$^2H_3$ | 388.2, 370.2 | 25 |
| vitamin $D_3$-[26,26,26,27,27,27]-$^2H_6$ | 391.2, 373.2 | 25 |

Example 15: Exemplary Spectra from MS/MS Analysis of PTAD Derivatized Vitamin $D_2$ and Vitamin $D_3$ PTAD derivatives of vitamin $D_2$, vitamin $D_2$-[6, 19, 19]-$^2H_3$, vitamin $D_2$-[26, 26, 26, 27, 27, 27]-$^2H_6$, vitamin $D_3$, vitamin $D_3$-[6, 19, 19]-$^2H_3$, and vitamin $D_3$-[26, 26, 26, 27, 27, 27]-$^2H_6$ were prepared by treating aliquots of stock solutions of each analyte with PTAD in acetonitrile. The derivatization reactions was allowed to proceed for approximately one hour, and were quenched by adding water to the reaction mixture. The derivatized analytes were then analyzed according to the procedure outlined above in Examples 2-3.

Figure 11A:
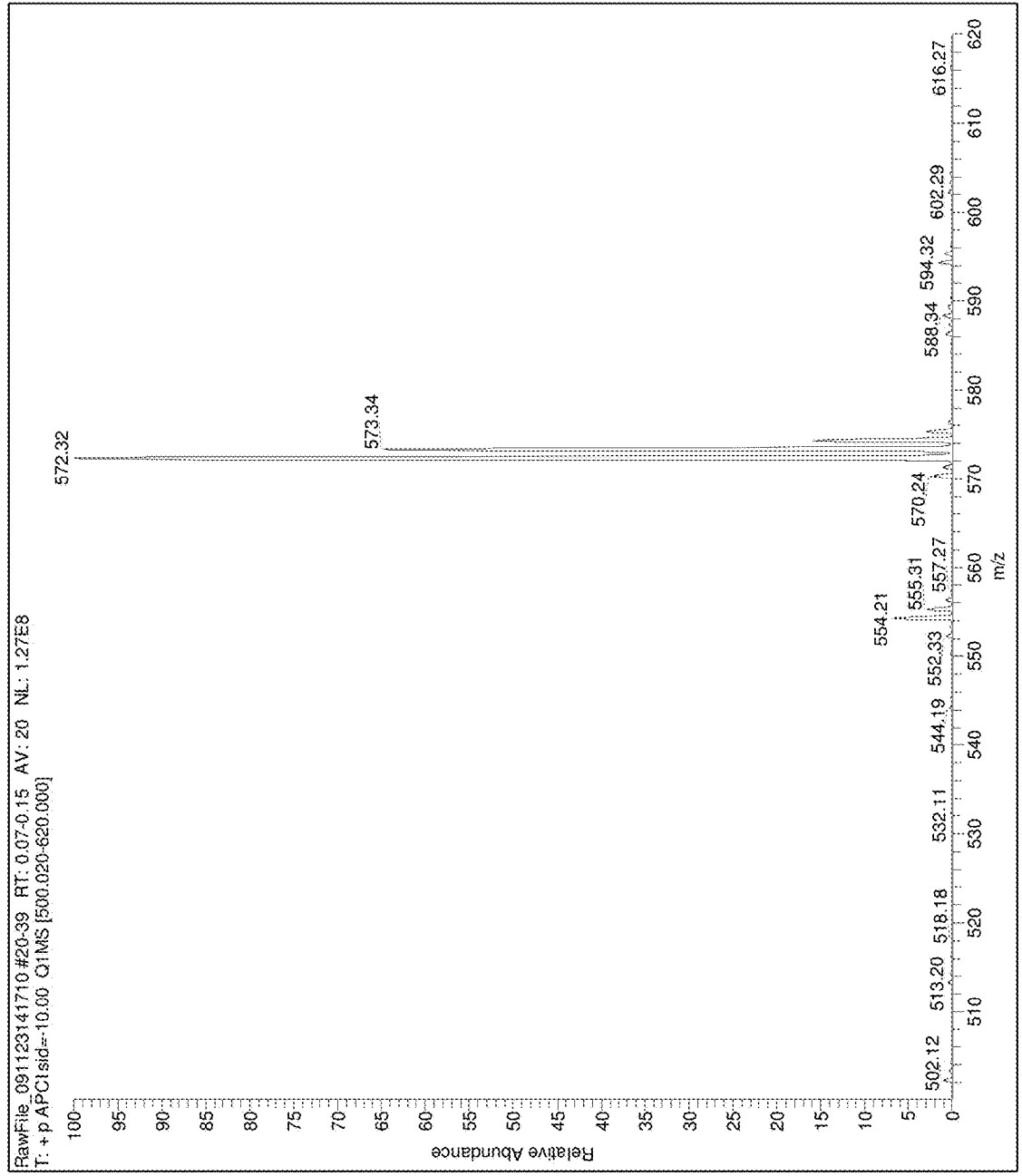
FIG. 11A shows an exemplary Q1 scan spectrum (covering the m/z range of about 500 to 620) for PTAD-vitamin $D_2$ ions.
Figure 12A:
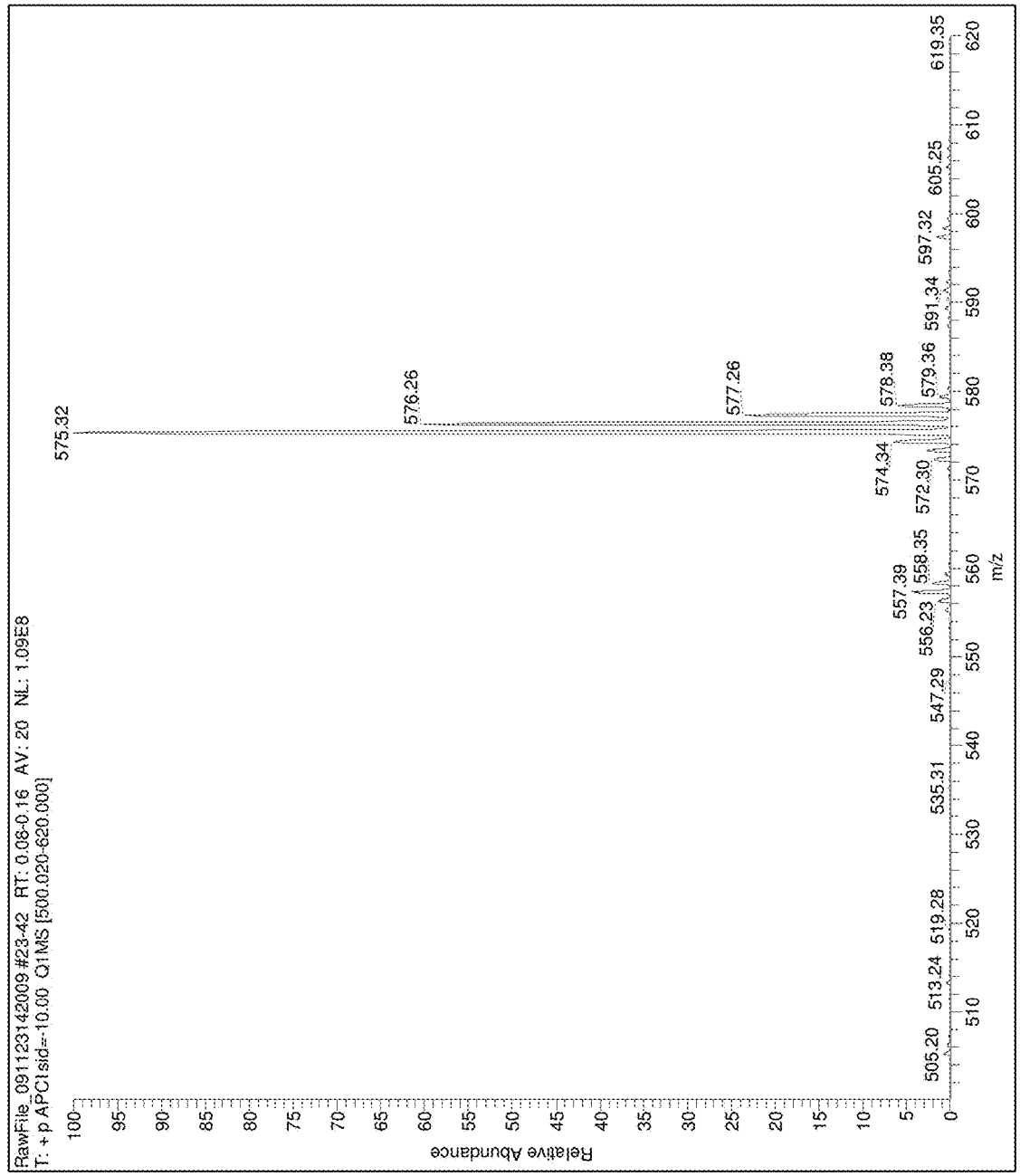
FIG. 12A shows an exemplary Q1 scan spectrum (covering the m/z range of about 500 to 620) for PTAD-vitamin $D_2$-[6, 19, 19]-$^2H_3$ ions.
Figure 13A:
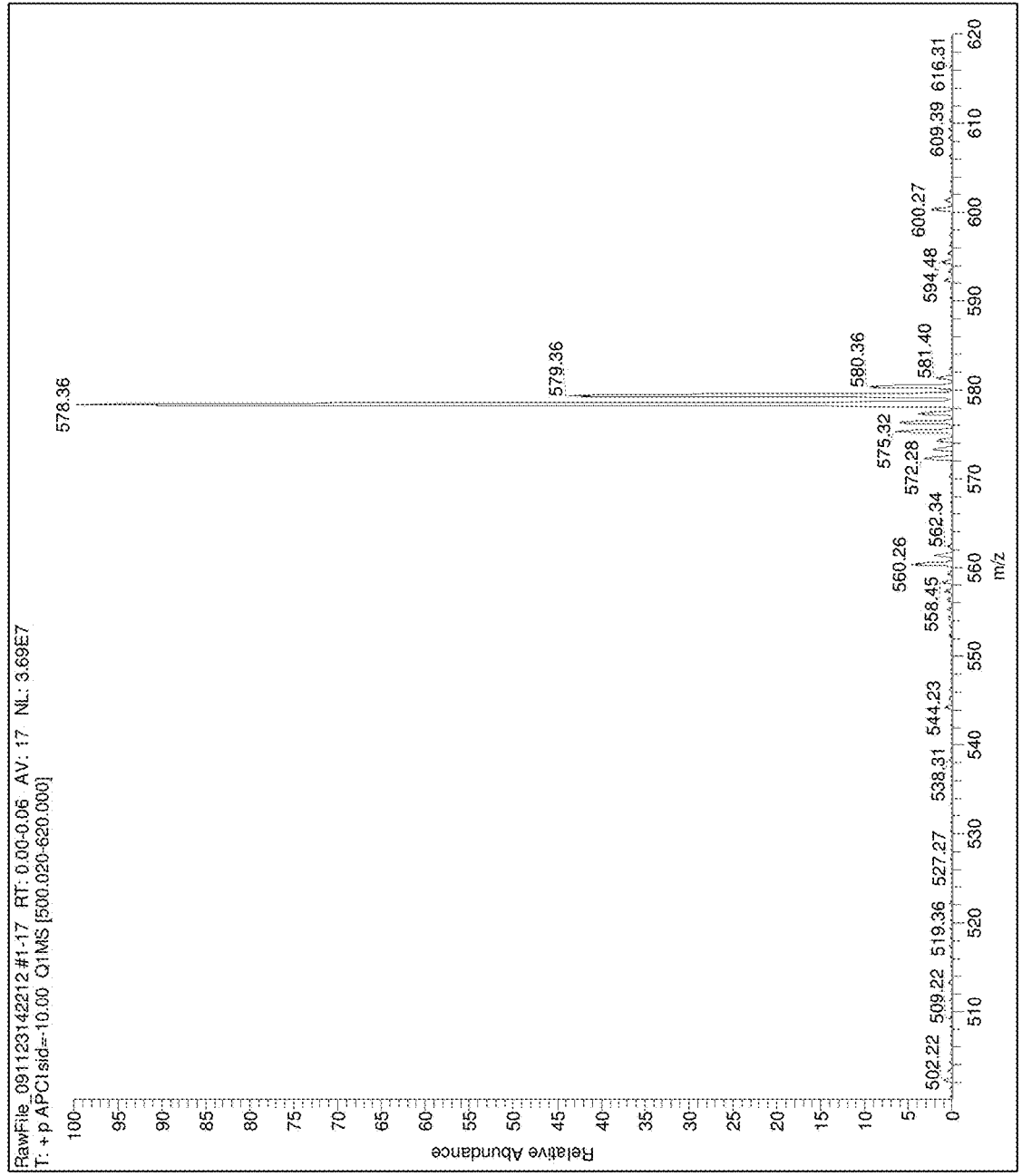
FIG. 13A shows an exemplary Q1 scan spectrum (covering the m/z range of about 500 to 620) for PTAD-vitamin $D_2$-[26, 26, 26, 27, 27, 27]-$^2H_6$ ions.

Exemplary Q1 scan spectra from the analysis of samples containing PTAD-vitamin $D_2$, PTAD-vitamin $D_2$-[6, 19, 19]-$^2H_3$, and PTAD-vitamin $D_2$-[26, 26, 26, 27, 27, 27]-$^2H_6$ are shown in FIGS. 11A, 12A, and 13A, respectively. These analyses were conducted by directly injecting standard solutions containing the analyte of interest into a Finnigan TSQ Quantum Ultra MS/MS system (Thermo Electron Corporation). A liquid chromatography mobile phase was simulated by passing 800 µL/min of 80% acetonitrile, 20% water with 0.1% formic acid through an HPLC column, upstream of introduction of the analyte. The analytes were ionized by APCI as described above. The spectra were collected by scanning Q1 across a m/z range of about 500 to 620.

Figure 11B:
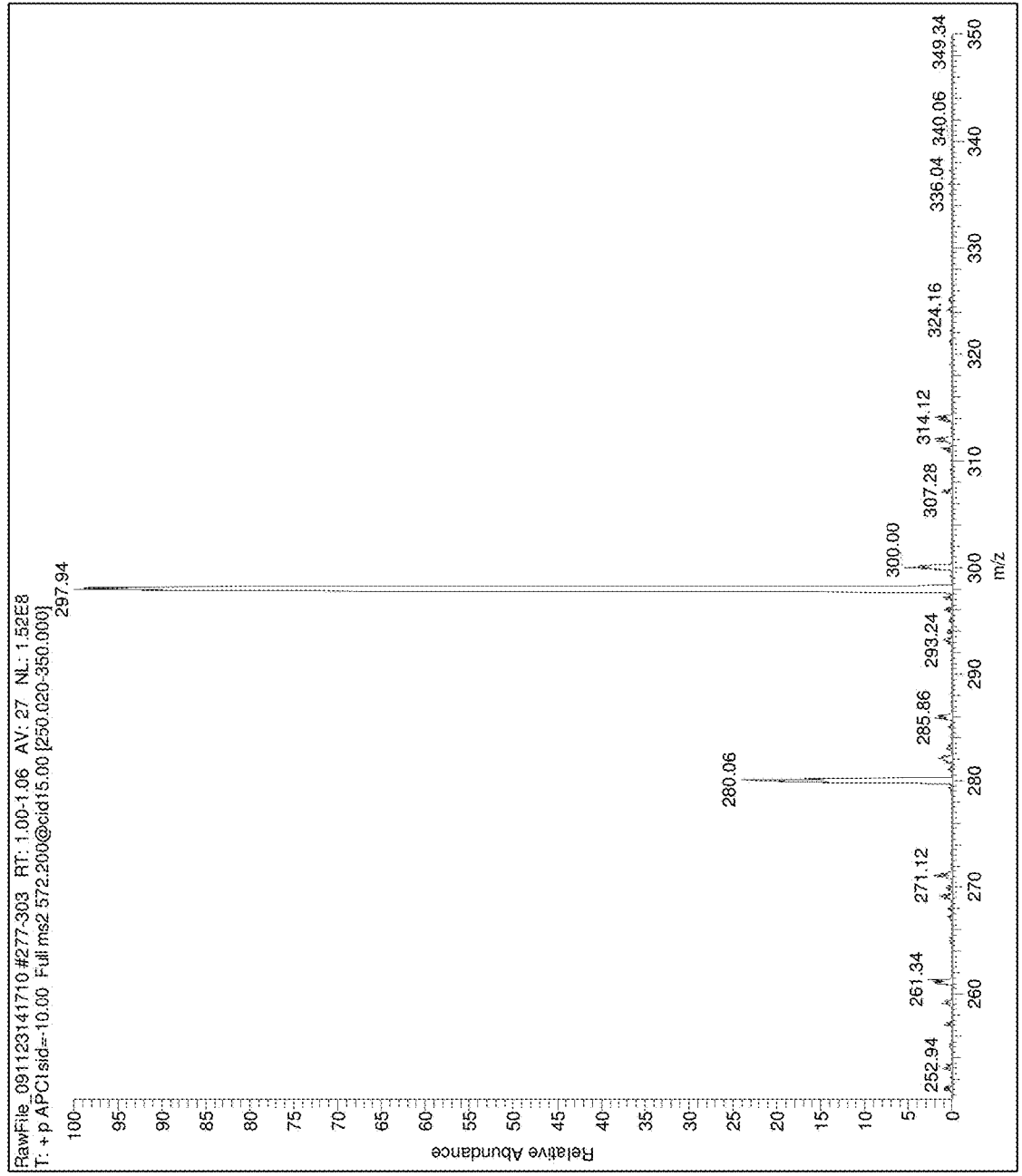
FIG. 11B shows an exemplary product ion spectra (covering the m/z range of about 250 to 350) for fragmentation of the PTAD-vitamin $D_2$ precursor ion with m/z of about 572.2. Details are described in Example 15.
Figure 12B:
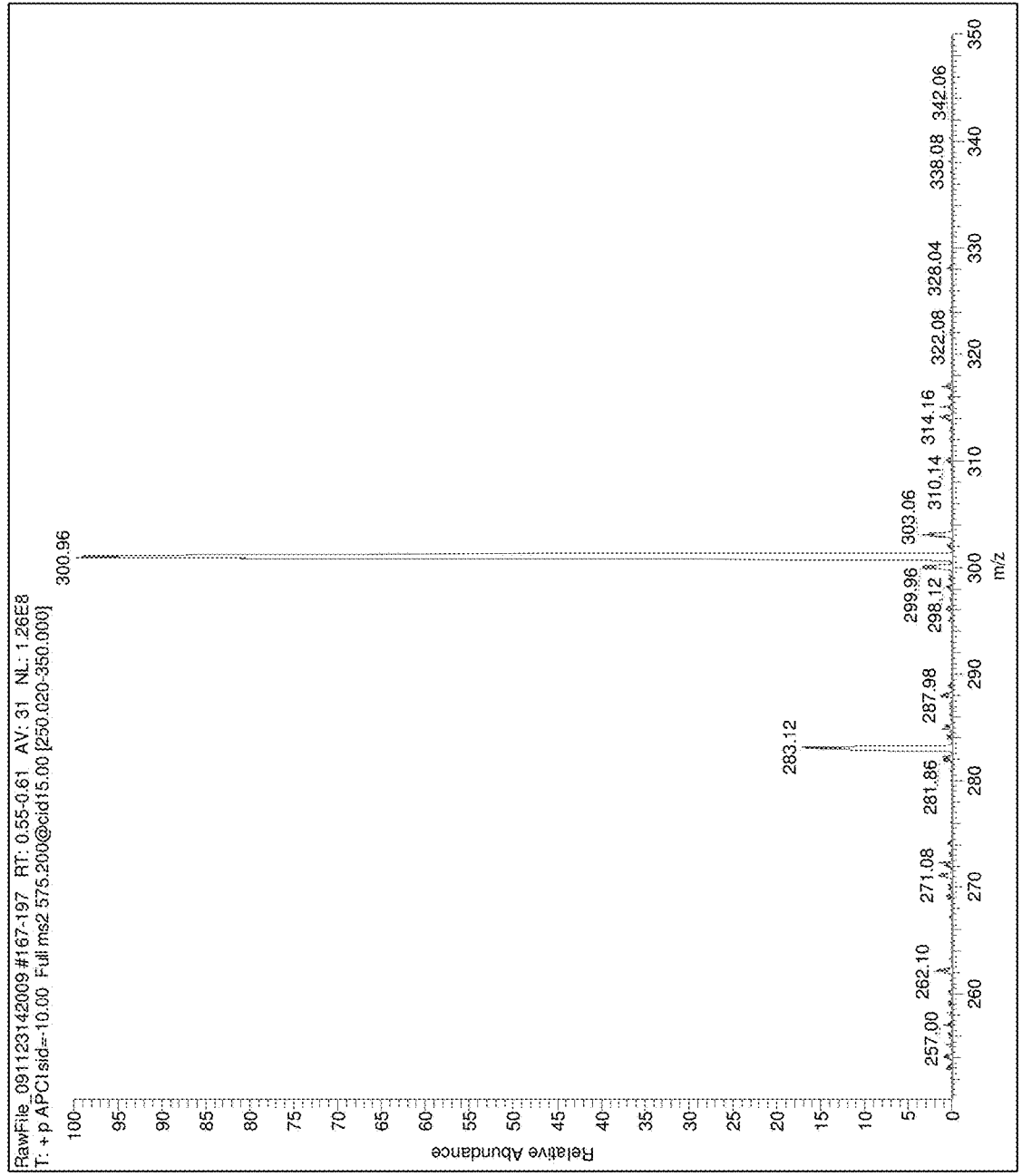
FIG. 12B shows an exemplary product ion spectra (covering the m/z range of about 250 to 350) for fragmentation of the PTAD-vitamin $D_2$-[6, 19, 19]-$^2H_3$ precursor ion with m/z of about 575.2. Details are described in Example 15.
Figure 13B:
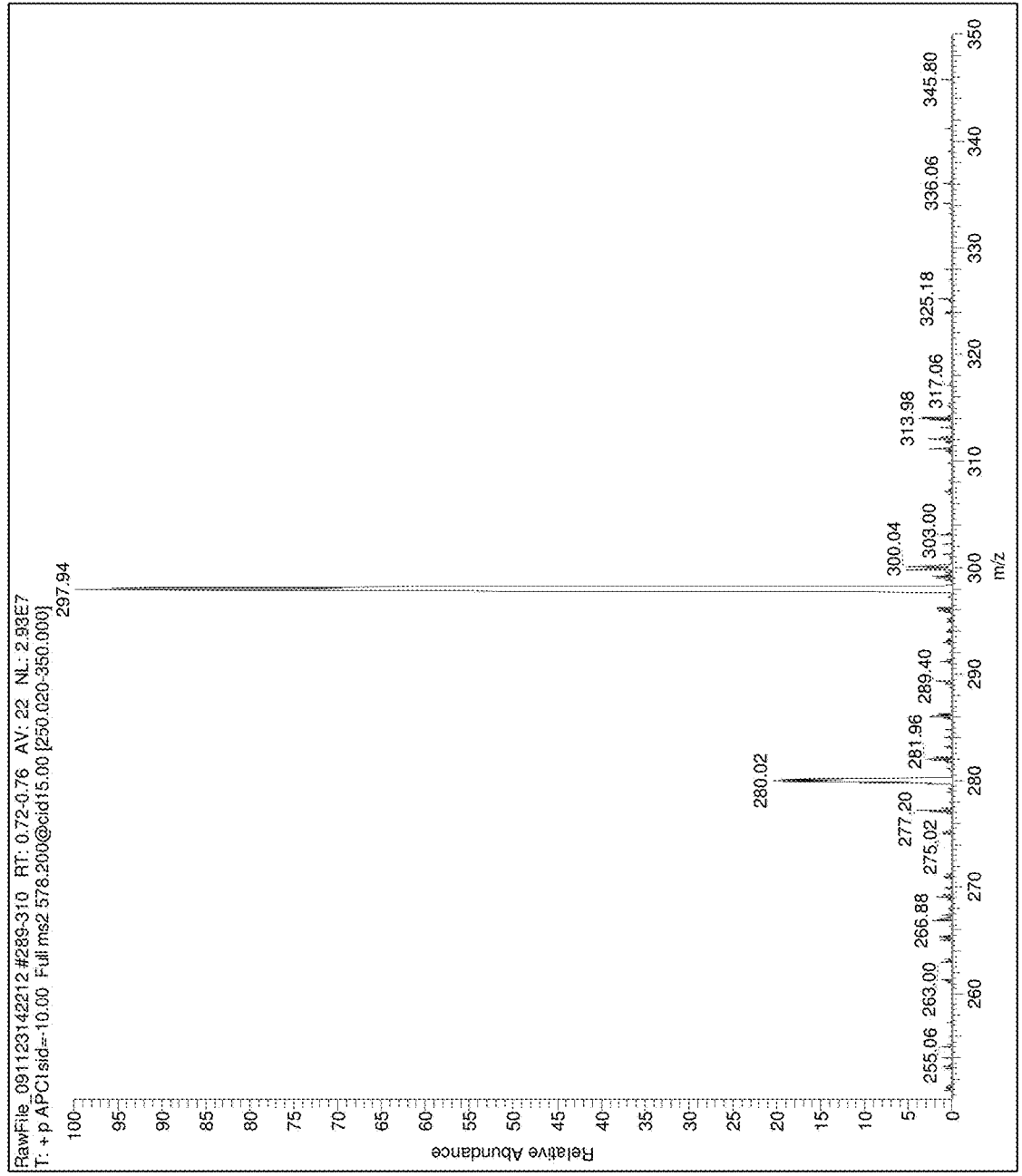
FIG. 13B shows an exemplary product ion spectra (covering the m/z range of about 250 to 350) for fragmentation of the PTAD-vitamin $D_2$-[26, 26, 26, 27, 27, 27]-$^2H_6$ precursor ion with m/z of about 578.2. Details are described in Example 15.

Exemplary product ion scans generated from precursor ions for each of PTAD-vitamin $D_2$, PTAD-vitamin $D_2$-[6, 19, 19]-$^2H_3$, and PTAD-vitamin $D_2$-[26, 26, 26, 27, 27, 27]-$^2H_6$ are presented in FIGS. 11B, 12B, and 13B, respectively. The precursor ions selected in Q1 and the collision energies used to generate these product ion spectra are indicated in Table 22.

An exemplary MRM transition for the quantitation of PTAD-vitamin $D_2$ includes fragmenting a precursor ion with a m/z of about 572.2 to a product ion with a m/z of about 297.9. An exemplary MRM transition for the quantitation of PTAD-vitamin $D_2$-[6, 19, 19]-$^2H_3$ includes fragmenting a precursor ion with a m/z of about 575.2 to a product ion with a m/z of about 301.0. An exemplary MRM transition for the quantitation of PTAD-vitamin $D_2$-[26, 26, 26, 27, 27, 27]-$^2H_6$ includes fragmenting a precursor ion with a m/z of about 578.2 to a product ion with a m/z of about 297.9. However, as can be seen in the product ion scans in FIGS. 11B, 12B, and 13B, several other product ions are generated upon fragmentation of the precursor ions. Additional product ions may be selected from those indicated in FIGS. 11B, 12B, and 13B to replace or augment the exemplary fragment ions. For example, additional product ions generated by fragmentation of the PTAD-vitamin $D_2$ precursor ion with m/z of about 572.2 include ions with m/z of about 280.1.

TABLE 22

Precursor Ions and Collision Cell Energies
for Fragmentation of PTAD-vitamin
$D_2$, PTAD-vitamin $D_2$-[6,19,19]-$^2H_3$,
and PTAD-vitamin $D_2$-[26,26,26,27,27,27]-$^2H_6$

| Analyte | Precursor Ion (m/z) | Collision Cell Energy (V) |
|---|---|---|
| PTAD-vitamin $D_2$ | 572.2 | 15 |
| PTAD-vitamin $D_2$-[6,19,19]-$^2H_3$ | 575.2 | 15 |
| PTAD-vitamin $D_2$-[26,26,26,27,27,27]-$^2H_6$ | 578.2 | 15 |

Figure 14A:
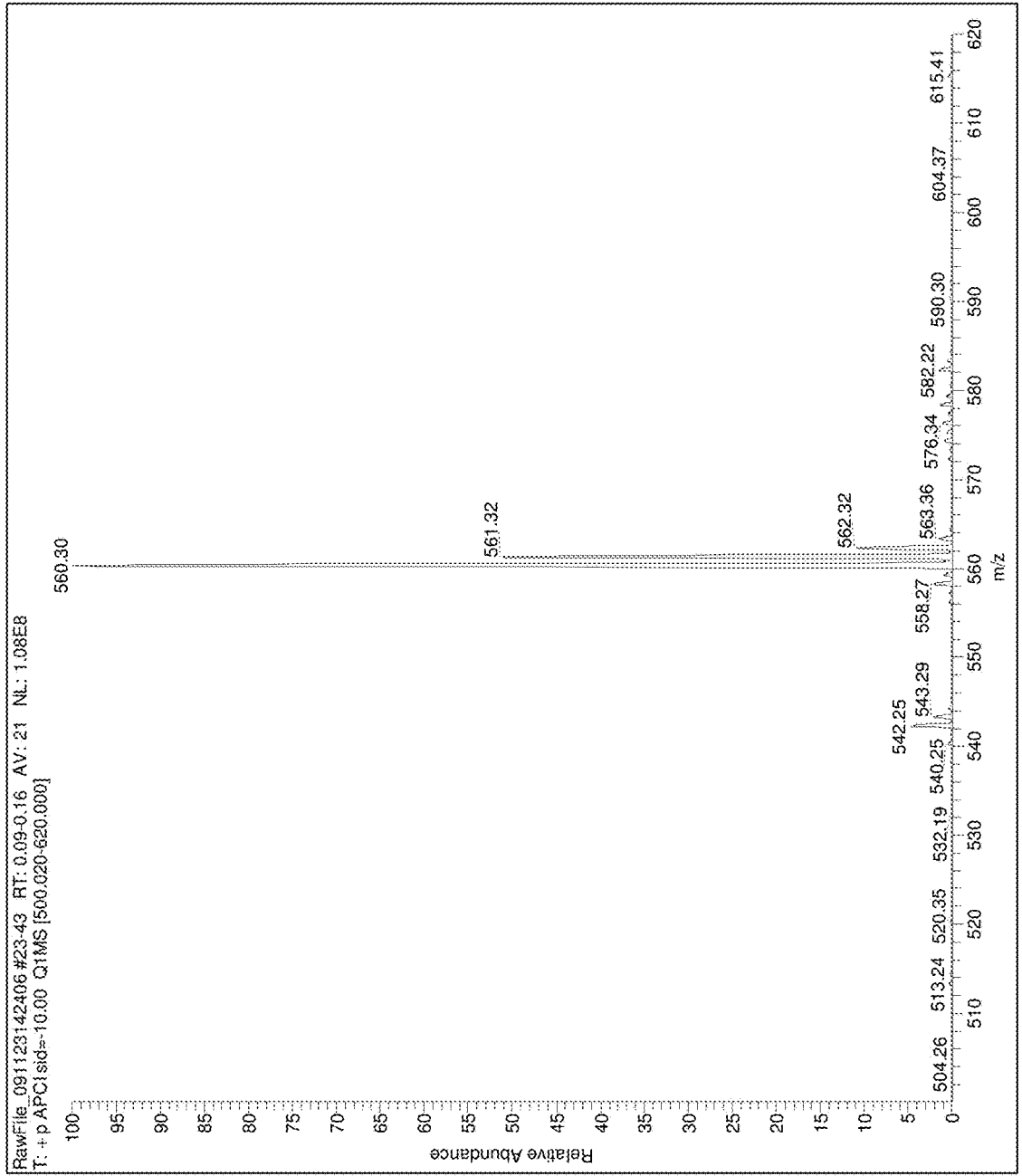
FIG. 14A shows an exemplary Q1 scan spectrum (covering the m/z range of about 500 to 620) for PTAD-vitamin $D_3$ ions.
Figure 15A:
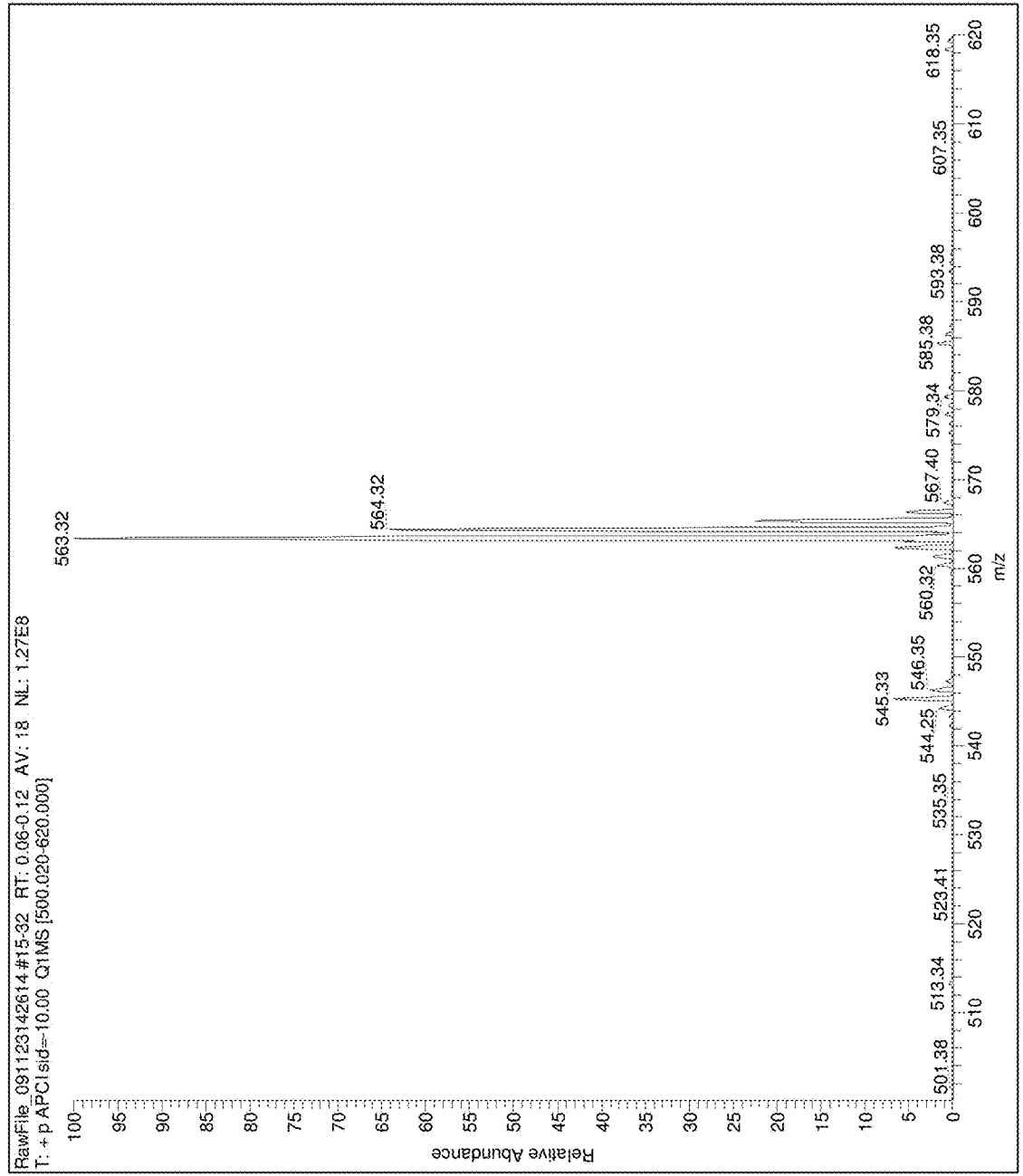
FIG. 15A shows an exemplary Q1 scan spectrum (covering the m/z range of about 500 to 620) for PTAD-vitamin $D_3$-[6, 19, 19]-$^2H_3$ ions.
Figure 16A:
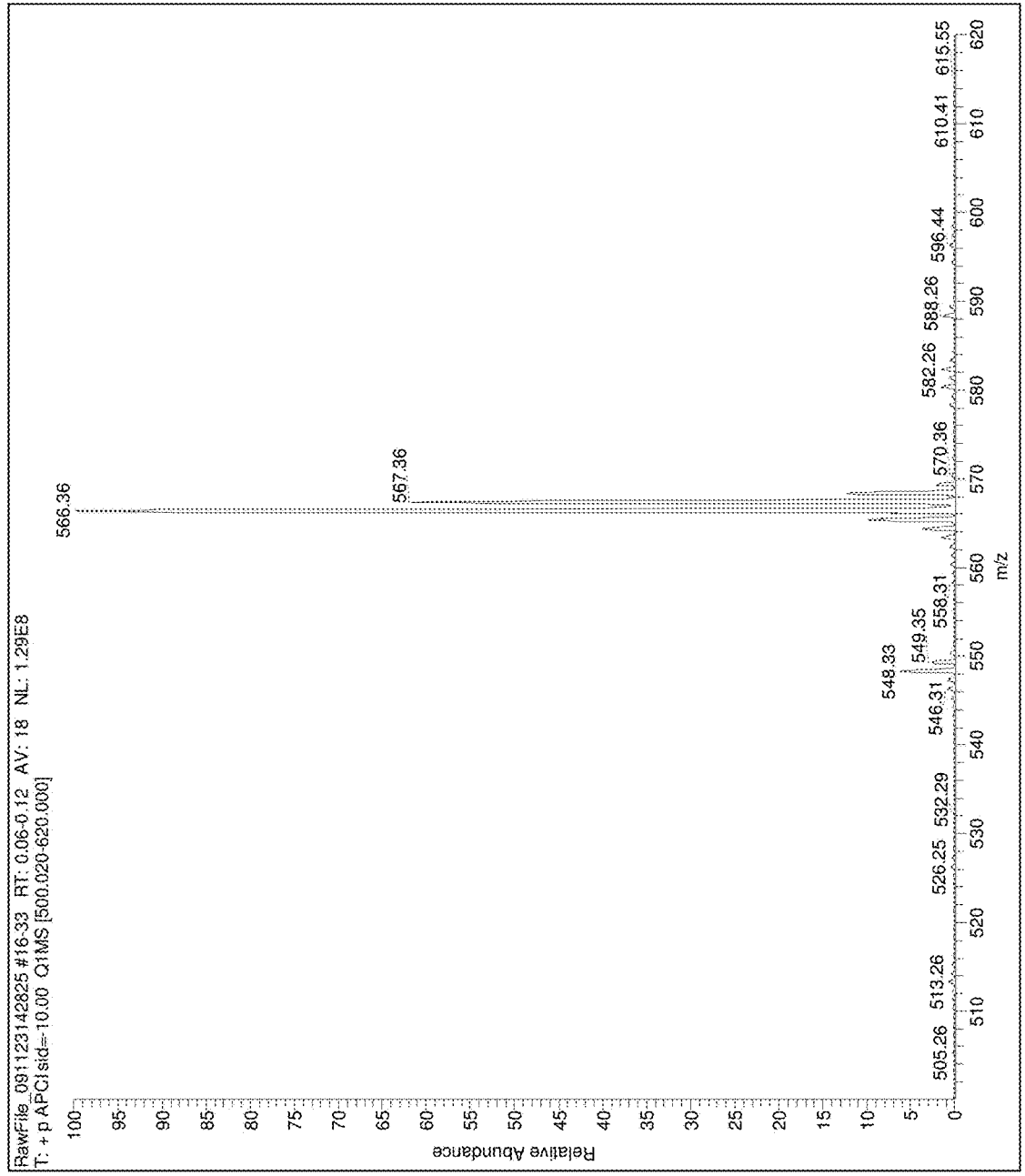
FIG. 16A shows an exemplary Q1 scan spectrum (covering the m/z range of about 500 to 620) for PTAD-vitamin $D_3$-[26, 26, 26, 27, 27, 27]-$^2H_6$ ions.

Exemplary Q1 scan spectra from the analysis of samples containing PTAD-vitamin $D_3$, PTAD-vitamin $D_3$-[6, 19, 19]-$^2H_3$, and PTAD-vitamin $D_3$-[26, 26, 26, 27, 27, 27]-$^2H_6$ are shown in FIGS. 14A, 15A, and 16A, respectively. These analyses were conducted by directly injecting standard solutions containing the analyte of interest into a Finnigan TSQ Quantum Ultra MS/MS system (Thermo Electron Corporation). A liquid chromatography mobile phase was simulated by passing 800 µL/min of 80% acetonitrile, 20% water with 0.1% formic acid through an HPLC column, upstream of introduction of the analyte. The spectra were collected by scanning Q1 across a m/z range of about 500 to 620.

Figure 14B:
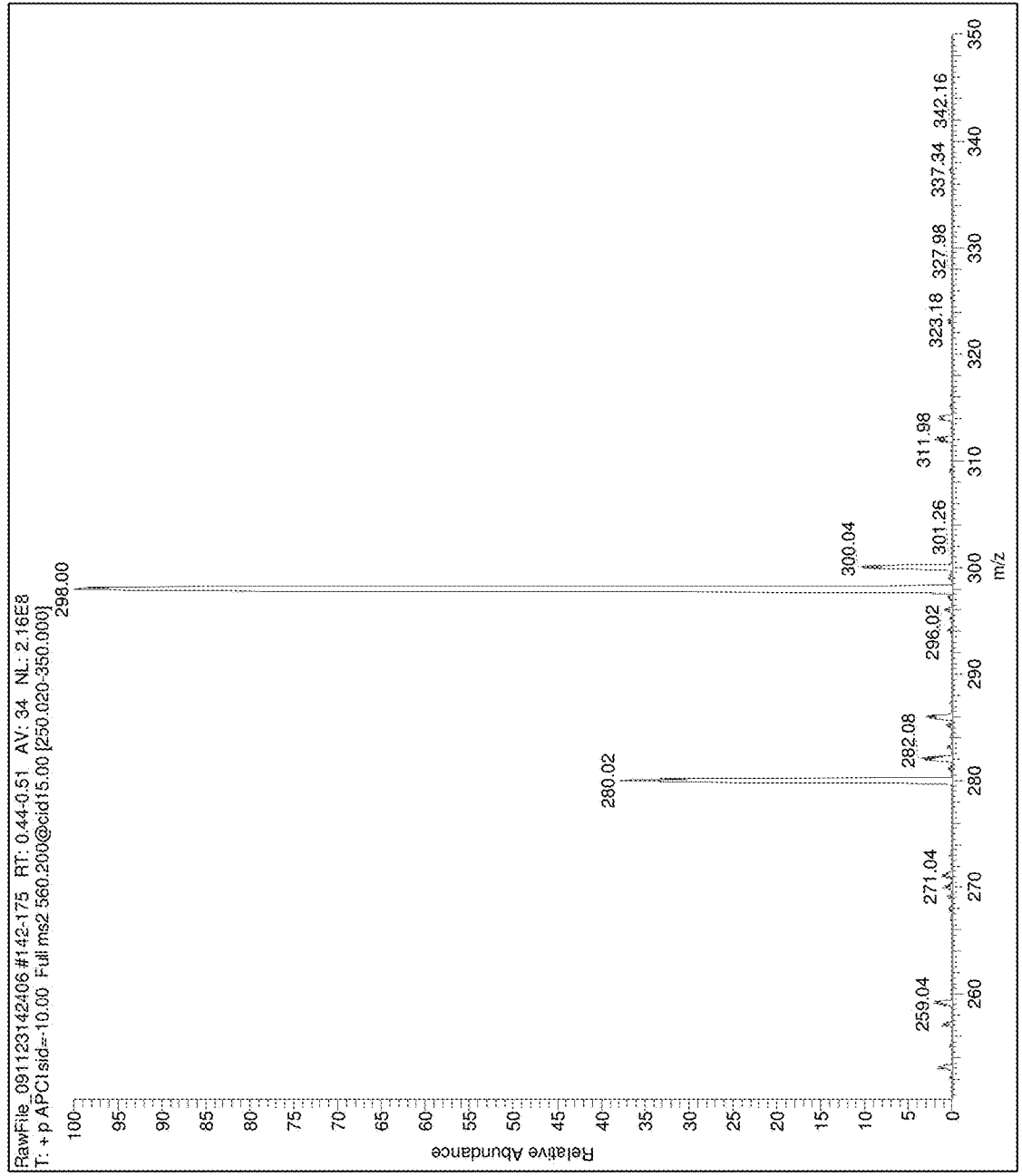
FIG. 14B shows an exemplary product ion spectra (covering the m/z range of about 250 to 350) for fragmentation of the PTAD-vitamin $D_3$ precursor ion with m/z of about 560.2. Details are described in Example 15.
Figure 15B:
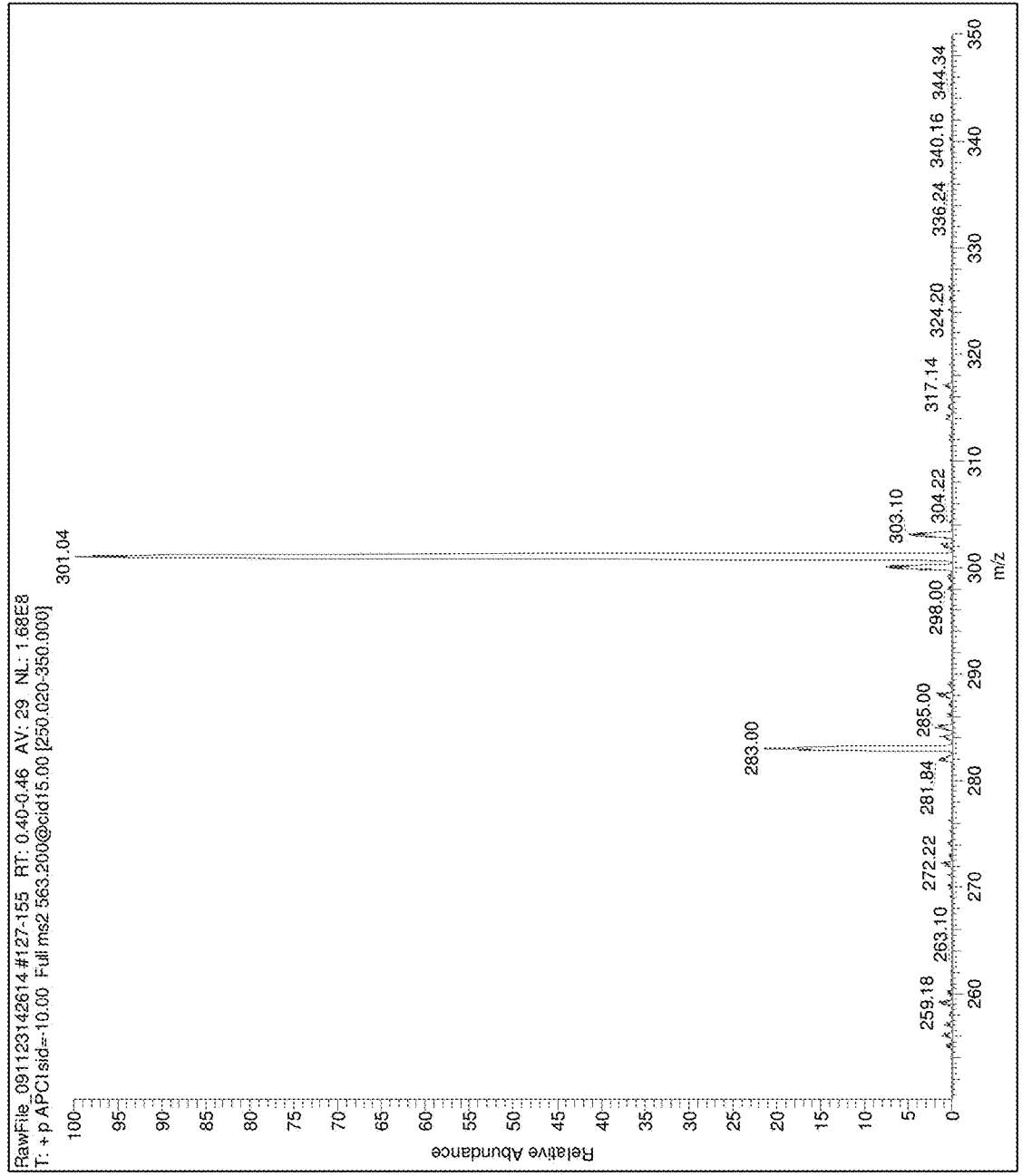
FIG. 15B shows an exemplary product ion spectra (covering the m/z range of about 250 to 350) for fragmentation of the PTAD-vitamin $D_3$-[6, 19, 19]-$^2H_3$ precursor ion with m/z of about 563.2. Details are described in Example 15.
Figure 16B:
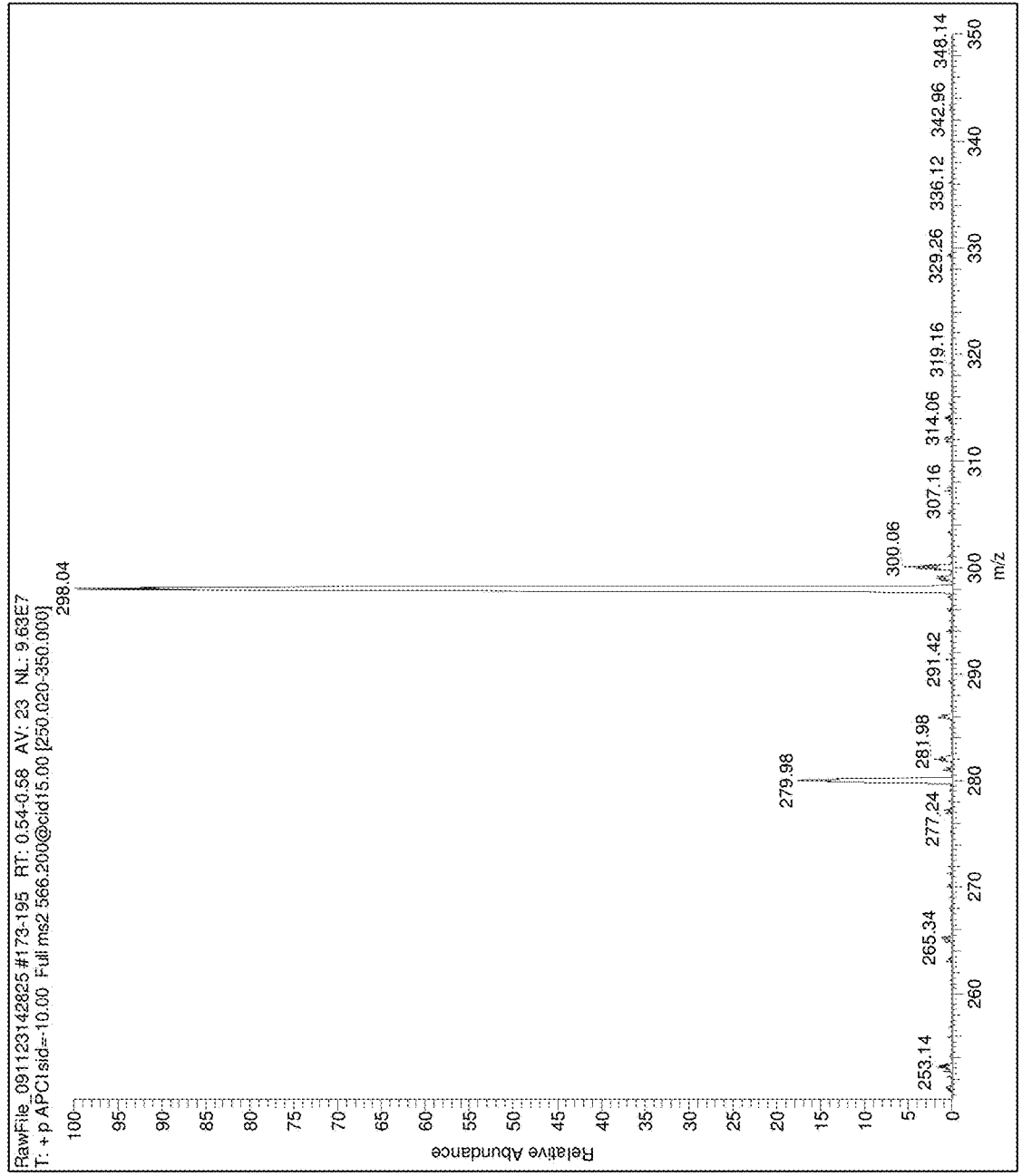
FIG. 16B shows an exemplary product ion spectra (covering the m/z range of about 250 to 350) for fragmentation of the PTAD-vitamin $D_3$-[26, 26, 26, 27, 27, 27]-$^2H_6$ precursor ion with m/z of about 566.2. Details are described in Example 15.

Exemplary product ion scans generated from precursor ions for each of PTAD-vitamin $D_3$, PTAD-vitamin $D_3$-[6, 19, 19]-$^2H_3$, and PTAD-vitamin $D_3$-[26, 26, 26, 27, 27, 27]-$^2H_6$ are presented in FIGS. 14B, 15B, and 16B, respectively. The precursor ions selected in Q1 and the collision energies used to generate these product ion spectra are indicated in Table 23.

An exemplary MRM transition for the quantitation of PTAD-vitamin $D_3$ includes fragmenting a precursor ion with a m/z of about 560.2 to a product ion with a m/z of about 298.0. An exemplary MRM transition for the quantitation of PTAD-vitamin $D_3$-[6, 19, 19]-$^2H_3$ includes fragmenting a precursor ion with a m/z of about 563.2 to a product ion with a m/z of about 301.0. An exemplary MRM transition for the quantitation of PTAD-vitamin $D_3$-[26, 26, 26, 27, 27, 27]-$^2H_6$ includes fragmenting a precursor ion with a m/z of about 566.2 to a product ion with a m/z of about 298.0. However, as can be seen in the product ion scans in FIGS. 14B, 15B, and 16B, several other product ions are generated upon fragmentation of the precursor ions. Additional product ions may be selected from those indicated in FIGS. 14B, 15B, and 16B to replace or augment the exemplary fragment ions. For example, additional product ions generated by fragmentation of the PTAD-vitamin $D_3$ precursor ion with m/z of about 560.2 include ions with m/z of about 280.0.

TABLE 23

Precursor Ions and Collision Cell Energies
for Fragmentation of PTAD-vitamin
$D_3$, PTAD-vitamin $D_3$-[6,19,19]-$^2H_3$,
and PTAD-vitamin $D_3$-[26,26,26,27,27,27]-$^2H_6$

| Analyte | Precursor Ion (m/z) | Collision Cell Energy (V) |
|---|---|---|
| PTAD-vitamin $D_3$ | 560.2 | 15 |
| PTAD-vitamin $D_3$-[6,19,19]-$^2H_3$ | 563.2 | 15 |
| PTAD-vitamin $D_3$-[26,26,26,27,27,27]-$^2H_6$ | 566.2 | 15 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of non-metabolized vitamin $D_2$ in a sample by tandem mass spectrometry, the method comprising the steps of:
   (i) subjecting non-metabolized vitamin $D_2$ from a sample to an ionization source under conditions suitable to generate one or more precursor ions comprising a mass to charge ratio (m/z) of 397.2±0.5;
   (ii) fragmenting at least one of said precursor ions to generate one or more fragment ions detectable by mass spectrometry, wherein the fragment ions comprise one or more ions selected from the group consisting of ions with m/z of 159.0±0.5, 146.9±0.5, 133.1±0.5, and 121.0±0.5;
   (iii) determining the amount of one or more of the fragment ions generated in step (ii) by mass spectrometry; and
   (iv) relating the presence of non-metabolized vitamin $D_2$ ions determined in step (iii) to the presence of non-metabolized vitamin $D_2$ in the sample.

2. The method of claim 1, wherein the sample is subjected to an extraction column prior to ionization.

3. The method of claim 2, wherein the extraction column is a solid phase extraction (SPE) column.

4. The method of claim 2, wherein the extraction column is a turbulent flow liquid chromatography (TFLC) column.

5. The method of claim 1, wherein the sample is further subjected to an analytical column prior to ionization.

6. The method of claim 5, wherein the analytical column is a high performance liquid chromatography (HPLC) column.

7. The method of claim 5, wherein the extraction and analytical columns and the ionization source of step (i) are connected in an on-line fashion.

8. The method of claim 1, wherein said ionization source is an atmospheric pressure chemical ionization (APCI) source.

9. The method of claim 1, wherein said mass spectrometry is conducted as multiple reaction monitoring, precursor ion scanning, or product ion scanning.

10. The method of claim 1, further comprising detecting non-metabolized vitamin $D_3$ in the sample, wherein the non-metabolized vitamin $D_2$ and non-metabolized vitamin $D_3$ are ionized simultaneously.

11. The method of claim 10, wherein detecting the non-metabolized vitamin $D_3$ comprises determining the amount of one or more fragment ions selected from the group consisting of ions with m/z of 172.2±0.5, 145.0±0.5, and 119.1±0.5.

12. The method of claim 10, wherein detecting the non-metabolized vitamin $D_3$ comprises determining the amount of one or more fragment ions selected from the group consisting of ions with m/z of 159.0±0.5, 147.0±0.5, 133.1±0.5, and 107.1±0.5.

13. The method of claim 1, wherein the sample comprises a biological sample, and wherein said biological sample is from a human, and the amount of non-metabolized vitamin $D_2$ determined in the sample is the amount present in the sample when taken from the human.

14. The method of claim 1, wherein the sample comprises serum or plasma.

* * * * *